(12) United States Patent
Vainikka et al.

(10) Patent No.: US 10,400,008 B2
(45) Date of Patent: Sep. 3, 2019

(54) MODULATORS OF THE SRC-KINASE ACTIVITY FOR PREVENTING OR TREATING METASTATIC CANCER

(71) Applicant: Cancer Research Technology Limited, London (GB)

(72) Inventors: Satu Vainikka, London (GB); George Steven Morris, London (GB); Samuel Ogunsalu, London (GB); Gabriella Castoria, Naples (IT); Antimo Migliaccio, Naples (IT); Ferdinando Auricchio, Naples (IT)

(73) Assignee: Cancer Research Technology Limited, London (GB)

( * ) Notice: Subject to any disclaimer, the term of this patent is extended or adjusted under 35 U.S.C. 154(b) by 181 days.

(21) Appl. No.: 14/888,214

(22) PCT Filed: Apr. 30, 2014

(86) PCT No.: PCT/GB2014/051347
§ 371 (c)(1),
(2) Date: Oct. 30, 2015

(87) PCT Pub. No.: WO2014/177868
PCT Pub. Date: Nov. 6, 2014

(65) Prior Publication Data
US 2016/0068568 A1    Mar. 10, 2016

(30) Foreign Application Priority Data

May 1, 2013 (GB) .................................. 1307872.0

(51) Int. Cl.
| | |
|---|---|
| *A61K 38/08* | (2019.01) |
| *C07K 7/06* | (2006.01) |
| *A61K 45/06* | (2006.01) |
| *A61K 39/395* | (2006.01) |
| *C07K 16/40* | (2006.01) |

(52) U.S. Cl.
CPC .............. *C07K 7/06* (2013.01); *A61K 38/08* (2013.01); *A61K 39/3955* (2013.01); *A61K 45/06* (2013.01); *C07K 16/40* (2013.01)

(58) Field of Classification Search
None
See application file for complete search history.

(56) References Cited

U.S. PATENT DOCUMENTS

| | | | |
|---|---|---|---|
| 5,228,707 A | 7/1993 | Yoder | |
| 5,550,251 A | 8/1996 | Hirschmann et al. | |
| 5,552,534 A | 9/1996 | Hirschmann et al. | |
| 7,863,289 B2 | 1/2011 | Spevak et al. | |
| 7,943,629 B2 | 5/2011 | Lueeking et al. | |
| 7,956,053 B2 | 6/2011 | Breitenstein et al. | |
| 7,960,396 B2 | 6/2011 | Honigberg et al. | |
| 10,023,612 B2 | 7/2018 | Eccleston et al. | |
| 2008/0058358 A1 | 3/2008 | Lueeking et al. | |
| 2008/0063654 A1 | 3/2008 | McNeel et al. | |
| 2008/0167338 A1 | 7/2008 | Spevak et al. | |
| 2009/0286821 A1 | 11/2009 | Breitenstein et al. | |
| 2010/0331350 A1 | 12/2010 | Honigberg et al. | |
| 2014/0322306 A1 | 10/2014 | Eccleston et al. | |
| 2018/0273585 A1 | 9/2018 | Eccleston et al. | |

FOREIGN PATENT DOCUMENTS

| | | |
|---|---|---|
| GB | 2496135 A | 5/2013 |
| WO | 1998/046250 A1 | 10/1998 |
| WO | 2000/001813 A2 | 1/2000 |
| WO | WO 2008/113770 A2 | 9/2008 |
| WO | 2009/132307 A1 | 10/2009 |
| WO | WO 2013/064830 A2 | 5/2013 |
| WO | WO 2014/177868 A2 | 11/2014 |

OTHER PUBLICATIONS

Asim et al., "Src kinase potentiates androgen receptor transactivation function and invasion of androgen-independent prostate cancer C4-2 cells", Oncogene, 2008, pp. 3596-3604 (Year: 2008)*
Bales et al., "A Controlled Trial of Bicalutamide Versus Castration in Patients With Advanced Prostate Cancer", Urology, 1996, pp. 38-43 (Year: 1996).*
International Search Report and Written Opinion for Int'l Application No. PCT/GB2014/051347, titled: Modulators of The SRCE-Kinase Activity for Preventing or Treating Metastatic Cancer, dated Dec. 11, 2014.
International Preliminary Report on Patentability for Int'l Application No. PCT/GB2014/051347, titled: Modulators of The SRCE-Kinase Activity for Preventing or Treating Metastatic Cancer, dated Nov. 3, 2015.
GB Search Report for GB Application No. GB1307872.0, dated Oct. 30, 2013.

(Continued)

*Primary Examiner* — Lianko G Garyu
(74) *Attorney, Agent, or Firm* — Hamilton, Brook, Smith & Reynolds, P.C.

(57) ABSTRACT

The invention provides a molecule that modulates an activity of a Src family kinase for use in preventing or treating a metastatic cancer a subject. Preferably, the molecule comprises or consists of the structure: $B_j$-[(Pro)$_n$-X$_r$-His-Pro-His-Ala-Arg-Ile-Lys]$_m$-R$_p$, or $B_j$-[lys-ile-arg-ala-his-pro-his-x$_r$-(pro)$_n$]$_m$-R$_p$, or a derivative or fragment thereof, wherein B is a first chemical moiety, j is 0 or 1, n is an integer from 1-10, X is any amino acid, r is an integer from 0 to 2, m is an integer from 1 to 3, R is a second chemical moiety, p is 0 or 1, and [lys-ile-arg-ala-his-pro-his-x$_r$-(pro)$_n$] is the retro-inverso peptide of [(Pro)n-X$_r$-His-Pro-His-Ala-Arg-Ile-Lys].

8 Claims, 20 Drawing Sheets
Specification includes a Sequence Listing.

(56) References Cited

OTHER PUBLICATIONS

Anonymous, "Pharmatest to exhibit and present new data at the AACR 2013 meeting," Retrieved from the internet: http://www.pharmatest.com/index.php/news/pharmatest-exhibit-and-present-new-data-aacr-2013-meeting, Retrieved on: Jul. 21, 2014.
Auricchio, F. and A. Migliaccio, "VAL 201—An inhibitor of Androgen Receptor-associated SRC and a Potential Treatment of Castration-resistant Prostate Cancer," *European Oncology and Haematology*, 8(1): 32-35 (Jan. 1, 2012).
Migliaccio, A. et al., "Inhibition of the SH3 domain-mediated binding of SRC to the androgen receptor and its effect on tumor growth," *Oncogene*, 26(46): 6619-6629 (Oct. 11, 2007).
Migliaccio, A. et al., "Steroid-induced androgen receptor-oestradiol receptor β-Src complex triggers prostate cancer cell proliferation," *The EMBO Journal*, 19(20): 5406-5417 (Oct. 16, 2000).
Morris, G.S. et al., "Abstract 2080: Inhibiting androgen receptor-associated Src signaling by VAL201 inhibits prostate cancer metastasis in an orthotopic mouse model," Retrieved from the internet: http://cancerres.aacrjournals.org/cgi/content/meeting_abstract/73/8_MeetingAbstracts/2080, Retrieved on: Jul. 21, 2014.
Morris, G.S. et al., "Inhibiting androgen receptor-associated Src signaling by VAL201 inhibits prostate cancer metastasis in an orthotopic mouse model," Retrieved from the internet: http://www.pharmatest.com/files/4013/8022/1888/AACR_2013_poster_2080.pdf, Retrieved on: Jul. 21, 2014.
Suominen, M.I. et al., "Abstract 992: Inhibiting androgen receptor associated Src signaling with VAL201 inhibits breast cancer growth in an orthotopic xenograft model," Retrieved from the internet: http://cancerres.aacrjournals.org/cgi/content/meeting_abstract/73/8_MeetingAbstracts/922, Retrieved on: Jul. 21, 2014.
Bodanszky, M., "Techniques for the Facilitation of Peptide Synthesis", *Principles of Peptide Synthesis*, Edited by Hather, K., et al., Chapter 7: 233-251 (1984).
Bogush, T. A., et al., "Estrogen Receptors, Antiestrogens, and Non-Small Cell Lung Cancer", *Biochemistry (Moscow)*, vol. 75, No. 12: 1421-1427 (2010).
Castoria, G., et al., "Androgen-stimulated DNA synthesis and cytoskeletal changes in fibroblasts by a nontranscriptional receptor action", *The Journal of Cell Biology*, vol. 161, No. 3: 547-556 (2003).
Castoria, G., et al., "Androgen-Induced Cell Migration: Role of Androgen Receptor/Filamin A Association", *PLoSOne*, vol. 6, No. 2, e17218: 1-16 (2011).
Castoria, G., et al., "Tyrosine phosphorylation of estradiol receptor by Src regulates its hormone-dependent nuclear export and cell cycle progression in breast cancer cells", *Oncogene*, vol. 31: 4868-4877 (2012).
Chang, C., et al., "Structural analysis of complementary DNA and amino acid sequences of human and rat androgen receptors", *Proc. Natl. Acad. Sci.*, vol. 85: 7211-7215 (1988).
Chaudhuri, P. K., et al., "Presence of Steroid Receptors in Human Soft Tissue Sarcomas of Diverse Histological Origin", *Cancer Research*, vol. 40: 861-865 (1980).
Chauhan, S., et al., "Androgen Control of Cell Proliferation and Cytoskeletal Reorganization in Human Fibrosarcoma Cells: Role of RhoB Signaling", *J. Biol. Chem.*, vol. 279, No. 2: 937-944 (2004).
Cortes-Reynosa, P., et al., "Src kinase regulates metalloproteinase-9 secretion induced by type IV collagen in MCF-7 human breast cancer cells", *Matrix Biology*, vol. 27: 220-231 (2008).
Deshayes, S., et al., "Cell-penetrating peptides: tools for intracellular delivery of therapeutics", *Cellular and Molecular Life Sciences*, vol. 62: 1839-1849 (2005).
Deshayes, S., et al., "Interactions of Primary Amphipathic Cell Penetrating Peptides with Model Membranes: Consequences on the Mechanisms of Intracellular Delivery of Therapeutics", *Current Pharmaceutical Design*, vol. 11: 3629-3638 (2005).
Di Domenico, M., et al., "Estradiol Activation of Human Colon Carcinoma-derived Caco-2 Cell Growth", *Cancer Research*, vol. 56: 4516-4521 (1996).
Dugas, H. and Penney, C., "Biological Synthesis of Proteins", In *Bioorganic Chemistry A Chemical Approach to Enzyme Action*, Edited by Cantor, C. R.: 43-82 (1981).
Duncan, R. J. S., et al., "A New Reagent Which May Be Used to Introduce Sulfhydryl Groups into Proteins, and Its Use in the Preparation of Conjugates for Immunoassay", *Analytical Biochemistry*, vol. 132: 68-73 (1983).
Giovannoni, L., et al., "Isolation of anti-angiogenesis antibodies from a large combinatorial repertoire by colony filter screening", *Nucleic Acids Research*, vol. 29, No. 5, e27: 1-6 (2001).
Harlow, E. and Lane, D., *Antibodies: A Laboratory Manual*, Table of Contents (1988).
Harlow, E. and Lane, D., *Using Antibodies: A Laboratory Manual*, Table of Contents (1999).
Janeway, C. A., et al., *Immunobiology The Immune System in Health and Disease*, Table of Contents (2001).
Jung, H. H., et al., "Matrix Metalloproteinase-1 Expression Can Be Upregulated through Mitogen-Activated Protein Kinase Pathway under the Influence of Human Epidermal Growth Factor Receptor 2 Synergized with Estrogen Receptor", *Molecular Cancer Research*, vol. 8, No. 7: 1037-1047 (2010).
Knight, C. G., et al., "A novel coumarin-labelled peptide for sensitive continuous assays of the matrix metalloproteinases", *Federation of European Biochemical Societies*, vol. 296, No. 3: 263-266 (1992).
Köhler, G. and Milstein, C., "Continuous cultures of fused cells secreting antibody of predefined specificity", *Nature*, vol. 256: 495-497 (1975).
Lindgren, M., et al., "Cell-penetrating peptides", *TiPS*, vol. 21: 99-103 (2000).
Lombardi, M., et al., "Hormone-dependent nuclear export of estradiol receptor and DNA synthesis in breast cancer cells", *J. Cell Biology*, vol. 182, No. 2: 327-340 (2008).
Luo, W., et al., "Global Impact of Oncogenic Src on a Phosphotyrosine Proteome", *J. Proteome Research*, vol. 7, No. 8: 3447-3460 (2008).
McCawley, L. J. and Matrisian, L. M., "Matrix metalloproteinases: they're not just for matrix anymore!", *Current Opinion in Cell Biology*, vol. 13: 534-540 (2001).
Merrifield, R. B., "Solid Phase Peptide Synthesis. I. The Synthesis of a Tetrapeptide", *Contributed by the Rockefeller Institute*, vol. 85: 2149-2154 (1963).
Meziere, C., et al., "In Vivo T Helper Cell Response to Retro-Inverso Peptidomimetics", *The Journal of Immunology*, vol. 159: 3230-3237 (1997).
Migliaccio, A., et al., "Steroid Receptor Regulation of Epidermal Growth Factor Signaling through Src in Breast and Prostate Cancer Cells: Steroid Antagonist Action", *Cancer Research*, vol. 65, No. 22: 10585-10593 (2005).
Migliaccio, A., et al., "Cross talk between epidermal growth factor (EGF) receptor and extra nuclear steroid receptors in cell lines", *Molecular and Cellular Endocrinology*, vol. 327: 19-24 (2010).
Migliaccio, A., et al., "Analysis of Androgen Receptor Rapid Actions in Cellular Signaling Pathways: Receptor/Src Association", *Androgen Action,Methods in Molecular Biology*, vol. 776: 361-370 (2011).
Moldenhauer, G., "Selection Strategies I: Monoclonal Antibodies", in *Handbook of Therapeutic Antibodies, vol. 1: Technologies*, Edited by Dübel, S., 19-44 (2007).
Murray, N. P. et al., "Differential Expression of Matrix Metalloproteinase-2 Expression in Disseminated Tumor Cells and Micrometastasis in Bone Marrow of Patients with Nonmetastatic and Metastatic Prostate Cancer: Theoretical Considerations and Clinical Implications—An Immunocytochemical Study", *Bone Marrow Research*, vol. 2012: 1-9 (2012).
O'Sullivan, M. J., et al., "Comparison of Two Methods of Preparing Enzyme-Antibody Conjugates: Application of These Conjugates for Enzyme Immunoassay", *Analytical Biochemistry*, vol. 100: 100-108 (1979).
Partridge, J. J., et al., "Functional Analysis of Matrix Metalloproteinases and Tissue Inhibitors of Metalloproteinases Differen-

(56) References Cited

OTHER PUBLICATIONS tially Expressed by Variants of Human HT-1080 Fibrosarcoma Exhibiting High and Low Levels of Intravasation and Metastasis", *The Journal of Biological Chemistry*, vol. 282, No. 49: 35964-35977 (2007).
Plant, A. L., et al., "Phospholipid/Alkanethiol Bilayers for Cell-Surface Receptor Studies by Surface Plasmon Resonance", *Analytical Biochemistry*, vol. 226: 342-348 (1995).
Rich, D. H., "Inhibitors of cysteine proteinases", Chapter 4, *Proteinase Inhibitors*, Edited by Barrett, A. J. and Salvesen, G., *Research monographs in cell and tissue physiology*, Edited by Dingle, J. T. and Gordon, J. L., vol. 12: 153-178 (1986).
Sambrook, J. and Russell, D. W., *Molecular Cloning A Laboratory Manual*, vol. 1, Table of Contents (2001).
Schaffitzel, C., et al., "Ribosome display: an in vitro method for selection and evolution of antibodies from libraries", *Journal of Immunological Methods*, vol. 231: 119-135 (1999).
Sherman, D. B. and Spatola, A. F., "Compatibility of Thioamides with Reverse Turn Features: Synthesis and Conformational Analysis of Two Model Cyclic Pseudopeptides Containing Thioamides as Backbone Modifications", *J. Am Chem.*, vol. 112: 433-441 (1990).
Smith, M. M., et al., "Rapid Identification of Highly Active and Selective Substrates for Stromelysin and Matrilysin Using Bacteriophage Peptide Display Libraries", *The Journal of Biological Chemistry*, vol. 270, No. 12: 6440-6449 (1995).
Stabile, L. P., et al., "Human Non-Small Cell Lung Tumors and Cells Derived from Normal Lung Express Both Estrogen Receptor α and β and Show Biological Responses to Estrogen", *Cancer Research*, vol. 62: 2141-2150 (2002).
Takeuchi, T., et al., "Direct and Rapid Cytosolic Delivery Using Cell-Penetrating Peptides Mediated by Pyrenebutyrate", *ACS Chemical Biology*, vol. 1, No. 5: 299-303 (2006).
Thompson, J. D., et al., "CLUSTAL W: improving the sensitivity of progressive multiple sequence alignment through sequence weighting, position-specific gap penalties and weight matrix choice", *Nucleic Acids Research*, vol. 22, No. 22: 4673-4680 (1994).
Thorsett, E. D., et al., "Dipeptide mimics. Conformationally restricted inhibitors of angiotensin-converting enzyme", *Biochemical and Biophysical Research Communications*, vol. 111, No. 1: 166-171 (1983).
Tuomela, J. M., et al., "Alendronate decreases orthotopic PC-3 prostate tumor growth and metastasis to prostate-draining lymph nodes in nude mice", *BMC Cancer*, vol. 8, No. 81: 12 pp. (2008).
Tuomela, J., et al., "Overexpression of vascular endothelial growth factor C increases growth and alters the metastatic pattern of orthotopic PC-3 prostate tumors", *BMC Cancer*, vol. 9, No. 362: 12 pages (2009).
Yalta, M. P., et al., "FGF-8b Induces Growth and Rich Vascularization in an Orthotopic PC-3 Model of Prostate Cancer", *Journal of Cellular Biochemistry*, vol. 107: 769-784 (2009).
Vanderschueren, D., et al., "Androgens and bone", *Current Opinion in Endocrinology, Diabetes & Obesity*, vol. 15: 250-254 (2008).
Varricchio, L., et al., "Inhibition of Estradiol Receptor/Src Association and Cell Growth by an Estradiol Receptor α Tyrosine-Phosphorylated Peptide", *Molecular Cancer Research*, vol. 5, No. 11: 1213-1221 (2007).
Veber, D. F., et al., "Conformationally restricted bicyclic analogs of somatostatin", *Proc. Natl. Acad. Sci. USA*, vol. 75, No. 6: 2636-2640 (1978).
Venter, J. C., et al., "The Sequence of the Human Genome", *Science*, vol. 291: 1304-1531 (2001).
Verrijdt, G., et al., "Change of Specificity Mutations in Androgen-selective Enhancers", *The Journal of Biological Chemistry*, vol. 275, No. 16: 12298-12305 (2000).
Winter, G., et al., "Making Antibodies by Phage Display Technology", *Annual Rev. Immunol.*, vol. 12: 433-455 (1994).
Zola, H., "Using Monoclonal Antibodies: Soluble Antigens", in *Monoclonal Antibodies: A Manual of Techniques*: 147-181 (1987).
Zola, H. and Brooks, D., "Techniques for the Production and Characterization of Monoclonal Hybridoma Antibodies", in *Monoclonal Hybridoma Antibodies: Techniques and Applications*, Chapter 1, Edited by Hurrell, J. G. R, Chapter 1: 4-57 (1982).
Advisory Action for U.S. Appl. No. 14/355,698, dated Sep. 16, 2016.
Advisory Action for U.S. Appl. No. 14/355,698, dated Mar. 12, 2018.
Ailawardi, R.K., et al., "Treatment of endometriosis and chronic pelvic pain with letrozole and norethindrone acetate: a pilot study," Fertility and Sterility, 81(2): 290-296 (Feb. 2004).
Becker, C.M., et al., "Circulating Endothelial Progenitor Cells Are Up-Regulated in a Mouse Model of Endometriosis," Am J Pathol, 178(4): 1782-1791 (Apr. 2011).
Bladder Cancer WebMD, "Bladder Cancer—Prevention," downloaded from Internet URL: http://www.webmd.com/cancer/bladder-cancer/bladder-cancer-prevention [Downloaded May 15, 2015].
Cervical Cancer America Cancer Society, "Can Cervical Cancer be Prevented?," downloaded from Internet URL: http://www.cancer.org/cancer/cervicalcancer/moreinformation/cervicalcancer... [Downloaded Jun. 15, 2015].
D'Cruz, O.J. and Uckun, F.M., "Targeting Mast Cells in Endometriosis with Janus Kinase 3 Inhibitor, JANEX-1," Am J Reproductive Immunology, 58(2): 75-97 (2007).
Endometrial Cancer American Cancer Society, "Can Endometrial Cancer be Prevented?," downloaded from Internet URL: http://www.cancer.org/cancer/endometrialcancer/detailedguide/endometrial-uterine... [Downloaded Jun. 15, 2015].
Endometriosis WebMD, "Endometriosis—Prevention," downloaded from Internet URL: http://www.webmd.com/women/endometriosis/endometriosis-prevention [Downloaded Jun. 15, 2015].
Final Office Action for U.S. Appl. No. 14/355,698, dated Jun. 29, 2016.
Final Office Action for U.S. Appl. No. 14/355,698, dated Nov. 15, 2017.
Frackiewicz, E.J., "Endometriosis: An Overview of the Disease and Its Treatment," J. Am. Pharm. Assoc., vol. 40; No. 5; 21 pages (2000).
Healthline, "What are Ovarian Cysts?," downloaded from Internet URL: http://www.healthline.com/health/ovarian-cysts [Downloaded Jun. 15, 2015].
Ho, C.K.M. and Habib, F.K., "Estrogen and androgen signaling in the pathogenesis of BPH," Nature Reviews, vol. 8; 29-41 (2011).
International Search Report and Written Opinion for Int'l Application No. PCT/GB2012/052722, entitled: "Medical Use," dated Jun. 28, 2013.
Interview Summary for U.S. Appl. No. 14/355,698, dated Oct. 25, 2016.
Interview Summary for U.S. Appl. No. 14/355,698, dated Mar. 30, 2017.
Interview Summary for U.S. Appl. No. 14/355,698, dated Feb. 27, 2018.
Kistner, R.W., "Conservative Management of Endometriosis", Lancet: 79(5): 179-183 (May 1959).
Kistner, R.W., "The Use of Newer Progestins in The Treatment of Endometriosis*," Obstet. Gynecol., 75: 264-278 (1958).
Kumagami, A., et al., "Expression patterns of the steroid receptor coactivator family in human ovarian endometriosis," Journal of Obstet. Gynaecol. Res., vol. 37; No. 10; 1269-1276 (2011).
Longo, M. et al., "Interaction of estrogen receptor a with protein kinase C α and c-Src in osteoblasts during differenhation," Bone, 34: 100-111 (2004).
Lowe, C., et al., "Osteopetrosis in Src-deficient mice is due to an autonomous defect of osteoclasts," Proc. Natl. Acad. Sci. USA, 90: 4485-4489 (May 1993).
Matsuzaki, S., et al., "Effects of a protein kinase C inhibitor on the initial development of ectopic implants in a syngeneic mouse model of endometriosis," Fertility and Sterility, 89(1): 206-211, (Jan. 2008).
Nairn, Ph.D., J.G., "Solutions, Emulsions, Suspension and Extractives", Chapter 84, In Remington's Pharmaceutical Sciences 17th Edition, A.R. Gennaro, ed. (PA: Mack Publishing Company), pp. 1492-1661 (1985).

(56) References Cited

OTHER PUBLICATIONS

Ngô, C., et al., "Protein kinase inhibitors can control the progression of endometriosis in vitro and in vivo," J Pathol, 222: 148-157 (2010).
Notice of Allowance for U.S. Appl. No. 14/355,698, dated Mar. 28, 2018.
Office Action for U.S. Appl. No. 14/355,698, dated Aug. 28, 2015.
Office Action for U.S. Appl. No. 14/355,698, dated May 18, 2017.
OuYang, Z., et al., "Interleukin-4 Stimulates Proliferation of Endometriotic Stromal Cells," Am J Pathology, 173(2): 463-469 (Aug. 2008).
Ovarian Cancer WebMD, "Prevention," downloaded from Internet URL: http://www.webmd.com/ovarian-cancer/guide/ovarian-cancer-prevention [Downloaded Jun. 15, 2015].
Prostate Cencer American Cancer Society, "Can Prostate Cancer be Prevented?," downloaded from Internet URL: http://www.cancer.org/cancer/prostatecancer/detailedguide/prostate-cancer . . . [Downloaded Jun. 15, 2015].
Schweppe, K.-W. and Hummelshoj, L., "Recommendations on the use of GnRH in the management of endometriosis," In GnRH Analogs in Human Reproduction, B. Lunenfeld, ed., (UK: Francis & Taylor), pp. 53-66 (2005).
Sonmezer, M. and Oktay, K., "Fertility Preservation in Young Women Undergoing Breast Cancer Therapy," The Oncologist, vol. 11; 422-434 (2006).
Utah Department of Health, "Can Testicular Cancer be Prevented?," downloaded from Internet URL: http://www.ucan.cc/Cancer%20Education/Testicular_Cancer_FAQ/can-testicular-cancer . . . [Downloaded Jun. 15, 2015].
Vercellini, P., et al., "Continuous use of an oral contraceptive for endometriosis-associated recurrent dysmenorrhea that does not respond to a cyclic pill regimen," Fertil Steril, 80(3): 560-563 (Sep. 2003).
Walker, W.H., "Testosterone signaling and the regulation of spermatogenesis," Spermatogenesis, vol. 1; No. 2; 116-129 (2011).
Walsh, L., ed., "A Novel Way to Model Endometriosis," Research Horizons, Issue 8:34, University of Cambridge (Spring 2009).
Wikipedia,"Nuclear receptor coactivator 1", [online], [retrieved on Oct. 30, 2013]. Retrieved from the Internet URL: http://en.wikipedia.org/wiki/Nuclear_receptor_coactivator_1.
Yoshino, O., et al., "FR 167653, a p38 mitogen-activated protein kinase inhibitor, suppresses the development of endometriosis in a murine model," J Repro Immunology, 72: 85-93 (2006).
Zhou, W.-D., et al., "SB203580, a p38 mitogen-activated protein kinase inhibitor, suppresses the development of endometriosis by down-regulating proinflammatory cytokines and proteolytic factors in a mouse model," Human Reproduction, 25(12): 3110-3116 (2010).

\* cited by examiner

FIGURE 3
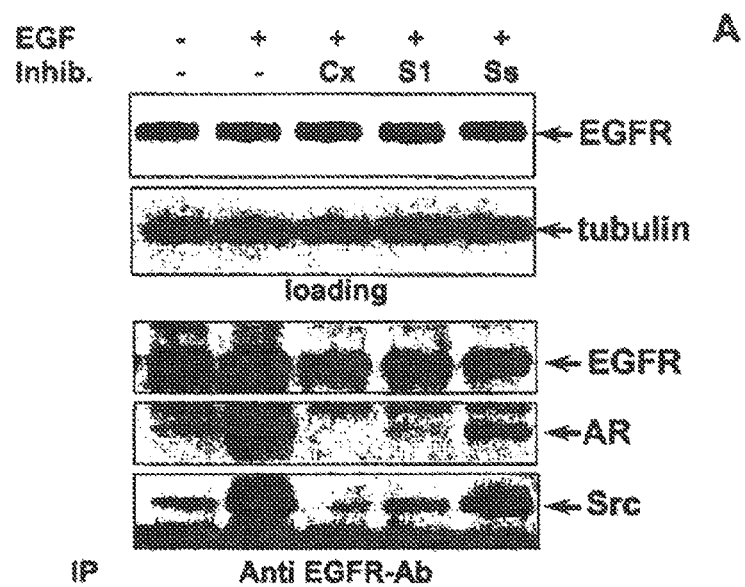
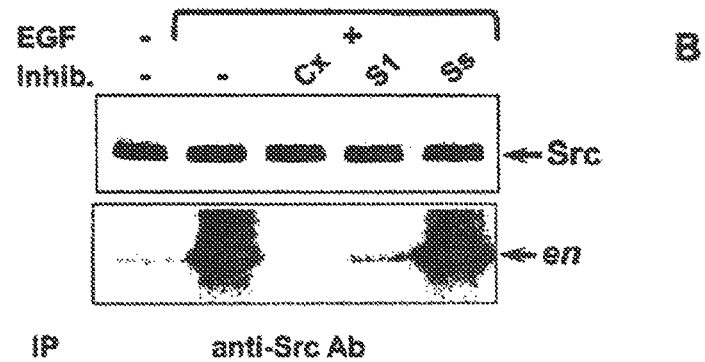
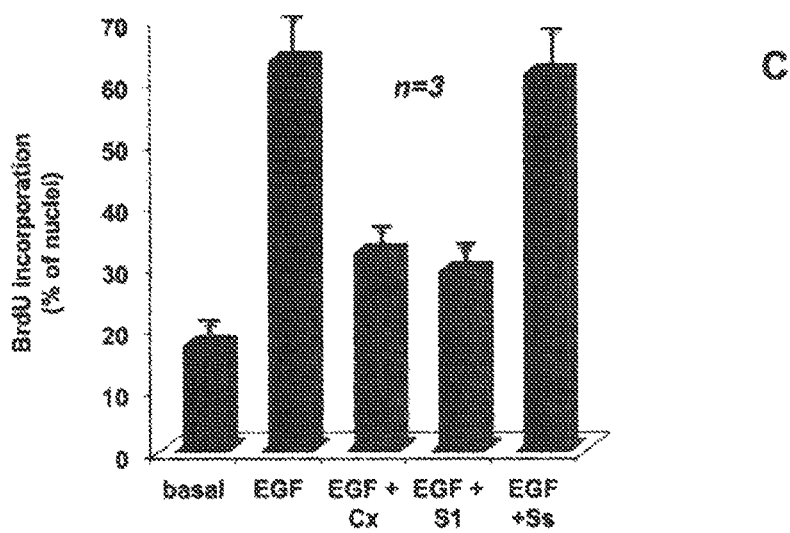

FIGURE 11A

Sequence Homology data - Androgen Receptor, Dihydro-testosterone receptor, Nuclear receptor family 3 group C member 4

[Sus scrofa (Pig)]
 896 AA
Score = 36.7 bits (79), Expect = 0.31
Identities = 10/10 (100%), Positives = 10/10 (100%)
query: 1	PPPHPHARIK 10 (SEQ ID. NO.: 21)
		PPPHPHARIK
Sbjct: 369	PPPHPHARIK 378 (SEQ ID. NO.: 27)

[Papio hamadryas (Hamadryas baboon)]
 895 AA
Score = 36.7 bits (79), Expect = 0.31
Identities = 10/10 (100%), Positives = 10/10 (100%)
query: 1	PPPHPHARIK 10 (SEQ ID. NO.: 21)
		PPPHPHARIK
Sbjct: 362	PPPHPHARIK 371 (SEQ ID. NO.: 28)

[Pan troglodytes (Chimpanzee)]
 911 AA
Score = 36.7 bits (79), Expect = 0.31
Identities = 10/10 (100%), Positives = 10/10 (100%)
query: 1	PPPHPHARIK 10 (SEQ ID. NO.: 21)
		PPPHPHARIK
Sbjct: 376	PPPHPHARIK 385 (SEQ ID. NO.: 29)

[Macaca mulatta (Rhesus macaque)]
895 AA
Score = 36.7 bits (79), Expect = 0.31
Identities = 10/10 (100%), Positives = 10/10 (100%)
query: 1	PPPHPHARIK 10 (SEQ ID. NO.: 21)
		PPPHPHARIK
Sbjct: 362	PPPHPHARIK 371 (SEQ ID. NO.: 30)

[Cynomolgus monkey)]
895 AA
Score = 36.7 bits (79), Expect = 0.31
Identities = 10/10 (100%), Positives = 10/10 (100%)
query: 1	PPPHPHARIK 10 (SEQ ID. NO.: 21)
		PPPHPHARIK
Sbjct: 362	PPPHPHARIK 371 (SEQ ID. NO.: 31)

FIGURE 11B

[Homo sapiens (Human)]
919 AA
Score = 36.7 bits (79), Expect = 0.31
Identities = 10/10 (100%), Positives = 10/10 (100%)
query: 1          PPPHPHARIK 10 (SEQ ID. NO.: 21)
                  PPPHPHARIK
Sbjct: 377        PPPHPHARIK 386 (SEQ ID. NO.: 21)

[(Red squirrel)]
458 AA
Score = 36.7 bits (79), Expect = 0.31
Identities = 10/10 (100%), Positives = 10/10 (100%)
query: 1          PPPHPHARIK 10 (SEQ ID. NO.: 21)
                  PPPHPHARIK
Sbjct: 333        PPPHPHARIK 342 (SEQ ID. NO.: 32)

[Felis catus (Cat) (Felis silvestris catus)]
475 AA
Score = 36.7 bits (79), Expect = 0.31
Identities = 10/10 (100%), Positives = 10/10 (100%)
query: 1          PPPHPHARIK 10 (SEQ ID. NO.: 21)
                  PPPHPHARIK
Sbjct: 355        PPPHPHARIK 364 (SEQ ID. NO.: 33)

[Galidia elegans (Malagasy ring-tailed mongoose)]
480 AA
Score = 36.7 bits (79), Expect = 0.31
Identities = 10/10 (100%), Positives = 10/10 (100%)
query: 1          PPPHPHARIK 10 (SEQ ID. NO.: 21)
                  PPPHPHARIK
Sbjct: 357        PPPHPHARIK 366 (SEQ ID. NO.: 34)

[Eupleres goudotii (falanouc)]
475 AA
Score = 36.7 bits (79), Expect = 0.31
Identities = 10/10 (100%), Positives = 10/10 (100%)
query: 1          PPPHPHARIK 10 (SEQ ID. NO.: 21)
                  PPPHPHARIK
Sbjct: 350        PPPHPHARIK 359 (SEQ ID. NO.: 35)

[Fossa fossana (Malagasy civet) (Striped civet)]
477 AA
Score = 36.7 bits (79), Expect = 0.31
Identities = 10/10 (100%), Positives = 10/10 (100%)
query: 1          PPPHPHARIK 10 (SEQ ID. NO.: 21)
                  PPPHPHARIK
Sbjct: 352        PPPHPHARIK 361 (SEQ ID. NO.: 36)

FIGURE 11C

[Viverricula indica (Small Indian civet)]
474 AA
Score = 36.7 bits (79), Expect = 0.31
Identities = 10/10 (100%), Positives = 10/10 (100%)
query: 1          PPPHPHARIK 10 (SEQ ID. NO.: 21)
                 PPPHPHARIK
Sbjct: 349        PPPHPHARIK 358 (SEQ ID. NO.: 37)

[Diceros bicornis (Black rhinoceros)]
461 AA
Score = 36.7 bits (79), Expect = 0.31
Identities = 10/10 (100%), Positives = 10/10 (100%)
query: 1          PPPHPHARIK 10 (SEQ ID. NO.: 21)
                 PPPHPHARIK
Sbjct: 337        PPPHPHARIK 346 (SEQ ID. NO.: 38)

[Equus caballus (Horse)]
 456 AA
Score = 36.7 bits (79), Expect = 0.31
Identities = 10/10 (100%), Positives = 10/10 (100%)
query: 1          PPPHPHARIK 10 (SEQ ID. NO.: 21)
                 PPPHPHARIK
Sbjct: 332        PPPHPHARIK 341 (SEQ ID. NO.: 39)
ExPASy BLAST2 Interface 28/01/2010 18:11
http://www.expasy.ch/cgi-bin/blast.pl#A1 Page 8 of 15
Androgen receptor (Fragment)
[ar]
[Lama guanicoe pacos (Alpaca) (Lama pacos)]
467 AA
Score = 36.7 bits (79), Expect = 0.31
Identities = 10/10 (100%), Positives = 10/10 (100%)
query: 1          PPPHPHARIK 10 (SEQ ID. NO.: 21)
                 PPPHPHARIK
Sbjct: 342        PPPHPHARIK 351 (SEQ ID. NO.: 40)

[Physeter catodon (sperm whale) (Physeter macrocephalus)]
 462 AA
Score = 36.7 bits (79), Expect = 0.31
Identities = 10/10 (100%), Positives = 10/10 (100%)
query: 1          PPPHPHARIK 10 (SEQ ID. NO.: 21)
                 PPPHPHARIK
Sbjct: 342        PPPHPHARIK 351 (SEQ ID. NO.: 41)

FIGURE 11D

[trichechus manatus (Caribbeanmanatee) (West Indian manatee)]
488 AA
Score = 36.7 bits (79), Expect = 0.31
Identities = 10/10 (100%), Positives = 10/10 (100%)
query: 1          PPPHPHARIK 10 (SEQ ID. NO.: 21)
              PPPHPHARIK
Sbjct: 362     PPPHPHARIK 371 (SEQ ID. NO.: 42)

[Elephas maximus (Indian elephant)]
469 AA
Score = 36.7 bits (79), Expect = 0.31
Identities = 10/10 (100%), Positives = 10/10 (100%)
query: 1          PPPHPHARIK 10 (SEQ ID. NO.: 21)
              PPPHPHARIK
Sbjct: 344     PPPHPHARIK 353 (SEQ ID. NO.: 43)

[Oryctolagus cuniculus (Rabbit)]
475 AA
Score = 36.7 bits (79), Expect = 0.31
Identities = 10/10 (100%), Positives = 10/10 (100%)
query: 1          PPPHPHARIK 10 (SEQ ID. NO.: 21)
              PPPHPHARIK
Sbjct: 350     PPPHPHARIK 359 (SEQ ID. NO.: 44)

[Lepus crawshayi]
460 AA
Score = 36.7 bits (79), Expect = 0.31
Identities = 10/10 (100%), Positives = 10/10 (100%)
query: 1          PPPHPHARIK 10 (SEQ ID. NO.: 21)
              PPPHPHARIK
Sbjct: 341     PPPHPHARIK 350 (SEQ ID. NO.: 45)

[Tarsius bancanus (Westerntarsier) (Horsfield's tarsier)]
461 AA
Score = 36.7 bits (79), Expect = 0.31
Identities = 10/10 (100%), Positives = 10/10 (100%)
query: 1          PPPHPHARIK 10 (SEQ ID. NO.: 21)
              PPPHPHARIK
Sbjct: 336     PPPHPHARIK 345 (SEQ ID. NO.: 46)

[Cynopterus sphinx (Indian short-nosed fruit bat)]
479 AA
Score = 36.7 bits (79), Expect = 0.31
Identities = 10/10 (100%), Positives = 10/10 (100%)
query: 1          PPPHPHARIK 10 (SEQ ID. NO.: 21)
              PPPHPHARIK
Sbjct: 354     PPPHPHARIK 363 (SEQ ID. NO.: 47)

FIGURE 11E

[Tupaia tana (Large tree shrew)]
470 AA
Score = 36.7 bits (79), Expect = 0.31
Identities = 10/10 (100%), Positives = 10/10 (100%)
query: 1          PPPHPHARIK 10 (SEQ ID. NO.: 21)
                  PPPHPHARIK
Sbjct: 358        PPPHPHARIK 367 (SEQ ID. NO.: 48)

[Saimiri boliviensis (Bolivian squirrel monkey)]
918 AA
Score = 36.7 bits (79), Expect = 0.31
Identities = 10/10 (100%), Positives = 10/10 (100%)
query: 1          PPPHPHARIK 10 (SEQ ID. NO.: 21)
                  PPPHPHARIK
Sbjct: 373        PPPHPHARIK 382 (SEQ ID. NO.: 49)

[Homo sapiens (Human)]
906 AA
Score = 36.7 bits (79), Expect = 0.31
Identities = 10/10 (100%), Positives = 10/10 (100%)
query: 1          PPPHPHARIK 10 (SEQ ID. NO.: 21)
                  PPPHPHARIK
Sbjct: 372        PPPHPHARIK 381 (SEQ ID. NO.: 21)

[Homo sapiens (Human)]
539 AA
Score = 36.7 bits (79), Expect = 0.31
Identities = 10/10 (100%), Positives = 10/10 (100%)
query: 1          PPPHPHARIK 10 (SEQ ID. NO.: 21)
                  PPPHPHARIK
Sbjct: 379        PPPHPHARIK 388 (SEQ ID. NO.: 21)

[Homo sapiens (Human)]
544 AA
Score = 36.7 bits (79), Expect = 0.31
Identities = 10/10 (100%), Positives = 10/10 (100%)
query: 1          PPPHPHARIK 10 (SEQ ID. NO.: 21)
                  PPPHPHARIK
Sbjct: 383        PPPHPHARIK 392 (SEQ ID. NO.: 21)

[Homo sapiens (Human)]
542 AA
Score = 36.7 bits (79), Expect = 0.31
Identities = 10/10 (100%), Positives = 10/10 (100%)
query: 1          PPPHPHARIK 10 (SEQ ID. NO.: 21)
                  PPPHPHARIK
Sbjct: 382        PPPHPHARIK 391 (SEQ ID. NO.: 21)

FIGURE 11F

[Homo sapiens (Human)]
531 AA
Score = 36.7 bits (79), Expect = 0.31
Identities = 10/10 (100%), Positives = 10/10 (100%)
query: 1          PPPHPHARIK 10 (SEQ ID. NO.: 21)
                  PPPHPHARIK
Sbjct: 371        PPPHPHARIK 380 (SEQ ID. NO.: 21)

[Homo sapiens (Human)]
730 AA
Score = 36.7 bits (79), Expect = 0.31
Identities = 10/10 (100%), Positives = 10/10 (100%)
query: 1          PPPHPHARIK 10 (SEQ ID. NO.: 21)
                  PPPHPHARIK
Sbjct: 189        PPPHPHARIK 198 (SEQ ID. NO.: 21)

[Homo sapiens (Human)]
643 AA
Score = 36.7 bits (79), Expect = 0.31
Identities = 10/10 (100%), Positives = 10/10 (100%)
query: 1          PPPHPHARIK 10 (SEQ ID. NO.: 21)
                  PPPHPHARIK
Sbjct: 384        PPPHPHARIK 393 (SEQ ID. NO.: 21)

[Homo sapiens (Human)]
682 AA
Score = 36.7 bits (79), Expect = 0.31
Identities = 10/10 (100%), Positives = 10/10 (100%)
query: 1          PPPHPHARIK 10 (SEQ ID. NO.: 21)
                  PPPHPHARIK
Sbjct: 384        PPPHPHARIK 393 (SEQ ID. NO.: 21)

[Homo sapiens (Human)]
647 AA
Score = 36.7 bits (79), Expect = 0.31
Identities = 10/10 (100%), Positives = 10/10 (100%)
query: 1          PPPHPHARIK 10 (SEQ ID. NO.: 21)
                  PPPHPHARIK
Sbjct: 383        PPPHPHARIK 392 (SEQ ID. NO.: 21)

[Homo sapiens (Human)]
648 AA
Score = 36.7 bits (79), Expect = 0.31
Identities = 10/10 (100%), Positives = 10/10 (100%)
query: 1          PPPHPHARIK 10 (SEQ ID. NO.: 21)
                  PPPHPHARIK
Sbjct: 383        PPPHPHARIK 392 (SEQ ID. NO.: 21)

FIGURE 11G

[Homo sapiens (Human)]
645 AA
Score = 36.7 bits (79), Expect = 0.31
Identities = 10/10 (100%), Positives = 10/10 (100%)
query: 1        PPPHPHARIK 10 (SEQ ID. NO.: 21)
                PPPHPHARIK
Sbjct: 384      PPPHPHARIK 393 (SEQ ID. NO.: 21)

[Canis familiaris (Dog)]
907 AA
Score = 33.7 bits (72), Expect = 2.4
Identities = 9/10 (90%), Positives = 9/10 (90%)
query: 1        PPPHPHARIK 10 (SEQ ID. NO.: 21)
                PPPHPH RIK
Sbjct: 380      PPPHPH  (SEQ ID. NO.: 50)
TRIK 389

[Eulemur fulvus collaris (Collared brown lemur) (Eulemur collaris)]
884 AA
Score = 33.3 bits (71), Expect = 3.3
Identities = 9/9 (100%), Positives = 9/9 (100%)
query: 2        PPHPHARIK 10 (SEQ ID. NO.: 21)
                PPHPHARIK
Sbjct: 359      PPHPHARIK 367 (SEQ ID. NO.: 51)

[Lemur catta (Ring-tailed lemur)]
458 AA
Score = 33.3 bits (71), Expect = 3.3
Identities = 9/9 (100%), Positives = 9/9 (100%)
query: 2        PPHPHARIK 10 (SEQ ID. NO.: 21)
                PPHPHARIK
Sbjct: 335      PPHPHARIK 343 (SEQ ID. NO.: 52)

[Eulemur fulvus fulvus (Brown lemur)]
451 AA
Score = 33.3 bits (71), Expect = 3.3
Identities = 9/9 (100%), Positives = 9/9 (100%)
query: 2        PPHPHARIK 10 (SEQ ID. NO.: 21)
                PPHPHARIK
Sbjct: 335      PPHPHARIK 343 (SEQ ID. NO.: 53)

[Hapalemur simus (Greater bamboo lemur) (Prolemur simus)]
458 AA
Score = 33.3 bits (71), Expect = 3.3
Identities = 9/9 (100%), Positives = 9/9 (100%)
query: 2        PPHPHARIK 10 (SEQ ID. NO.: 21)
                PPHPHARIK
Sbjct: 335      PPHPHARIK 343 (SEQ ID. NO.: 54)

FIGURE 11H

[Lepilemur edwardsi(Milne-Edwards's sportive lemur)]
455 AA
Score = 33.3 bits (71), Expect = 3.3
Identities = 9/9 (100%), Positives = 9/9 (100%)
query: 2              PPHPHARIK 10 (SEQ ID. NO.: 21)
              PPHPHARIK
Sbjct: 332     PPHPHARIK 340 (SEQ ID. NO.: 55)

[Cheirogaleus medius (Fat-tailed dwarf lemur)]
462 AA
Score = 33.3 bits (71), Expect = 3.3
Identities = 9/9 (100%), Positives = 9/9 (100%)
query: 2              PPHPHARIK 10 (SEQ ID. NO.: 21)
              PPHPHARIK
Sbjct: 339     PPHPHARIK 347 (SEQ ID. NO.: 56)

[Daubentonia madagascariensis (Aye-aye)]
464 AA
Score = 33.3 bits (71), Expect = 3.3
Identities = 9/9 (100%), Positives = 9/9 (100%)
query: 2              PPHPHARIK 10 (SEQ ID. NO.: 21)
              PPHPHARIK
Sbjct: 333     PPHPHARIK 341 (SEQ ID. NO.: 57)

[Propithecus deckenii coronatus]
460 AA
Score = 33.3 bits (71), Expect = 3.3
Identities = 9/9 (100%), Positives = 9/9 (100%)
query: 2              PPHPHARIK 10 (SEQ ID. NO.: 21)
              PPHPHARIK
Sbjct: 337     PPHPHARIK 345 (SEQ ID. NO.: 58)
]
[Nycticebus coucang (Slow loris)]
472 AA
Score = 33.3 bits (71), Expect = 3.3
Identities = 9/9 (100%), Positives = 9/9 (100%)
query: 2              PPHPHARIK 10 (SEQ ID. NO.: 21)
              PPHPHARIK
Sbjct: 348     PPHPHARIK 356 (SEQ ID. NO.: 59)

[Cavia porcellus (Guinea pig)]
495 AA
Score = 32.9 bits (70), Expect = 4.4
Identities = 9/10 (90%), Positives = 10/10 (100%)
query: 1              PPPHPHARIK 10 (SEQ ID. NO.: 21)
              PPPHP+ARIK
Sbjct: 370     PPPHPNARIK 379 (SEQ ID. NO.: 60)

FIGURE 11I

[Rattus norvegicus (Rat)]
902 AA
Score = 32.5 bits (69), Expect = 5.9
Identities = 10/11 (90%), Positives = 10/11 (90%), Gaps = 1/11 (9%)
query: 1          PPP-HPHARIK 10 (SEQ ID. NO.: 21)
                  PPP HPHARIK
Sbjct: 374        PPPTHPHARIK 384 (SEQ ID. NO.: 61)

[Mus musculus (Mouse)]
899 AA
Score = 32.5 bits (69), Expect = 5.9
Identities = 10/11 (90%), Positives = 10/11 (90%), Gaps = 1/11 (9%)
query: 1          PPP-HPHARIK 10 (SEQ ID. NO.: 21)
                  PPP HPHARIK
Sbjct: 371        PPPTHPHARIK 381 (SEQ ID. NO.: 62)

[Crocuta crocuta (spotted hyena)]
912 AA
Score = 32.5 bits (69), Expect = 5.9
Identities = 9/10 (90%), Positives = 9/10 (90%)
query: 1          PPPHPHARIK 10 (SEQ ID. NO.: 21)
                  P PHPHARIK
Sbjct: 385        PPHPHARIK 394  (SEQ ID. NO.: 63)

[Eliurus sp. C24]
464 AA
Score = 32.5 bits (69), Expect = 5.9
Identities = 10/11 (90%), Positives = 10/11 (90%), Gaps = 1/11 (9%)
query: 1          PPP-HPHARIK 10 (SEQ ID. NO.: 21)
                  PPP HPHARIK
Sbjct: 342        PPPTHPHARIK 352 (SEQ ID. NO.: 64)

[Steatomys sp. Gautuni]
475 AA
Score = 32.5 bits (69), Expect = 5.9
Identities = 10/11 (90%), Positives = 10/11 (90%), Gaps = 1/11 (9%)
query: 1          PPP-HPHARIK 10 (SEQ ID. NO.: 21)
                  PPP HPHARIK
Sbjct: 349        PPPTHPHARIK 359 (SEQ ID. NO.: 65)

[Otomys angoniensis (Angoni vlei rat)]
463 AA
Score = 32.5 bits (69), Expect = 5.9
Identities = 10/11 (90%), Positives = 10/11 (90%), Gaps = 1/11 (9%)
query: 1          PPP-HPHARIK 10 (SEQ ID. NO.: 21)
                  PPP HPHARIK
Sbjct: 343        PPPTHPHARIK 353 (SEQ ID. NO.: 66)

FIGURE 11J

[Mus musculus (Mouse)]
899 AA
Score = 32.5 bits (69), Expect = 5.9
Identities = 10/11 (90%), Positives = 10/11 (90%), Gaps = 1/11 (9%)
query: 1             PPP-HPHARIK 10 (SEQ ID. NO.: 21)
                     PPP HPHARIK
Sbjct: 371     PPPTHPHARIK 381 (SEQ ID. NO.: 62)

[(Silky anteater)]
467 AA
Score = 32.5 bits (69), Expect = 5.9
Identities = 10/11 (90%), Positives = 10/11 (90%), Gaps = 1/11 (9%)
query: 1             PP-PHPHARIK 10 (SEQ ID. NO.: 21)
                     PP PHPHARIK
Sbjct: 338     PPHPHPHARIK 348 (SEQ ID. NO.: 67)

[Procavia capensis (Cape hyrax) (Rock dassie)]
490 AA
Score = 32.5 bits (69), Expect = 5.9
Identities = 10/11 (90%), Positives = 10/11 (90%), Gaps = 1/11 (9%)
query: 1 PPP-HPHARIK 10 (SEQ ID. NO.: 21)
PPP HPHARIK
Sbjct: 363 PPPLHPHARIK 373 (SEQ ID. NO.: 68)

[Didelphis marsupialis virginiana (North American opossum)]
420 AA
Score = 32.5 bits (69), Expect = 5.9
Identities = 10/11 (90%), Positives = 10/11 (90%), Gaps = 1/11 (9%)
query: 1             PPP-HPHARIK 10 (SEQ ID. NO.: 21)
                     PPP HPHARIK
Sbjct: 391     PPPTHPHARIK 401 (SEQ ID. NO.: 69)

[Galeopterus variegatus (Malayan flying lemur) (Cynocephalus variegatus)]
453 AA
Score = 32.5 bits (69), Expect = 5.9
Identities = 10/11 (90%), Positives = 10/11 (90%), Gaps = 1/11 (9%)
query: 1             PPPH-PHARIK 10 (SEQ ID. NO.: 21)
                     PPPH PHARIK
Sbjct: 327     PPPHHPHARIK 337 (SEQ ID. NO.: 70)

MODULATORS OF THE SRC-KINASE ACTIVITY FOR PREVENTING OR TREATING METASTATIC CANCER

RELATED APPLICATIONS

This application is the U.S. National Stage of International Application No. PCT/GB2014/051347, filed Apr. 30, 2014, which designates the U.S., published in English, and claims priority under 35 U.S.C. §§ 119 or 365(c) to Great Britain Application No. 1307872.0, filed May 1, 2013.

INCORPORATION BY REFERENCE OF MATERIAL IN ASCII TEXT FILE

This application incorporates by reference the Sequence Listing contained in the following ASCII text file:
a) File name: 52541000001SubSeqListing.txt; created May 11, 2017, 14 KB in size.

BACKGROUND

The present invention relates to a medical use of molecules, and in particular the use of molecules to treat metastatic cancer, such as metastatic cancers in which an activity of the androgen receptor (AR) and/or estradiol receptor (ER) is a contributory factor.

The listing or discussion of an apparently prior-published document in this specification should not necessarily be taken as an acknowledgement that the document is part of the state of the art or is common general knowledge.

SUMMARY OF THE INVENTION

Metastasis is the spread of one or more cancerous cells from a primary site to one or more other sites in the body, usually by way of blood vessels or lymphatics. The new occurrences of disease thus generated are referred to as metastases. After the cancer cells come to rest at another site, they may re-penetrate the vessel or walls and continue to multiply, eventually forming another clinically detectable cancer. This new cancer is known as a metastatic (or secondary) cancer, and its cells are similar to those in the original primary cancer. This means, for example, that, if breast cancer metastasises to the lungs, the secondary cancer is made up of abnormal breast cells, not of abnormal lung cells. The cancer in the lung is then called metastatic breast cancer, not lung cancer.

Metastasis is a complex process comprising multiple steps. The metastatic process requires a cancer cell to acquire the ability to migrate through the primary tumour mass by increasing its cellular motility, intravasate and survive in blood or lymphatic vascular systems, and extravasate from the vascular system into a secondary tissue or organ to form metastatic nodules. During metastasis, cancer cells are involved in numerous interactions with the extracellular matrix (ECM); those proteins, growth factors and cytokines associated with the ECM; basement membranes; blood cells in the circulation; and the microenvironment of the secondary site where cancer cells eventually displace the normal tissue as they grow out and form metastatic foci. Several regulatory pathways are either altered or aberrantly expressed to render tumour cells the ability to successfully accomplish each or all of the steps of the metastatic process. As one example, matrix metalloproteinases (MMPs) are regarded as critical molecules in assisting cancer cells during metastasis.

Generally, metastasis in a cancer subject dramatically reduces the subject's likelihood of survival. Current treatment includes radiosurgery, chemotherapy, radiation therapy, biological therapy, hormone therapy, surgery or a combination of one or more of these interventions. The choice of treatment depends on a larger number of factors, including the type of primary cancer, the size and location of the metastases, the patient's age and general health, and the types of treatment used previously, among others. However, even with such a range of treatment regimes available, the current options are rarely able to cure metastatic cancer. Hence, there remains a pressing need for new and effective therapies to combat metastatic cancer.

Surprisingly and unexpectedly, the inventors have now demonstrated that targeting the SH3 domain of the tyrosine kinase, Src impairs the metastatic phenotype of fibrosarcoma and prostate cancer cells. The inventors have found that a peptide that binds to the SH3 domain of Src inhibits EGF-mediated processes known to be collectively involved in metastasis, such as DNA synthesis, motility and MMP secretion (see Example 1), and significantly reduces the incidence of lymph node metastases (see Example 2). Given that cell motility and MMP expression are known to be involved in metastasis (Jung et al, 2010; Cortes et al, 2008; Murray et al, 2012) the inventors believe that the effect will be apparent for other metastatic cancers also.

The SH3 domain of Src is known to mediate various protein interactions with Src, including, for example, its interaction with the androgen receptor (AR) and estrogen receptor (ER). The peptides used by the inventors, and described in the Examples, are known to disrupt complex formation between Src, AR and ER, which is a key component of AR and ER-associated Src signalling. The inventors therefore believe that other molecules which disrupt formation of this complex will have the same effect in those metastatic cancers wherein an activity of the AR and/or ER is a contributory factor.

Both the AR and estrogen receptor (ER) are known to interact with the tyrosine kinase Src and potentially other Src-family kinases. The AR receptor binds to the SH3 domain of Src (Migliaccio et al (Oncogene 2007, 26: 6619)). SH3 domains are 50-70 amino acids long and often feature in eukaryotic signal transduction and cytoskeletal proteins. The domains bind proline rich peptides and thereby play a major role in regulation of kinase activity as well as localisation and substrate recognition. The ER receptor binds to the SH2 domain of Src (Migliaccio et al (Cancer Research 2005, 65(22): 10585-93)). SH2 domains are generally around 100 amino acids long and typically bind to a phosphorylated tyrosine residue in the context of a longer peptide motif in a target protein. The inventors believe that targeting the ER/Src complex will work in the same way as targeting the AR/Src complex.

Without wishing to be bound by any theory, the inventors also believe that by reducing the interaction between a Src family kinase and either AR or ER, the non-genomic regulation of signal transduction by steroid hormones can be selectively inhibited (e.g. activation of a Src family kinase signalling, cyclin D1 expression and DNA synthesis), while at the same time the genomic regulation of signal transcription by steroid hormones is retained. In this way, many of the side effects associated with conventional steroid hormone blockade or ablation (which abolish both genomic and non-genomic effects) are avoided, and treatment can be more sustained. Furthermore, the inventors have found that reducing the interaction between a Src family kinase and either AR or ER is, surprisingly, without a contraceptive effect (see, for example, Example 3). Preservation of fertility represents a significant advancement in hormonal-mediated treatment since, currently, treatment with anti-androgens and/or anti-estrogens must be suspended to allow conception, which suspension can lead to disease recurrence.

Accordingly, a first aspect of the invention provides a molecule that modulates an activity of a Src family kinase for use in preventing or treating a metastatic cancer.

Similarly, the invention provides the use of a molecule that modulates an activity of a Src family kinase in the manufacture of a medicament for preventing or treating a metastatic cancer.

Similarly, the invention provides a method of preventing or treating a metastatic cancer, the method comprising administering a molecule that modulates an activity of a Src family kinase.

By "preventing or treating" a metastatic cancer we include the meaning that the invention can be used to alleviate symptoms of the disorder (i.e. palliative use), or to treat the disorder (e.g. by inhibition or elimination of the causative agent), or to prevent the disorder (i.e. prophylactic use—either preventing the symptoms from worsening or progressing, or reducing the progression of a disorder). We also include the meaning of reducing metastatic progression of the cancer. The molecule may be used to prevent metastasis in a subject that is known to have a primary cancer, or else reduce metastasis in that subject (eg the number of metastases that develop in that subject and/or the rate at which metastases develop in that subject).

Preferably, the metastatic cancer (eg one in which an activity of AR and/or ER is a contributory factor in a subject) is prevented or treated in a mammalian subject such as a human. Alternatively, the subject may be an animal, for example a domesticated animal (for example a dog or cat), laboratory animal (for example laboratory rodent, mouse, rat or rabbit) or an animal important in agriculture (i.e. livestock), for example, cattle, sheep, horses or goats. The subject may be female or male.

In an embodiment, the molecule that modulates an activity of a Src family kinase is one that inhibits or prevents an interaction between a Src family kinase and an androgen receptor (AR) or estradiol receptor (ER). In this instance, the metastatic cancer is preferably one in which an activity of AR and/or ER is a contributory factor.

Thus, the invention provides a molecule that inhibits or prevents an interaction between a Src family kinase and an androgen receptor (AR) or estradiol receptor (ER) for use in preventing or treating a metastatic cancer in which an activity of AR and/or ER is a contributory factor. Similarly, the invention provides the use of a molecule that inhibits or prevents an interaction between a Src family kinase and an androgen receptor (AR) or estradiol receptor (ER) in the manufacture of a medicament for preventing or treating a metastatic cancer in which an activity of AR and/or ER is a contributory factor. Similarly, the invention provides a method of preventing or treating a metastatic cancer in which an activity of AR and/or ER is a contributory factor, the method comprising administering to the subject in need thereof an effective amount of a molecule that inhibits or prevents an interaction between a Src family kinase and an androgen receptor (AR) or estradiol receptor (ER).

By a Src family kinase we include any kinase of the Src family. For example, the kinase may be any non-tyrosine kinase selected from Src, Yes, Fyn and Fgr (i.e. a kinase of the SrcA subfamily), Lck, Hck, Blk, and Lyn (i.e. a kinase of the SrcB subfamily) and Frk (Amanchy et al, Proteome Res 2008, 7(8): 3447). Most preferably, the Src family kinase is Src kinase.

By a Src family kinase we include the meaning of a human Src family kinase such as human Src kinase, by androgen receptor (AR) we include the meaning of human AR, and by estradiol receptor (ER) we include the meaning of human ER, the sequences of all of which are provided in Migliaccio et al (Cancer Research 2005, 65(22): 10585-93), Migliaccio et al (Oncogene 2007, 26: 6619), Venter et al (Science 2001, 291(5507):1304-51) and WO 2008/113770. It will be appreciated that there is natural variability with respect to the gene and mRNA sequences, and such variability is included within the meaning of each of a Src family kinase (e.g. Src kinase), AR and ER as herein defined.

Variants of human Src family kinase (e.g. Src kinase), AR and/or ER are also included provided that they share one or more activities of the parent Src family kinase (e.g. Src kinase), AR or ER. In other words, the variants are functional variants. For example, the variants may share at least 60% sequence identity, for example at least 65%, 70%, 75%, 80% and 85% sequence identity and more preferably 90%, 95% or 99% sequence identity with the corresponding human sequence. Variations include insertions, deletions and substitutions, either conservative or non-conservative. By "conservative substitutions" is intended combinations such as Gly, Ala; Val, Ile, Leu; Asp, Glu; Asn, Gln; Ser, Thr; Lys, Arg; and Phe, Tyr.

By each of a Src family kinase (e.g. Src kinase), AR and ER, we also include orthologues of human Src family kinase (e.g. Src kinase), AR and ER. Examples of suitable homologous Src family kinases, AR and ER include those from mice and rats. Other orthologues include those from the species listed in FIG. 11. It will be appreciated that there is natural variability with respect to the gene and mRNA sequences encoding the orthologues of each of human Src family kinase, AR and ER, and that this variability is included within the meaning of a homologous Src family kinase, AR and ER as defined.

In an embodiment of the molecule that inhibits or prevents an interaction between Src family kinase and an AR or ER, the molecule is one that inhibits or prevents an interaction between the SH3 domain of a Src family kinase (e.g. Src kinase) and an androgen receptor. The details of this interaction are provided in Migliaccio et al (Oncogene 2007, 26: 6619). Thus, the molecule may be one that binds to the SH3 domain of a Src family kinase.

By the 'SH3 domain' of a Src family kinase we include the meaning of the N-terminal Src homology-3 domain of a Src family kinase (e.g. Src kinase). SH3 domains are typically 50-70 amino acids long and bind proline rich peptides. Work by Migliaccio et al (EMBO J 2000, 19: 5406-5417) has demonstrated the importance of the SH3 domain of Src kinase in its interaction with AR.

In another embodiment of the molecule that inhibits or prevents an interaction between Src family kinase and an AR or ER, the molecule is one that inhibits or prevents an interaction between the SH2 domain of a Src family kinase (e.g. Src kinase) and an estradiol receptor. The details of this interaction are provided in Migliaccio et al (Cancer Research 2005, 65(22):10585-93).

By the 'SH2 domain' of a Src family kinase we include the meaning of the Src homology-2 domain of a Src family kinase (e.g. Src kinase). SH2 domains are generally around 100 amino acids in length and typically bind to phosphorylated tyrosine residues.

By a molecule that prevents or inhibits the interaction between a Src family kinase and AR or ER, we include both the meaning of prohibiting an interaction from forming in the first place and reducing an interaction once it has been formed. Preferably, the molecule prohibits or reduces the interaction to an undetectable level.

Preferably, the molecule that prevents or inhibits the interaction between a Src family kinase (e.g. Src kinase) and AR or ER, does so selectively. For example, it is preferred if the molecule prevents or inhibits an interaction between a Src family kinase and AR or ER to a greater extent (e.g. at least 5 fold, 10 fold, 20 fold, 50 fold, 100 fold or 1000 fold) than it prevents interactions between a Src family kinase and any other molecule. Likewise, it is preferred if the molecule prevents or inhibits an interaction between AR or ER, and a Src family kinase to a greater extent (e.g. at least 5 fold, 10 fold, 20 fold, 50 fold, 100 fold or 1000 fold) than it prevents the interactions between AR or ER, and any other molecule.

Whether or not a molecule prevents or inhibits the interaction between a Src family kinase and AR or ER, is conveniently determined by assessing the interaction between a Src family kinase and either AR or ER, in the presence and absence of the particular molecule. As mentioned above, the SH3 domain of Src kinase is believed to mediate an interaction between Src kinase and AR, and so the interaction between the SH3 domain of a Src family kinase (e.g. Src kinase) and AR may be assessed in the presence and absence of the particular molecule. Similarly, the SH2 domain of Src kinase is believed to mediate an interaction between Src kinase and ER, and so the interaction between the SH2 domain of a Src family kinase (e.g. Src kinase) and ER may be assessed in the presence and absence of the particular molecule. Methods for assessing the interaction between two proteins are well known in the art and any suitable method may be used. Examples include enzyme linked immunosorbent assays (ELISA), surface plasmon resonance assays, competition assays, chip-based assays, immunocytofluorescence, yeast two-hybrid technology and phage display, all of which are common practice in the art and are described, for example, in Plant et al (1995) Analyt Biochem, 226(2), 342-348. and Sambrook et al (2001) Molecular Cloning A Laboratory Manual. Third Edition. Cold Spring Harbor Laboratory Press, Cold Spring Harbor, N.Y. Other methods of assessing protein interactions include ultrafiltration with ion spray mass spectroscopy/HPLC methods or other physical and analytical methods. Fluorescence Energy Resonance Transfer (FRET) methods, for example, are well known to those skilled in the art, may be used, in which binding of two fluorescent labelled entities may be measured by measuring the interaction of the fluorescent labels when in close proximity to each other. In a particularly preferred embodiment, an immunoprecipitation assay such as that described in Migliaccio et al (Oncogene 2007, 26: 6619) is used to assess the interaction between the SH3 domain of a Src family kinase (e.g. Src kinase) and AR, and/or the interaction between the SH2 domain of a Src family kinase (e.g. Src kinase) and ER.

In another embodiment, the molecule that modulates an activity of a Src family kinase is one that binds to the SH3 domain of a Src family kinase.

As mentioned above, SH3 domains of Src family kinases are well known in the art and are readily identifiable by the skilled person. The domains may be identified by protein sequence alignment, by interrogating protein databases (eg UNIPROT) or by using commercially available computer algorithms to predict their location. In human Src, the SH3 domain spans from amino acid position 7-90.

Assessing binding of molecules to the SH3 domain of Src family kinase is standard practice in the art, and any of the techniques aimed at assessing protein interactions described above may be used.

Preferably, the molecule that binds to the SH3 domain of a Src family kinase, does so selectively. For example, it is preferred if the molecule binds to the SH3 domain of a Src family kinase to a greater extent (e.g. at least 5 fold, 10 fold, 20 fold, 50 fold, 100 fold or 1000 fold) than it binds to any other domain of the Src family kinase. Similarly, it is preferred if the molecule binds to the SH3 domain of the Src family kinase to a greater extent (e.g. at least 5 fold, 10 fold, 20 fold, 50 fold, 100 fold or 1000 fold) than it binds to a SH3 domain of any other protein.

With respect to the mammalian subject which is to be treated, it is appreciated that the molecule is one which that can modulate an activity of a Src family kinase (eg inhibit or prevent the interaction between a Src family kinase and AR or ER) of that mammalian species. For example, when the mammalian subject is a human, the molecule can modulate an activity of a human Src family kinase (eg inhibit or prevent the interaction between a human Src family kinase (e.g. Src kinase) and either human AR or human ER), and so on.

In a preferred embodiment of the first aspect of the invention, the molecule is one that comprises or consists of the structure:

$B_j$-[(Pro)$_n$-X$_r$-His-Pro-His-Ala-Arg-Ile-Lys]$_m$-R$_p$, (SEQ ID. NO.: 1) or $B_j$-[lys-ile-arg-ala-his-pro-his-x$_r$-(pro)$_n$]$_m$-R$_p$ (SEQ ID. NO.: 2), or a derivative or fragment thereof, wherein B is a first chemical moiety, j is 0 or 1, n is an integer from 1-10, X is any amino acid, r is an integer from 0 to 2, m is an integer from 1 to 3, R is a second chemical moiety, p is 0 or 1, and [lys-ile-arg-ala-his-pro-his-x$_r$-(pro)$_n$] (SEQ ID. NO.: 2) is the retro-inverso peptide of [(Pro)$_n$-X$_r$-His-Pro-His-Ala-Arg-Ile-Lys] (SEQ ID. NO.: 1).

It will be understood that the molecule that comprises or consists of the structure $B_j$-[(Pro)$_n$-X$_r$-His-Pro-His-Ala-Arg-Ile-Lys]$_m$-R$_p$, (SEQ ID. NO.: 1) or $B_j$-[lys-ile-arg-ala-his-pro-his-x$_r$-(pro)$_n$]$_m$-R$_p$ (SEQ ID. NO.: 2) generally has a peptide portion [(Pro)$_n$-X$_r$-His-Pro-His-Ala-Arg-Ile-Lys]$_m$ (SEQ ID. NO.: 1) or [lys-ile-arg-ala-his-pro-his-x$_r$-(pro)$_n$]$_m$ (SEQ ID. NO.: 2), and optionally further chemical moieties at one or both termini (i.e. $B_j$ and $R_p$). In other words, j=0 and p=0; or j=1 and p=0; or j=0 and p=1; or j=1 and p=1. In an embodiment, j=0 and p=0 such that the molecule is a peptide with the structure [(Pro)$_n$-X$_r$-His-Pro-His-Ala-Arg-Ile-Lys]$_m$ (SEQ ID. NO.: 1) or [lys-ile-arg-ala-his-pro-his-x$_r$-(pro)$_n$]$_m$ (SEQ ID. NO.: 2).

B and R may be independently, any chemical moiety such as any of a lipid (e.g. a glycolipid, phospholipid, sphingolipid), a fatty acid, a triglyceride, glycerol, a prenyl or iso-prenyl moiety (e.g. farnesyl or geranyl geranyl moieties), a carbohydrate (e.g. mono- and poly-saccharides), an amino acid, a peptide, a polypeptide or a nucleic acid, or a combination thereof. Thus, the moiety may be a glycopeptides or a lipo-peptide. The moiety may be a low or high molecular weight polyethylene glycol, for example with a molecular weight ranging from 200-70000. Any additional suitable moiety may be determined by a skilled person.

In an embodiment, B is any of H, or an acetyl group, or one or a sequence of amino acids provided with a free or acetyl-derivatised NH$_2$ group.

In a further embodiment, R is any of an OH group, or an NH$_2$ group or one or a sequence of amino acids with a C-terminal carboxy-amide group.

Chemical moieties B and R may be optionally attached to the peptide portion of the molecule such that they may be cleaved off the peptide portion when the molecule is administered to the subject. For example, either of moieties B and R may comprise a cleavage site that is capable of being cleaved when the molecule is administered to the body. Generally, the cleavage site is a protease cleavage site that is capable of being cleaved by a protease that resides in the subject.

Chemical moieties B and/or R may be joined to the peptide portion by any suitable method known in the art. For example, moieties B and/or R may be joined to the peptide portion by any of the conventional ways of cross-linking polypeptides, such as those generally described in O'Sullivan et al *Anal. Biochem.* (1979) 100, 100-108. For example, the first portion may be enriched with thiol groups and the second portion reacted with a bifunctional agent capable of reacting with those thiol groups, for example the N-hydroxysuccinimide ester of iodoacetic acid (NHIA) or N-succinimidyl-3-(2-pyridyldithio)propionate (SPDP), a heterobifunctional cross-linking agent which incorporates a disulphide bridge between the conjugated species. Amide and thioether bonds, for example achieved with m-maleimidobenzoyl-N-hydroxysuccinimide ester, are generally more stable in vivo than disulphide bonds.

Further useful cross-linking agents include S-acetylthioglycolic acid N-hydroxysuccinimide ester (SATA) which is a thiolating reagent for primary amines which allows deprotection of the sulphydryl group under mild conditions (Julian et al (1983) *Anal. Biochem.* 132, 68), dimethylsuberimidate dihydrochloride and N,N'-o-phenylenedimaleimide.

Further ways of joining chemical moieties B and/or R to the peptide portion include a chemical ligation protocol, a protocol for coupling using click chemistry or by using a protocol for coupling using Staudinger ligation, which are well known in the art. Other suitable methods may be determined by the skilled person.

When chemical moieties B and/or R are peptides or polypeptides, it is appreciated that the peptide portion of the molecule and chemical moieties B and/or R may be part of a fusion polypeptide that may be encoded by a nucleic acid molecule. For example, chemical moiety B and/or R may be genetically engineered to contain the peptide portion of the molecule using genetic engineering techniques well established in the art.

Conveniently, the peptide portion [(Pro)$_n$-X$_r$-His-Pro-His-Ala-Arg-Ile-Lys]$_m$ (SEQ ID. NO.: 1) or [lys-ile-arg-ala-his-pro-his-x$_r$-(pro)$_n$]$_m$ (SEQ ID. NO.: 2) of the molecule is less than 57 amino acid residues in length, such as less than 55, 50, 45, 40, 35, 30, 25, 20 or 15 amino acids in length. Thus, the peptide portion may have a length of from 8 to 60 amino acid resides, or a length from 10 to 15 amino acid residues, or a length of from 15 to 20 amino acid residues, or a length of from 20 to 25 amino acid residues, or a length of from 25 to 30 amino acid residues, or a length of from 30 to 35 amino acid residues, or a length of from 35 to 40 amino acid residues, or a length of from 40 to 45 amino acid residues, or a length of from 45 to 50 amino acid residues, or a length of from 50 to 55 amino acid residues. Preferably, the peptide portion is 8, 9, 10, 11, 12, 13, 14, 15, 16, 17, 18, 19, 20, 21, 22, 23, 24 or 25 amino acids in length, and most preferably 10 amino acids in length.

It is understood that a fragment of the molecule comprising or consisting of the structure B$_j$-[(Pro)$_n$-X$_r$-His-Pro-His-Ala-Arg-Ile-Lys]$_m$-R$_p$ (SEQ ID. NO.: 1), or B$_j$-[lys-ile-arg-ala-his-pro-his-x$_r$-(pro)$_n$]$_m$-R$_p$ (SEQ ID. NO.: 2), may be used provided that it is capable of modulating an activity of a Src family kinase. For example, the fragment may be capable of preventing or inhibiting an interaction between a Src family kinase (e.g. Src kinase) and AR and/or ER, or the fragment may be capable of binding to the SH3 domain of the Src family kinase. Thus, it is possible that the molecule may contain fewer than the 8 amino acids mentioned above. Typically, the fragment is a fragment of the peptide portion [(Pro)$_n$-X$_r$-His-Pro-His-Ala-Arg-Ile-Lys]$_m$ (SEQ ID. NO.: 1) or [lys-ile-arg-ala-his-pro-his-x$_r$-(pro)$_n$]$_m$ (SEQ ID. NO.: 2) of the molecule, and generally is at least 3 amino acids in length, such as at least 4, 5, 6, 7, 8, 9, 10, 11, 12, 13, 14 or 15 amino acids in length. Thus, the molecule may comprise or consist of a fragment of the peptide [(Pro)$_n$-X$_r$-His-Pro-His-Ala-Arg-Ile-Lys]$_m$ (SEQ ID. NO.: 1) or [lys-ile-arg-ala-his-pro-his-x$_r$-(pro)$_n$]$_m$ (SEQ ID. NO.: 2) provided that it is capable of modulating an activity of a Src family kinase. (eg preventing or inhibiting an interaction between a Src family kinase (e.g. Src kinase) and AR and/or ER, or binding to the SH3 domain of a Src family kinase).

A derivative or salt of the fragment may be used as described further below. For example, capping moieties may be added to one or both ends of the fragment to improve stability.

Examples of suitable fragments may be selected from the group consisting of: HPHARIK (SEQ ID. NO.: 3), HPHAR (SEQ ID. NO.: 4), PHPHAR (SEQ ID. NO.: 5), HPH, PHPH (SEQ ID. NO.: 6), PPHPH (SEQ ID. NO.: 7), PPPHPH (SEQ ID. NO.: 8), PHP, PPHP (SEQ ID. NO.: 9), PPPHP (SEQ ID. NO.: 10), PPPH (SEQ ID. NO.: 11), PPH, and PPP. Particular derivatives or salts of the fragments may be selected from the group consisting of: Ac-HPHARIK-NH2 (SEQ ID. NO.: 12), Ac-HPHAR-NH2 (SEQ ID. NO.: 13), Ac-PHPHAR-NH2 (SEQ ID. NO.: 14), Ac-HPH-NH2, Ac-PHPH-NH2 (SEQ ID. NO.: 15), Ac-PPHPH-NH2 (SEQ ID. NO.: 16), Ac-PPPHPH-NH2 (SEQ ID. NO.: 17), Ac-PHP-NH2, Ac-PPHP-NH2 (SEQ ID. NO.: 18), Ac-PPPHP-NH2P (SEQ ID. NO.: 19), Ac-PPPH-NH2 (SEQ ID. NO.: 20), Ac-PPH-NH2 and Ac-PPP-NH2.

It is appreciated that when moieties B and/or R are peptides, the entire molecule may be a peptide and such a peptide may be more than 57 amino acids in length. However, if the entire molecule is a peptide, it is preferred if it is less than 150 amino acids in length, such as less than 140, 130, 120, 110, 100, 90, 80, 70 or 60 amino acids in length.

Generally, the molecule has a molecular weight of less than 50 kDa such as less than 40, 30, 20, 10 or 5 kDa. Typically, the molecule is between 1000 and 5000 Da in molecular weight. Thus, the molecule may be about 4500, 4000, 3500, 3000 or 2500 Da in molecular weight, or weigh between 1000 and 2500 Da in molecular weight.

In one embodiment, n is any of 1, 2, 3, 4, 5, 6, 7, 8, 9 or 10, and most preferably, n=3. In another embodiment, m is any of 1, 2 or 3, and most preferably, m=1. Thus, in a particularly preferred embodiment, n is 3 and m is 1.

X$_r$ represents a stretch of 1 or 2 amino acid residues which can, independently or both, be any amino acid residue. Thus, the amino acid residues represented by X$_r$ may be a any naturally occurring amino acid residue which is encoded by DNA, selected from alanine (Ala, A), arginine (Arg, R), asparagine (Asn, N), aspartic acid (Asp, D), cysteine (Cys, C), glutamine (Gln, Q), glutamic acid (Glu, E), glycine (Gly, G), histidine (His, H), isoleucine (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y) and valine (Val, V). However, other than when the peptide portion is made by expression from a polynucleotide, the amino acid residues represented by X$_r$ may comprise one or more amino acid residues which are not encoded by DNA, including those described below. In one embodiment r is 0 and in an alternative embodiment r is 1 and X is a threonine residue.

For the avoidance of doubt, the molecule is not AR or ER.

Without wishing to be bound by any theory, the inventor believes that the peptide PPPHPHARIK (SEQ ID. NO.: 21) is the portion of human AR that mediates the interaction with the SH3 domain of a Src family kinase. Thus, in a particularly preferred embodiment, the peptide portion [(Pro)$_n$-X$_r$-His-Pro-His-Ala-Arg-Ile-Lys]$_m$ (SEQ ID. NO.: 1) or [lys-ile-arg-ala-his-pro-his-x$_r$-(pro)$_n$]$_m$ (SEQ ID. NO.: 2) of the molecule is PPPHPHARIK (SEQ ID. NO.: 21) or the retro-inverso peptide thereof, kirahphppp (SEQ ID. NO.: 22).

The peptide PPPHPHARIK (SEQ ID. NO.: 21) is equivalent to amino acid residues 377-386 of human AR and, without wishing to be bound by any theory, it is believed by the inventor that the corresponding portions of AR from other species would share the same activity. By "corresponding portion" we include the meaning of the amino acid residue sequence in another AR which aligns to the given amino acid sequence in human AR when the human AR and the other AR are compared, for example by using an alignment tool such as MacVector or CLUSTALW. Thus, in another preferred embodiment, the peptide portion is a peptide that corresponds to the amino acid sequence at positions 377-386 (PPPHPHARIK) (SEQ ID. NO.: 21) of the human AR. For example, the corresponding peptide in mouse and rat AR is PPTHPHARIK (SEQ ID. NOs.: 23 and 25), and so the peptide portion may be PPTHPHARIK (SEQ ID. NOs.: 23 and 25) or the retro-inverso peptide thereof, kirahphtpp (SEQ ID. NOs.: 24 and 26). The corresponding peptides in a selection of other species are provided in FIG. 11, and so the peptide portion may be any of the peptides listed in FIG. 11 or the retro-inverso peptides thereof. Preferably, the peptide PPPHPHARIK (SEQ ID. NO.: 21) is administered to human subjects, and the peptide PPTH-PHARIK (SEQ ID. NOs.: 23 and 25) is administered to mouse or rat subjects, and so on.

Aligning two proteins may be carried out using the Clustal W program (Thompson et al., 1994). The parameters used may be as follows: Fast pairwise alignment parameters: K-tuple (word) size; 1, window size; 5, gap penalty; 3, number of top diagonals; 5. Scoring method: x percent. Multiple alignment parameters: gap open penalty; 10, gap extension penalty; 0.05. Scoring matrix: BLOSUM.

In a particularly preferred embodiment, the molecule comprises or consists of the peptide PPPHPHARIK (SEQ ID. NO.: 21) or PPTHPHARIK (SEQ ID. NO.: 23).

The peptide portion [(Pro)$_n$-X$_r$-His-Pro-His-Ala-Arg-Ile-Lys]$_m$ (SEQ ID. NO.: 1) or [lys-ile-arg-ala-his-pro-his-x$_r$-(pro)$_n$]$_m$ (SEQ ID. NO.: 2) or fragment thereof of the molecule defined above is typically made using protein chemistry techniques for example using partial proteolysis (either exolytically or endolytically), or by de novo synthesis. Alternatively, the peptides may be made by recombinant DNA technology. Suitable techniques for cloning, manipulation, modification and expression of nucleic acids, and purification of expressed proteins, are well known in the art and are described for example in Sambrook et al (2001) "Molecular Cloning, a Laboratory Manual", 3$^{rd}$ edition, Sambrook et al (eds), Cold Spring Harbor Laboratory Press, Cold Spring Harbor, N.Y., USA.

The peptide portion [(Pro)$_n$-X$_r$-His-Pro-His-Ala-Arg-Ile-Lys]$_m$ (SEQ ID. NO.: 1) or [lys-ile-arg-ala-his-pro-his-x$_r$-(pro)$_n$]$_m$ (SEQ ID. NO.: 2) or fragment thereof of the molecule defined above can also be chemically synthesised, for example, by the solid phase peptide synthesis of Merrifield et al (1964). Alternatively, the peptide portion can be synthesised using standard solution methods (see, for example, Bodanszky, 1984 and Dugas et al, 1981). Newly synthesised peptides can be purified, for example, by high performance liquid chromatography (HPLC), and can be characterised using, for example, mass spectrometry or amino acid sequence analysis.

It will be appreciated that other suitable molecules that are capable of preventing or inhibiting the interaction between a Src family kinase (e.g. Src kinase) and AR or ER may include any antibody, either against a Src family kinase (e.g. Src kinase), or either of AR and ER. As mentioned earlier, the inventor believes that the SH3 domain of Src kinase and amino acid residues 377-386 of AR mediate the interaction between Src kinase and AR. Thus, it will be understood that suitable molecules that inhibit or prevent an interaction between a Src family kinase (e.g. Src kinase) and either AR or ER include an antibody against the SH3 domain of a Src family kinase (e.g. Src kinase) or an antibody that binds to AR at a position that corresponds to amino acids 377-386 of the human AR (e.g. an antibody against a peptide having the structure (Pro)$_n$-X$_r$-His-Pro-His-Ala-Arg-Ile-Lys (SEQ ID. NO.: 1), where n is an integer from 1-10, X is any amino acid and r is an integer from 0 to 2, such as an antibody against PPPHPHARIK (SEQ ID. NO.: 21) or PPTHPHARIK (SEQ ID. NO.: 23)). Similarly, the SH2 domain of Src kinase is believed to mediate the interaction between Src kinase and ER. Thus, it will be understood that suitable molecules that inhibit or prevent an interaction between a Src family kinase (e.g. Src kinase) and either AR or ER include an antibody against the SH2 domain of a Src family kinase (e.g. Src kinase). Preferably, the antibody prevents or inhibits the interaction between a Src family kinase (e.g. Src kinase) and AR or ER, selectively, as discussed above.

Similarly, other suitable molecules that bind to the SH3 domain of a Src family kinase include an antibody that beings to the SH3 domain of a Src family kinase (eg Src kinase). Preferably, the antibody binds to the SH3 domain of a Src family kinase (eg Src kinase) selectively.

As used herein, the term "antibody" includes but is not limited to polyclonal, monoclonal, chimeric, single chain, Fab fragments and fragments produced by a Fab expression library. Such fragments include fragments of whole antibodies which retain their binding activity for a target substance, Fv, F(ab') and F(ab')2 fragments, as well as single chain antibodies (scFv), fusion proteins and other synthetic proteins which comprise the antigen-binding site of the antibody. Also included are domain antibodies (dAbs), diabodies, camelid antibodies and engineered camelid antibodies. Furthermore, for administration to humans, the antibodies and fragments thereof may be humanised antibodies, which are now well known in the art (Janeway et al (2001) Immunobiology., 5th ed., Garland Publishing).

Suitable antibodies described above that bind to particular regions of a Src family kinase (e.g. Src kinase) or AR and ER, can be made by the skilled person using technology long-established in the art. Methods of preparation of monoclonal antibodies and antibody fragments are well known in the art and include hybridoma technology (Kohler & Milstein (1975) "Continuous cultures of fused cells secreting antibody of predefined specificity. Nature 256: 495-497); antibody phage display (Winter et al (1994) "Making antibodies by phage display technology." Annu. Rev. Immunol. 12: 433-455); ribosome display (Schaffitzel et al (1999) "Ribosome display: an in vitro method for selection and evolution of antibodies from libraries." *J. Immunol. Methods* 231: 119-135); and iterative colony filter screening (Giovannoni et al (2001) "Isolation of anti-angiogenesis antibodies from a large combinatorial repertoire by colony filter screening." *Nucleic Acids Res.* 29: E27). Further, antibodies and antibody fragments suitable for use in the present invention are described, for example, in the following publications: *"Monoclonal Hybridoma Antibodies: Techniques and Application"*, Hurrell (CRC Press, 1982); *"Monoclonal Antibodies: A Manual of Techniques"*, H. Zola, CRC Press, 1987, ISBN: 0-84936-476-0; *"Antibodies: A Laboratory Manual"* $1^{st}$ Edition, Harlow & Lane, Eds, Cold Spring Harbor Laboratory Press, New York, 1988. ISBN 0-87969-314-2; *"Using Antibodies: A Laboratory Manual"* $2^{nd}$ Edition, Harlow & Lane, Eds, Cold Spring Harbor Laboratory Press, New York, 1999. ISBN 0-87969-543-9; and *"Handbook of Therapeutic Antibodies"* Stefan Dibel, Ed., $1^{st}$ Edition, —Wiley-VCH, Weinheim, 2007. ISBN: 3-527-31453-9.

It is appreciated that the molecule of the invention may comprise the sequence of a cell-penetrating peptide (also known as a protein transduction domain) that facilitates entry into cells. As is well known in the art, cell-penetrating peptides are generally short peptides of up to 30 residues having a net positive charge and act in a receptor-independent and energy-independent manner (Lindgren et al, 2000; Deshayes et al, 2005a and 2005b; Takeuchi et al, 2006, the entire disclosure of which relating to cell-penetrating peptides is incorporated herein by reference). Thus, either of chemical moieties B and R mentioned above, may be a cell-penetrating peptide. If so, the cell-penetrating peptide is preferably cleavable from the portion of the molecule responsible for modulating an activity of a Src family kinase (eg inhibiting or preventing an interaction between a Src family kinase (e.g. Src kinase) and AR or ER; or binding to the SH3 domain of Src). For example, it may be cleavable inside a cell.

The molecule may also be modified so that it can be more easily detected, for example by biotinylating it or by incorporating any detectable label known in the art such as radiolabels, fluorescent labels or enzymatic labels.

The amino acid residues of the molecules described herein may be in the "L" isomeric form. However, residues in the "D" isomeric form can be substituted for any L-amino acid residue, as long as the molecules can still modulate an activity of a Src family kinase (eg inhibit or prevent an interaction between a Src family kinase (e.g. Src kinase) and AR or ER, or bind to the SH3 domain of a Src family kinase). This definition includes, unless otherwise specifically indicated, chemically-modified amino acids, including amino acid analogues (such as penicillamine, 3-mercapto-D-valine), naturally-occurring non-proteogenic amino acids (such as norleucine), and chemically-synthesised compounds that have properties known in the art to be characteristic of an amino acid. The term "proteogenic" indicates that the amino acid can be incorporated into a protein in a cell through well-known metabolic pathways.

Thus, in one embodiment, the peptide portion of the molecule above is the retro-inverso peptide of the peptide $[(Pro)_n-X_r-His-Pro-His-Ala-Arg-Ile-Lys]_m$ (SEQ ID. NO.: 1) or a fragment thereof (preferences for which include those defined above). By retro-inverso peptide (also known as all-D-retro or retro-enantio peptides) we include the meaning of a peptide in which all of the L-amino acids are replaced with D-amino acids and the peptide bonds are reversed. Thus, the peptides are composed of D-amino acids assembled in the reverse order from that of the parent L-sequence. The retro-inverso peptide of $[(Pro)_n-X_r-His-Pro-His-Ala-Arg-Ile-Lys]_m$ (SEQ ID. NO.: 1) is [lys-ile-arg-ala-his-pro-his-$x_r$-$(pro)_n]_m$ (SEQ ID. NO.: 2) (where lowercase letters denote the corresponding D-amino acids). Retro-inverso peptides can be synthesised by methods known in the art, for example such as those described in Meziere et al (1997) *J. Immunol.* 159 3230-3237. This approach involves making pseudopeptides containing changes involving the backbone, and not the orientation of side chains which remain very similar to the parent peptide. Retro-inverse peptides are much more resistant to proteolysis.

For the avoidance of doubt, all of the preferences indicated above for $X_r$, also apply to its corresponding D-amino acid $x_r$.

The peptide portion of the molecule described above can be a peptide "mimetic", i.e. peptidomimetics which mimic the structural features of the peptide comprising or consisting of the amino acid sequence as described above.

Peptidomimetics that are non-peptide in nature can be designed and synthesised by standard organic chemical methods. Peptidomimetics that are non-peptide in nature can be even more advantageous in therapeutic use, in the resistance to degradation, in permeability and in possible oral administration.

Peptidomimetics are small molecules that can bind to proteins by mimicking certain structural aspects of peptides and proteins. They are used extensively in science and medicine as agonists and antagonists of protein and peptide ligands of cellular and other receptors, and as substrates and substrate analogues for enzymes. Some examples are morphine alkaloids (naturally-occurring endorphin analogues), penicillins (semi-synthetic), and HIV protease inhibitors (synthetic). Such compounds have structural features that mimic a peptide or a protein and as such are recognised and bound by other proteins. Binding the peptidomimetic either induces the binding protein to carry out the normal function caused by such binding (agonist) or disrupts such function (antagonist, inhibitor).

A primary goal in the design of peptide mimetics has been to reduce the susceptibility of mimetics to cleavage and inactivation by peptidases. In one approach, such as disclosed by Sherman et al (1990), one or more amide bonds have been replaced in an essentially isosteric manner by a variety of chemical functional groups. This stepwise approach has met with some success in that active analogues have been obtained. In some instances, these analogues have been shown to possess longer biological half-lives than their naturally-occurring counterparts. In another approach, a variety of uncoded or modified amino acids such as D-amino acids and N-methyl amino acids have been used to modify mammalian peptides. Alternatively, a presumed bioactive conformation has been stabilised by a covalent modification, such as cyclization or by incorporation of γ-lactam or other types of bridges (Veber et al, 1978) and Thorsett et al, 1983). Another approach, disclosed by Rich (1986) has been to design peptide mimics through the application of the transition state analogue concept in enzyme inhibitor design. For example, it is known that the secondary alcohol of statine mimics the tetrahedral transition state of the sessile amide bond of the pepsin substrate.

In U.S. Pat. No. 5,552,534, non-peptide compounds are disclosed which mimic or inhibit the chemical and/or biological activity of a variety of peptides. Such compounds can be produced by appending to certain core species, such as the tetrahydropyranyl ring, chemical functional groups which cause the compounds to be at least partially crossreactive with the peptide. Other techniques for preparing peptidomimetics are disclosed in U.S. Pat. Nos. 5,550,251 and 5,288,707.

Commercially available software packages can be used to design small peptides and/or peptidomimetics, preferably non-hydrolysable analogues, as specific antagonists/inhibitors. Suitable commercially available software for analyzing crystal structure, designing and optimizing small peptides and peptidomimetics include, but are not limited to: Macromolecular X-ray Crystallography QUANTA Environment (Molecular Simulations, Inc.); TeXsan, BioteX, and SQUASH (Molecular Structure Corporation); and Crystallographica (Oxford Cryostsystems).

It is appreciated that a salt or derivative of the molecule described herein may be useful to prevent or treat a metastatic cancer (eg one in which an activity of AR and/or ER is a contributory factor), provided that the salt or derivative can modulate an activity of a Src family kinase (eg prevent or inhibit an interaction of a Src family kinase (e.g. Src kinase) with AR or ER, or bind to the SH3 domain of a Src family kinase). By "derivative", we include the meaning of peptides (e.g. the peptide portion [(Pro)$_n$-X$_r$-His-Pro-His-Ala-Arg-Ile-Lys]$_m$ (SEQ ID. NO.: 1) is [lys-ile-arg-ala-his-pro-his-x$_r$-(pro)$_n$]$_m$ (SEQ ID. NO.: 2) of the molecule above) having one or more residues chemically derivatised by reaction of a functional side group. Such derivatised molecules include, for example, those molecules in which free amino groups have been derivatised to form amine hydrochlorides, p-toluene sulfonyl groups, carbobenzoxy groups, t-butyloxycarbonyl groups, chloroacetyl groups or formyl groups. Free carboxyl groups may be derivatised to form salts, methyl and ethyl esters or other types of esters or hydrazides. Free hydroxyl groups may be derivatised to form O-acyl or O-alkyl derivatives. Also included as derivatives are those peptide portions that contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine. The derivatisation does not include changes in functional groups which change one amino acid to another.

Some useful modifications are designed to increase the stability and, therefore, the half-life of molecules (eg peptides) in solutions, particularly biological fluids, such as blood, plasma or serum, by blocking proteolytic activity in the blood. Thus, a peptide may have a stabilising group at one or both termini. Typical stabilising groups include amido, acetyl, benzyl, phenyl, tosyl, alkoxycarbonyl, alkyl carbonyl, benzyloxycarbonyl and the like end group modifications. Additional modifications include using a "D" amino acid in place of a "L" amino acid at the termini, and amide rather than amino or carboxy termini to inhibit exopeptidase activity. Thus, it is appreciated that the peptide portion [(Pro)$_n$-X$_r$-His-Pro-His-Ala-Arg-Ile-Lys]$_m$ (SEQ ID. NO.: 1) is [lys-ile-arg-ala-his-pro-his-x$_r$-(pro)$_n$]$_m$ (SEQ ID. NO.: 2) of the molecule defined above may have a capping moiety at one or both ends, preferably a moiety that is less than 200 Da in molecular weight. Further capping moieties include a naftyl group or a polyethylene glycol group. It is appreciated that retro-inverso peptides are already relatively stable and so may not require additional capping moieties.

Accordingly, in a particularly preferred embodiment, the molecule comprises or consists of the structure Ac-Pro-Pro-Pro-His-Pro-His-Ala-Arg-Ile-Lys-NH$_2$ (SEQ ID. NO.: 21) or Ac-Pro-Pro-Thr-His-Pro-His-Ala-Arg-Ile-Lys-NH$_2$ (SEQ ID. NO.: 23), where Ac is an acetyl group.

Preferably, the molecule of the invention is one that does not reduce or prevent fertility in a subject. As described in the Examples, the inventors have demonstrated that administering the peptide Ac-Pro-Pro-Pro-His-Pro-His-Ala-Arg-Ile-Lys-NH$_2$ (SEQ ID. NO.: 21) to mice does not affect their fertility. It is expected that other molecules that prevent or inhibit an interaction between a Src family kinase (e.g. Src kinase) and AR or ER, or other molecules that bind to the SH3 domain of Src family kinase will have the same activity. Thus, it will be appreciated that the use of the molecule of the invention (eg one that inhibits or prevents an interaction between Src family kinase and AR or ER) in preventing or treating metastatic cancer (eg one in which an activity of AR and/or ER is a contributory factor) in a subject, is particularly suited to subjects who wish to preserve fertility. This is believed to be a significant advancement because as far as the inventors are aware, existing treatments of cancers in which an activity of AR and/or ER is a contributory factor, are known to affect fertility. Methods for assessing fertility in a subject are well known in the art and include assays such as those described in the examples.

In one embodiment, the molecule is administered as a vaccine to generate antibodies. For example, the molecule having the structure defined above may be used in the preparation of an antibody that specifically binds to the AR, and so may be prepared as a vaccine.

It may be desirable to link the molecule to a carrier molecule such as a pro-immunogenic molecule. Suitable examples include bovine serum albumin (BSA) or keyhole limpet hemocyanin (KLH). Additionally or alternatively, the molecule may be comprised in a lipid composition such as a lipid particle, a nanocapsule, a liposome or lipid vesicle. The molecule may also be incorporated in coating capsules for slow release as described further below.

By "metastatic cancer" we include the meaning that the cancer has metastasised. Thus, the primary tumour has spread to one or more other sites of the body and has established one or more secondary tumours. Metastatic cancer can be diagnosed using routine methods known in the art. Typically, diagnosis involves taking a biopsy and assessing whether any cancerous cells resemble those cells in the organ or tissue from which the biopsy was taken (eg by examining cell histology by microscope or by using immunohistochemistry techniques).

Examples of metastatic cancers amenable to prevention or treatment according to the present invention include metastatic fibrosarcoma; metastatic prostate cancer; metastatic breast cancer; metastatic uterine fibroids; metastatic fibroids polyps hyperplasia; metastatic ovarian cancer; metastatic bladder cancer; metastatic cervical cancer; metastatic uterine cancer; metastatic testicular cancer; metastatic lung cancer; metastatic intestinal cancer; metastatic liver cancer; metastatic kidney cancer; and metastatic oesophageal cancer By a metastatic cancer in which an activity of AR and/or ER is a contributory factor, we include any metastatic cancer in which at least part of the pathology is mediated by an activity of AR and/or ER. The pathology may be due to an increased or decreased activity of AR and/or ER. The metastatic cancer may be caused by the AR and/or ER activity or may simply be characterised by AR and/or ER activity. The activity of the AR and/or ER may contribute directly to the metastatic cancer or may contribute indirectly to the metastatic cancer. Generally, the metastatic cancer in which an activity of AR and/or ER is a contributory factor is one where the pathogenesis involves aberrant signalling through the AR and/or ER (e.g. one where cell proliferation is modulated by AR and/or ER). For example, the metastatic cancer may involve aberrant signalling through the Src family kinase pathway. Such cancers may be diagnosed readily using conventional methods available in the art.

Examples of metastatic cancers in which the AR and/or ER is a contributory factor include metastatic fibrosarcoma, metastatic prostate cancer, metastatic breast cancer, metastatic uterine fibroids, metastatic fibroids polyps hyperplasia, metastatic ovarian cancer, metastatic bladder cancer, metastatic cervical cancer, metastatic uterine cancer, and metastatic testicular cancer. Preferably, the metastatic cancer is metastatic fibrosarcoma.

In an embodiment, the metastatic cancer is not metastatic prostate cancer.

In an embodiment, the subject is one who wishes to preserve fertility. By 'wishes to preserve fertility' we include the meaning of a subject in whom it is desired not to reduce fertility. For example, the subject may wish to conceive. Such subjects therefore represent a sub-group of metastatic cancer patients as, in addition to having metastatic cancer, they additionally wish to preserve fertility. Typically, such subjects are aged between 16 and 50, for instance 20-45 or 25-40. It is believed that, following administration of the molecule of the invention, the subjects remain fertile for at least one month, such as at least two, three, four, five or six months, or for at least one, two or three years.

Given their advantageous effect on fertility, it will be appreciated that the molecules of the invention are particularly suited to prevent or treat metastatic cancers of the reproductive system. Thus, it may be desirable to use the molecules of the invention to prevent or treat a metastatic gynaecological cancer such as one or more selected from the group consisting of metastatic uterine fibroids; metastatic ovarian cancer; metastatic cervical cancer; or metastatic uterine cancer It is appreciated that the molecule or derivative or fragment thereof described herein may be formulated with a pharmaceutically acceptable excipient, solvent, diluent or carrier (including combinations thereof). The carrier, diluent, solvent or excipient must be "acceptable" in the sense of being compatible with the molecule or derivative and not deleterious to the recipients thereof. Typically, the carriers will be water or saline (e.g. physiological saline) which will be sterile and pyrogen free. Suitable excipients include mannitol and dextrose. Acceptable carriers, solvents, diluents and excipients for therapeutic use are well known in the pharmaceutical art, and are described, for example, in Remington's Pharmaceutical Sciences, Mack Publishing Co. (A. R. Gennaro ed. 1985). The choice of pharmaceutical carrier, solvent, excipient or diluent can be selected with regard to the intended route of administration and standard pharmaceutical practice. The pharmaceutical compositions may comprise as, or in addition to, the carrier, excipient, solvent or diluent any suitable binder, lubricant, suspending agent, coating agent, or solubilising agent. Preservatives, stabilisers, dyes and even flavouring agents may be provided in the pharmaceutical composition.

The formulations may conveniently be presented in unit dosage form and may be prepared by any of the methods well known in the art of pharmacy. Such methods include the step of bringing into association the molecule with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations in accordance with the present invention suitable for oral administration may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycolate, cross-linked povidone, cross-linked sodium carboxymethyl cellulose), surface-active or dispersing agent. Molded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide desired release profile.

Formulations suitable for topical administration in the mouth include lozenges comprising the active ingredient in a flavoured base, usually sucrose and acacia or tragacanth; pastilles comprising the active ingredient in an inert base such as gelatin and glycerin, or sucrose and acacia; and mouth-washes comprising the active ingredient in a suitable liquid carrier.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

In addition to the ingredients particularly mentioned above, the formulations may include other agents conventional in the art having regard to the type of formulation in question, for example those suitable for oral administration may include flavouring agents.

The molecule or derivative or fragment thereof, or a formulation thereof, may be administered by any conventional method including oral, intranasal, and parenteral (e.g. subcutaneous or intramuscular) injection. Preferred routes include oral, intravenous or subcutaneous injection. The treatment may consist of a single dose or a plurality of doses over a period of time. The molecule or derivative thereof may formulated in a sustained release formulation so as to provide sustained release over a prolonged period of time such as over at least 2 or 4 or 6 or 8 weeks Preferably, the sustained release is provided over at least 4 weeks.

In a particular embodiment, the molecule or derivative or fragment thereof is formulated in a way that allows direct administration to the reproductive system. Thus, the molecule or derivative or fragment thereof may be formulated in a vaginal or rectal suppository, an intravaginal tampon, an intravaginal ring, an intravaginal pessary, an intravaginal sponge, or a medicated intrauterine device (IUD); or in a sustained release formulation.

The amount of the molecule or derivative or fragment thereof which is administered to the subject is an amount effective to combat the particular subject's condition. The amount may be determined by the physician.

In an embodiment, the molecule, such as the one comprising or consisting of the structure $B_j$-[(Pro)$_n$-$X_r$-His-Pro-His-Ala-Arg-Ile-Lys]$_m$-$R_p$ (SEQ ID. NO.: 1) or $B_j$-[lys-ile-arg-ala-his-pro-his-$x_r$-(pro)$_n$]$_m$-$R_p$ (SEQ ID. NO.: 2) defined above, is administered to a subject using a daily dose of between 1-1000 ng, such as a daily dose of 1-900 ng, 1-800 ng, 1-700 ng, 1-600 ng, 1-500 ng, 1-400 ng, 1-300 ng, 1-200 ng or 1-100 ng. Thus, the molecule, such as the one comprising or consisting of the structure $B_j$-[(Pro)$_n$-$X_r$-His-Pro-His-Ala-Arg-Ile-Lys]$_m$-$R_p$ (SEQ ID. NO.: 1) or $B_j$-[lys-ile-arg-ala-his-pro-his-$x_r$-(pro)$_n$]$_m$-$R_p$(SEQ ID. NO.: 2) defined above, may be administered to a subject using a daily dose of at least 1 ng, 10 ng, 20 ng, 30 ng, 40 ng, 50 ng, 60 ng, 70 ng, 80 ng, 90 ng or 100 ng, or at least 150 ng or 200 ng.

In another embodiment, the molecule, such as the one comprising or consisting of the structure $B_j$-[(Pro)$_n$-$X_r$-His-Pro-His-Ala-Arg-Ile-Lys]$_m$-$R_p$ (SEQ ID. NO.: 1) or $B_j$-[lys-ile-arg-ala-his-pro-his-$x_r$-(pro)$_n$]$_m$-$R_p$ (SEQ ID. NO.: 2) defined above, is administered at intervals (e.g. daily, two-daily or weekly) over the course of at least 5, 10, 15, 20, 25, 30, 35, 40, 45, 50, 55 or 60 days, and even over the course of at least 3, 4, 5, 6, 7, 8, 9, 10, 11, 12 or 18 months, or over the course of at least 2, 3, 4 or 5 years. Where the molecule or derivative is administered at intervals, it will be understood that it may be desirable to use different routes of administration at different intervals. For example, the molecule or derivative may be first administered by injection and a follow up dose administered by subcutaneous implant.

The optimum administration interval and duration of treatment will generally depend on how severe the condition is.

In one embodiment, the subject is administered a further therapeutic agent in addition to the molecule or derivative described herein. For example, when administering the molecule or derivative thereof to prevent or treat a particular metastatic cancer, a further therapeutic agent known to be useful for preventing or treating that metastatic cancer may be administered. Thus, when preventing or treating metastatic breast cancer, the further therapeutic agent may be an agent known to prevent or treat metastatic breast cancer, when preventing or treating metastatic uterine cancer, the further therapeutic agent may be an agent known to prevent or treat metastatic uterine cancer, and so on.

Typically, the further therapeutic agent may be any agent that reduces proliferation such as any of a cytostatic agent or a cytosidal agent or an anticancer agent. It will be appreciated that the further therapeutic agent may be one that is known to be effective in reducing or inhibiting metastasis.

It is appreciated that the further therapeutic agent may be administered at the same time as the molecule or derivative thereof described herein (i.e. simultaneous administration optionally in a co-formulation) or at a different time to the molecule or derivative thereof described herein (i.e. sequential administration where the further therapeutic agent is administered before or after the molecule or derivative thereof is administered). The further therapeutic agent may be administered in the same way as the molecule of the invention described herein, or by using the usual administrative routes for that further therapeutic agent.

A second aspect of the invention provides a composition comprising (i) a molecule that modulates an activity of a Src family kinase, and (ii) a therapeutic agent suitable for preventing or treating a metastatic cancer. The composition may be a pharmaceutical composition which further comprises a pharmaceutically acceptable excipient, carrier or diluent.

Thus, the invention provides a composition comprising (i) a molecule that inhibits or prevents an interaction between a Src family kinase (e.g. Src kinase) and an androgen or estradiol receptor, and (ii) a therapeutic agent suitable for preventing or treating a metastatic cancer in which an activity of AR and/or ER is a contributory factor. The composition may be a pharmaceutical composition which further comprises a pharmaceutically acceptable excipient, carrier or diluent.

Similarly, the invention provides a composition comprising (i) a molecule that binds to the SH3 domain of a Src family kinase (e.g. Src kinase) and (ii) a therapeutic agent suitable for preventing or treating a metastatic cancer. The composition may be a pharmaceutical composition which further comprises a pharmaceutically acceptable excipient, carrier or diluent.

Preferences for the molecule, derivative, the further therapeutic agent, the metastatic cancer, and the subject to be treated include those mentioned above with respect to the first aspect of the invention. For example, the molecule may comprise or consist of the structure: $B_j$-[(Pro)$_n$-$X_r$-His-Pro-His-Ala-Arg-Ile-Lys]$_m$-$R_p$, (SEQ ID. NO.: 1) or $B_j$-[lys-ile-arg-ala-his-pro-his-$x_r$-(pro)$_n$]$_m$-$R_p$ (SEQ ID. NO.: 2), or a derivative or fragment thereof, wherein B is a first chemical moiety, j is 0 or 1, n is an integer from 1-10, m is an integer from 1 to 3, R is a second chemical moiety, p is 0 or 1, and [lys-ile-arg-ala-his-pro-his-x-(pro)$_n$] (SEQ ID. NO.: 2) is the retro-inverso peptide of [(Pro)$_n$-$X_r$-His-Pro-His-Ala-Arg-Ile-Lys] (SEQ ID. NO.: 1). Most preferably, the molecule has the structure Ac-Pro-Pro-Pro-His-Pro-His-Ala-Arg-Ile-Lys-NH$_2$ (SEQ ID. NO.: 22) or Ac-Pro-Pro-Thr-His-Pro-His-Ala-Arg-Ile-Lys-NH$_2$ (SEQ ID. NO.: 24), where Ac is an acetyl group. Preferably, the subject is a human.

Accordingly, the invention includes a composition comprising (i) a molecule that modulates an activity of a Src family kinase, and (ii) a therapeutic agent suitable for preventing or treating a metastatic cancer, for use in preventing or treating a metastatic cancer. Thus, the invention provides a composition comprising (i) a molecule that inhibits or prevents an interaction between a Src family kinase (e.g. Src kinase) and an androgen or estradiol receptor, and (ii) a therapeutic agent suitable for preventing or treating a metastatic cancer in which an activity of AR and/or ER is a contributory factor, for use in preventing or treating a metastatic cancer in which an activity of AR and/or ER is a contributory factor. The invention also provides a composition comprising (i) a molecule that binds to the SH3 domain of a Src family kinase (e.g. Src kinase) and (ii) a therapeutic agent suitable for preventing or treating a metastatic cancer, for use in preventing or treating a metastatic cancer. The composition may be a pharmaceutical composition which further comprises a pharmaceutically acceptable excipient, carrier or diluent.

Similarly, the invention includes the use of a composition comprising (i) a molecule that modulates an activity of a Src family kinase, and (ii) a therapeutic agent suitable for preventing or treating a metastatic cancer, in the manufacture of a medicament for preventing or treating a metastatic cancer. Thus, the invention provides the use of a composition comprising (i) a molecule that inhibits or prevents an interaction between a Src family kinase (e.g. Src kinase) and an androgen or estradiol receptor, and (ii) a therapeutic agent suitable for preventing or treating a metastatic cancer in which an activity of AR and/or ER is a contributory factor, in the manufacture of a medicament for preventing or treating a metastatic cancer in which an activity of AR and/or ER is a contributory factor. The invention also provides the use of a composition comprising (i) a molecule that binds to the SH3 domain of a Src family kinase (e.g. Src kinase) and (ii) a therapeutic agent suitable for preventing or treating a metastatic cancer, in the manufacture of a medicament for preventing or treating a metastatic cancer. The composition may be a pharmaceutical composition which further comprises a pharmaceutically acceptable excipient, carrier or diluent.

It will be appreciated that the invention includes a molecule that modulates an activity of a Src family kinase (eg Src kinase) for use in preventing or treating metastatic cancer, wherein the subject is also administered a therapeutic agent for preventing or treating said metastatic cancer. Thus, the invention includes a molecule that inhibits or prevents an interaction between a Src family kinase (e.g. Src kinase) and an androgen or estradiol receptor, for use in preventing or treating a metastatic cancer in which an activity of AR and/or ER is a contributory factor in a subject, wherein the subject is also administered a therapeutic agent suitable for preventing or treating said metastatic cancer. The invention also includes a molecule that binds to the SH3 domain of a Src family kinase (e.g. Src kinase) for use in preventing or treating a metastatic cancer, wherein the subject is also administered a therapeutic agent suitable for preventing or treating said metastatic cancer.

Likewise, it will be understood that the invention includes the use of a molecule modulates an activity of a Src family kinase (e.g. Src kinase) in the manufacture of a medicament for preventing or treating a metastatic cancer, wherein the subject is also administered a therapeutic agent suitable for preventing or treating said metastatic cancer. Thus, the invention includes the use of a molecule that inhibits or prevents an interaction between a Src family kinase (e.g. Src kinase) and an androgen or estradiol receptor, in the manufacture of a medicament for preventing or treating a metastatic cancer in which an activity of AR and/or ER is a contributory factor in a subject, wherein the subject is also administered a therapeutic agent suitable for preventing or treating said metastatic cancer in which an activity of AR and/or ER is a contributory factor. The invention also includes the use of a molecule that binds to the SH3 domain of a Src family kinase (e.g. Src kinase) in the manufacture of a medicament for preventing or treating a metastatic cancer, wherein the subject is also administered a therapeutic agent suitable for preventing of treating said metastatic cancer.

Preferably, the molecule may comprise or consist of the structure: $B_j$-[(Pro)$_n$-X$_r$-His-Pro-His-Ala-Arg-Ile-Lys]$_m$-R$_p$, (SEQ ID. NO.: 1) or $B_j$-[lys-ile-arg-ala-his-pro-his-x$_r$-(pro)$_n$]$_m$-R$_p$ (SEQ ID. NO.: 2), or a derivative or fragment thereof, wherein B is a first chemical moiety, j is 0 or 1, n is an integer from 1-10, m is an integer from 1 to 3, R is a second chemical moiety, p is 0 or 1, and [lys-ile-arg-ala-his-pro-his-x$_r$-(pro)$_n$] (SEQ ID. NO.: 2) is the retro-inverso peptide of [(Pro)$_n$-X$_r$-His-Pro-His-Ala-Arg-Ile-Lys] (SEQ ID. NO.: 1). Most preferably, the molecule has the structure Ac-Pro-Pro-Pro-His-Pro-His-Ala-Arg-Ile-Lys-NH$_2$ (SEQ ID. NO.: 21) or Ac-Pro-Pro-Thr-His-Pro-His-Ala-Arg-Ile-Lys-NH$_2$ (SEQ ID. NO.: 23), where Ac is an acetyl group.

The inventors have found that molecules that modulate an activity of a Src family kinase (e.g. Src kinase) may be used to prevent or treat a metastatic cancer (e.g. molecules that inhibit or prevent an interaction between a Src family kinase and the AR and/or ER may used to prevent or treat a metastatic cancer in which an activity of AR and/or ER is a contributory factor; and molecules that bind to the SH3 domain of a Src family kinase may be used to prevent or treat metastatic cancer). Thus, it is appreciated that by assessing the effect of test agents on a Src family kinase (e.g. Src kinase), one can identify agents to prevent or treat a metastatic cancer.

Accordingly, a further aspect of the invention provides a method of selecting an agent to prevent or treat a metastatic cancer, the method comprising determining whether a test agent modulates an activity of a Src family kinase.

Thus, the invention provides a method of selecting an agent to prevent or treat a metastatic cancer in which an activity of AR and/or ER is a contributory factor, the method comprising determining whether a test agent reduces an interaction between (a) AR or ER or a portion thereof, said portion being capable of binding to a Src family kinase (e.g. Src kinase) and (b) a Src family kinase (e.g. Src kinase) or a portion thereof, said portion being capable of binding to AR or ER.

The invention also provides a method of selecting an agent to prevent or treat a metastatic cancer, the method comprising determining whether a test agent binds to the SH3 domain of a Src family kinase (e.g. Src kinase).

Preferences for AR, ER and Src family kinase, and for the metastatic cancer include those defined above with respect to the first aspect of the invention.

It will be appreciated that, when assessing the invention between AR or ER, and Src family kinase, it is not necessary to provide the entire AR or ER, or Src family kinase for the purpose of the screening method. Portions of the AR or ER that are capable of binding to Src family kinase (e.g. Src kinase) may be used, and portions of Src family kinase (e.g. Src kinase) that are capable of binding to the AR or ER may be used. For example, as described above, the SH3 and SH2 domains of Src family kinase (e.g. Src kinase) are believed to mediate the interaction between Src family kinase and each of AR and ER, respectively. Thus, a portion of Src family kinase (e.g. Src kinase) corresponding to the SH3 domain or part thereof capable of binding to AR, or a portion of Src family kinase (e.g. Src kinase) corresponding to the SH2 domain or part thereof capable of binding to ER, may be used. Likewise, a portion of the AR corresponding to amino acid residues 377-386 of AR, believed to mediate the interaction between AR and the SH3 domain of Src family kinase (e.g. Src kinase), may be used. Other suitable portions may be determined by one of skilled in the art and are described, for example, in Migliaccio et al (Oncogene 2007, 26: 6619) and Migliaccio et al (Cancer Research 2005, 65(22): 10585-93).

The test agent may be any suitable test agent including a polypeptide, an antibody, a small molecule, a natural product, a peptidomimetic or a nucleic acid. It is appreciated that a library of test agents may be screened as part of a high throughput screen.

Various techniques can be used to determine a test agent's effect on the interaction between AR or ER and Src family kinase (e.g. Src kinase) or portions thereof, and whether a test agent binds to the SH3 domain of a Src family kinase (e.g. Src kinase), for example as described above and which are well known in the art (e.g. from Migliaccio et al (Oncogene 2007, 26: 6619) and Migliaccio et al (Cancer Research 2005, 65(22): 10585-93).

In one embodiment, the method comprises the step of isolating a test agent that modulates an activity of a Src family kinase (e.g. Src kinase). Hence, the method may comprise the step of isolating a test agent that reduces an interaction between (a) AR or ER or a portion thereof, said portion being capable of binding to a Src family kinase and (b) a Src family kinase or a portion thereof, said portion being capable of binding to AR or ER. Similarly, the method may comprise the step of isolating a test agent that binds to the SH3 domain of a Src family kinase.

Preferably, the test agent selected is one that reduces an interaction (a) AR or ER or a portion thereof, said portion being capable of binding to a Src family kinase and (b) a Src family kinase or a portion thereof, said portion being capable of binding to AR or ER, by a factor of at least 10%, 20%, 30%, 40% or 50% of the original binding in the absence of the test agent, and more preferably by a factor of at least 60%, 70%, 80%, 90% or 95%.

In one embodiment, the method further comprises identifying the test agent as an agent which prevents or treats a metastatic cancer (e.g. a metastatic cancer in which an activity of AR and/or ER is a contributory factor). For example, the method may further comprise assessing the efficacy of the test agent in an appropriate assay for the particular metastatic cancer in question (e.g. an animal model of the metastatic cancer). For instance, the method may be used to select an agent to prevent or treat metastatic breast cancer such that it involves assessing the effect of the agent in a model of metastatic breast cancer. Suitable models of such conditions are well known in the art, and may be in vitro or in vivo. In one example, the effect of the agent on one or more markers of metastasis in an in vitro cell line may be assessed, such as cell motility and/or MMP expression, for example as described further in Example 1.

It will be appreciated that the test agent selected is an agent that modulates an activity of a Src family kinase (e.g. Src kinase) and so can be used as such. For instance, the agent may be one that inhibits or prevents an interaction between a Src family kinase and an AR or ER within the meaning of the first aspect of the invention, or it may be one that binds to the SH3 domain of a Src family kinase within the meaning of the first aspect of the invention.

It is appreciated that in the method described herein, which may be drug screening methods, a term well known to those skilled in the art, the test agent may be a drug-like compound or lead compound for the development of a drug-like compound.

The term "drug-like compound" is well known to those skilled in the art, and may include the meaning of a compound that has characteristics that may make it suitable for use in medicine, for example as the active ingredient in a medicament. Thus, for example, a drug-like compound may be a molecule that may be synthesised by the techniques of organic chemistry, less preferably by techniques of molecular biology or biochemistry, and is preferably a small molecule, which may be of less than 5000 daltons and which may be water-soluble. A drug-like compound may additionally exhibit features of selective interaction with a particular protein or proteins and be bioavailable and/or able to penetrate target cellular membranes or the blood:brain barrier, but it will be appreciated that these features are not essential.

The term "lead compound" is similarly well known to those skilled in the art, and may include the meaning that the compound, whilst not itself suitable for use as a drug (for example because it is only weakly potent against its intended target, non-selective in its action, unstable, poorly soluble, difficult to synthesise or has poor bioavailability) may provide a starting-point for the design of other compounds that may have more desirable characteristics.

In one embodiment, the method is performed in vitro. By in vitro we include both cell-free assays and cell-based assays. For example, the method may be performed in isolated human cell lines or in cell lines that can be easily manipulated within a laboratory (e.g. *Escherichia coli* and *Saccharomyces cerevisiae*).

In an alternative embodiment, the method is performed in vivo, for example in animal models of the particular metastatic cancers.

The invention provides any molecule, use, method or composition substantially as described herein.

BRIEF DESCRIPTION OF THE DRAWINGS

The invention will now be described with the aid of the following figures and examples.

FIG. 3: Inhibition by S1 peptide of AR/Src complex, Src activation and DNA synthesis triggered by EGF in HT1080 cells. Quiescent HT1080 cells were used. The cells were left un-stimulated or stimulated for 10 min with EGF (at 100 ng/ml; Roche) in the absence or presence of S1 or Ss peptide (both at 1 nM). Casodex (at 10 µM) was used for comparison with the S1 peptide. The same concentrations of peptides and Casodex were used throughout the experiments. Upper section in A, the Western blot of HT1080 cell lysates with anti-EGFR antibody is shown. Tubulin (tub) was revealed by immunoblot as a loading control (loading). Lower section in A, lysates were immune-precipitated with anti EGFR Ab and proteins in immune-complexes were detected using antibodies against the indicated proteins. In B, lysates were immune-precipitated with the anti-Src MAb and Src activity in immune-complexes was assayed using enolase as a substrate. In C, cells on coverslips were left untreated or treated for 18 h with the indicated compounds. After in vivo pulse with BrdU (100 μM; Sigma), BrdU incorporation was analyzed by IF and expressed as % of total nuclei. Mean and SEM are shown. n represents the number of experiments.

FIG. 11A-11J: Homologues of PPPHPHARIK (SEQ ID. NO.: 21) in a selection of species.

Figure 1:
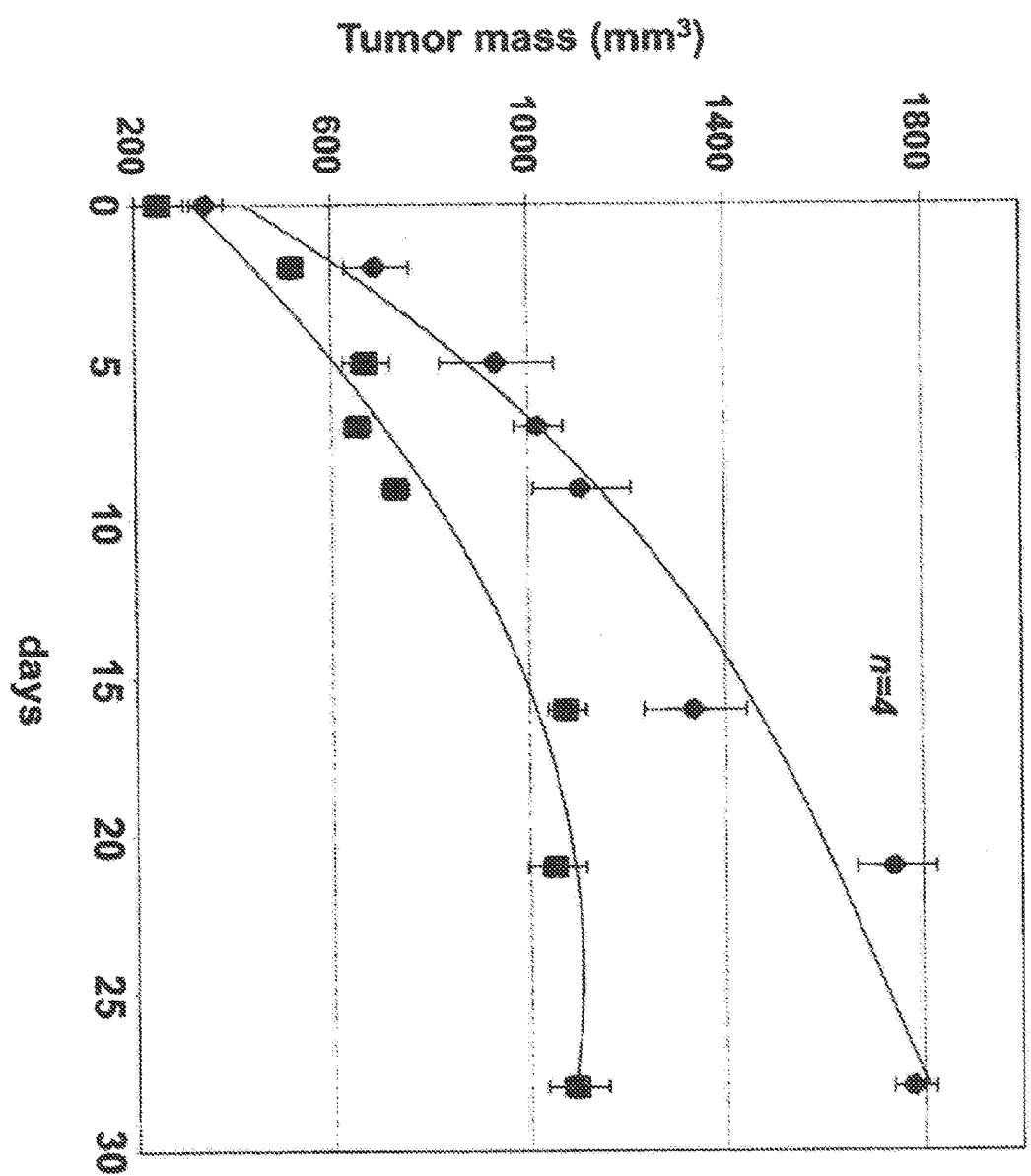
FIG. 1: Casodex reduces the growth of human fibrosarcoma HT1080 xenografts. HT1080 xenografts were established in nude male mice as described in Methods. Tumors were treated with vehicle alone (ethanol), or the pure androgen antagonist, Casodex (Cx; at 1 µM; Sigma-Aldrich). Tumor mass was measured at the indicated times. Mean and SEM are shown. n represents the number of experiments.

EXAMPLE 1: TARGETING ANDROGEN RECEPTOR/SRC COMPLEX IMPAIRS THE AGGRESSIVE PHENOTYPE OF HUMAN FIBROSARCOMA CELLS

Summary

The highly aggressive human fibrosarcoma HT1080 cell line harbors classical androgen receptor (AR). The pure anti-androgen Casodex inhibits the growth of HT1080 cell xenografts in immune-depressed mice, thus revealing a role of androgen receptor in fibrosarcoma progression. Such a role has been investigated in HT1080 cultured cells. In contrast with androgens, EGF robustly increases the DNA synthesis in these cells. Casodex abolishes the EGF mitogenic effect, implicating a crosstalk between EGF-R and AR. The mechanism underlying EGF/AR crosstalk has been analyzed using the AR-derived small peptide, S1 (Ac-PPPHPHARIK-NH2 (SEQ ID. NO.: 22) where Ac is an acetyl group) that prevents AR/Src tyrosine kinase association and Src activation triggered by androgens in various cell types, including human prostate cancer-derived LNCaP cells.

We here observe that EGF induces AR/Src association, and the S1 peptide inhibits the assembly of this complex and the consequent Src activation in HT1080 cells. S1 peptide also inhibits the EGF-stimulated DNA synthesis. EGF increases cell migration as well as the matrix metalloproteinase-9 (MMP9) secretion in HT1080 cells. Here again, the peptide inhibits these processes.

This study for the first time shows that targeting the AR domain involved in AR/Src association impairs the EGF signalling in human fibrosarcoma cells. The EGF-elicited processes inhibited by the peptide (DNA synthesis, motility and MMP9 secretion) cooperate each other in increasing the aggressive phenotype of HT1080 cells. Therefore, the AR/Src interaction represents a new potential therapeutic target in fibrosarcoma as well as in other metastatic cancers.

Introduction

AR is the main target of prostate cancer therapy and inhibition of its activity by androgen binding antagonists represents the most used therapeutic approach of this cancer. Such a therapy is initially effective, but at later stages frequently fails.

Clinical studies reported that steroid receptors (SRs), including AR, are expressed in a large set of human soft tissue sarcomas of different histological origin (1). Human fibrosarcoma HT1080 cells have been so far considered AR-negative because of the scant androgen-regulated transcription (2). Our lab recently observed that these cells harbour low levels of classical, transcriptional incompetent AR, which mediates androgen-induced migration in the absence of DNA synthesis (3).

In different cell types, androgens act through a non-transcriptional mechanism by activating extra-nuclear circuits (4-5). Thus, signalling effectors or scaffolds either transfer the mitogenic hormonal message to nuclei or increase cell motility by modifying cytoskeleton actin when they are directly engaged by a sub-population of extra-nuclear AR.

Growth factors (GF) and their cognate receptors engage extra-nuclear AR to transmit their mitogenic signalling (6), and the mitogenic activity mediated by AR can be stimulated by EGF in AR-expressing cancer cells (7).

We here report that the pure androgen antagonist, Casodex inhibits the growth of HT1080 cells in vivo. A mechanism potentially responsible for this effect has been analyzed. Present experiments reveal that EGF transduces its signal through AR/Src complex in HT1080 cells. Such a cross talk regulates different properties of HT1080 cells, which are crucial for fibrosarcoma progression.

Materials and Methods

Cell Culture, Constructs, Transfection, Transactivation Assay and Peptides

HT-1080, NIH3T3, and LNCaP cells were cultured, made quiescent and transfected as described (3). cDNA encoding the wild type hAR was in pSG5 (8). Transactivation assay in HT1080 cells was done (3), using the 3416 or the 3424 construct in pTK-TATA-Luc (9). The Src-S1 (S1) and the scrambled (Ss) peptides were synthesized and used as reported (10).

BrdU Incorporation, Migration, Wound Healing and MMP-9 Assay

BrdU incorporation, migration and wound healing analysis were done as described (3, 11). MMP-9 activity was assayed (12, 13), using the fluorescent AK411 kit (BIOMOL Res. Lab.).

Immunofluoresence

BrdU and AR were stained and analyzed by IF (3, 11, 14), using a DMBL Leica fluorescent microscope (Leica Microsystems; GmbH-Germany).

Antibodies, Immunoprecipitation, Immunoblotting and Src Kinase Assay

Src tyrosine kinase was immune-precipitated, detected and assayed using enolase as a substrate (15). Src, EGF-R and tubulin were detected from cell lysates using appropriate antibodies (7). AR was immune-precipitated and detected as reported (3). The ECL system (GE Healthcare) was used to reveal immune-reactive proteins.

Mouse Xenografts

HT1080 cells in 50% (v/v) Matrigel solution in phosphate-buffered saline (PBS; pH 7.4) were subcutaneously injected in the dorsal posterior region at $2.5 \times 10^6$ cells/male athymic mice (CD mice, Charles-River Italia) without hormone priming. Animals were randomly selected for the treatment with Casodex dissolved in 0.1% ethanol or vehicle alone for additional 4 weeks. Tumour volumes of HT1080 cell xeno-grafts were measured by a calliper and expressed as tumour mass ($mm^3$). For the treatment of each animal, 200 µl of 1 µM Casodex in 0.1% ethanol or the same amount of vehicle alone were intra-peritoneally administered at alternate days to the mice. No difference in body weight was detected between control mice or Casodex-treated mice.

Results

Figure 2:
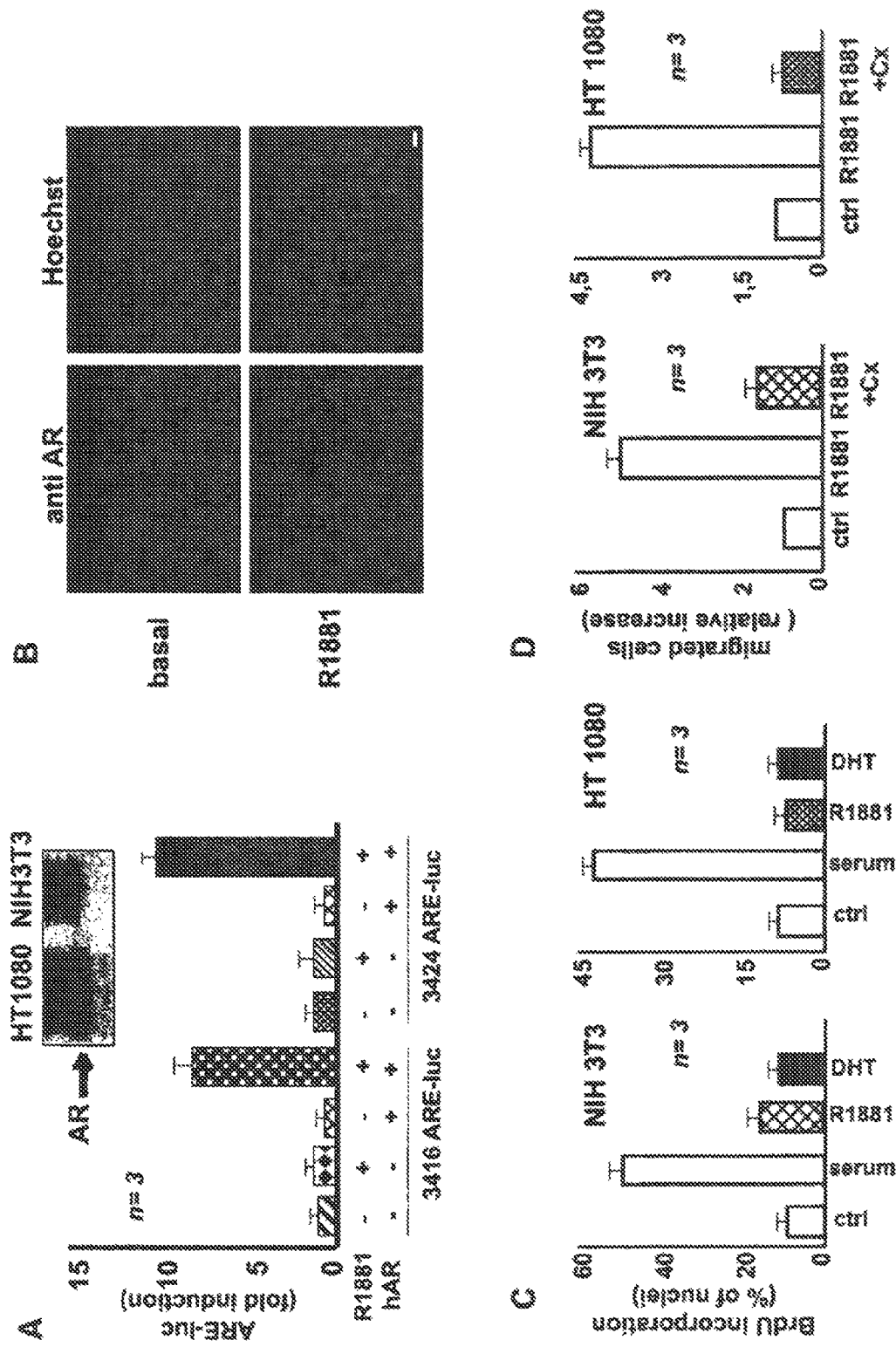
FIG. 2: HT1080 cells harbour transcriptional inactive AR. Androgen challenging of these cells neither induces AR nuclear translocation, nor enhances DNA synthesis while robustly increases cell motility. In A, quiescent HT1080 cells were transfected with 3416 or 3424 ARE-luc constructs with or without hAR expressing plasmid. Details of these procedures have been described in Methods. Cells were left un-stimulated or stimulated for 18 h with 10 nM R1881. The luciferase activity was assayed, normalized using beta-gal as an internal control, and expressed as fold induction. Means and SEM are shown; n represents the number of experiments. The inset in A shows the Western blot of HT1080 or NIH3T3 cell lysates with the C-19 anti-AR antibody. In B, quiescent HT1080 cells on coverslips were left untreated or treated for 60 min with 10 nM R1881. Cells were analysed by IF for AR (left images) or Hoechst (right images). Images are representative of three independent experiments. Bar, 5 am. In C and D, NIH3T3 and HT1080 cells were left untreated or treated with the indicated compounds (R1881 and DHT were used both at 10 nM; serum was used at 20%). In C, BrdU incorporation in cells on coverslips was analysed and expressed as in FIG. 2. In D, the number of migrated cells was evaluated and expressed as relative increase. Mean and SEM is shown. n represents the number of experiments.
Figure 4:
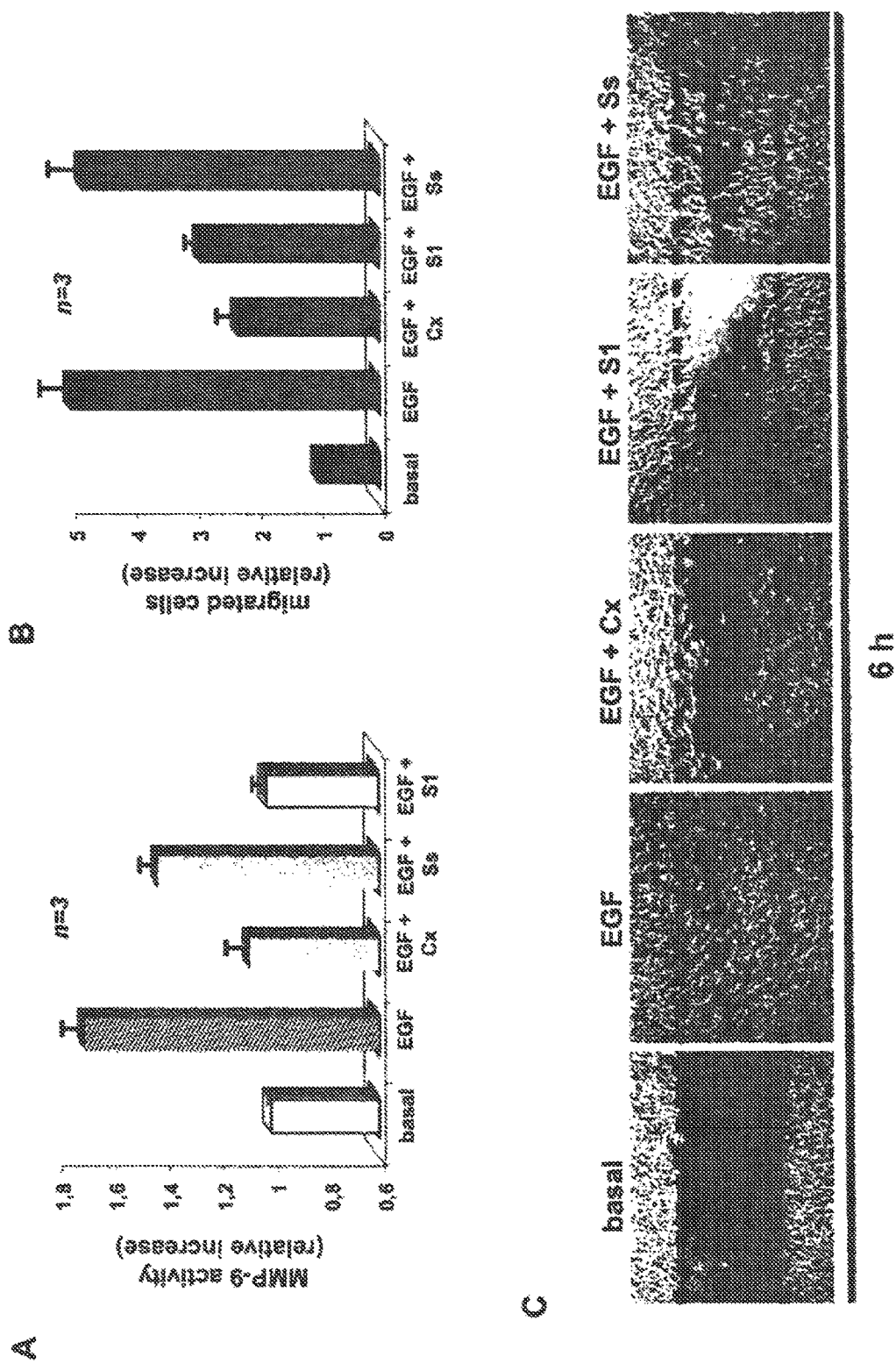
FIG. 4: The S1 peptide inhibits EGF-stimulated migration and MMP-9 secretion in HT1080 cells. Quiescent HT1080 cells were used. In A, cells were left untreated or treated for 6 h with the indicated compounds. MMP-9 release was assayed as described in Methods. In B, cells were allowed to migrate for 6 h in Trans-well filters in the absence or presence of the indicated compounds. Migrated cells were stained and counted as reported in Methods. In A and B, data were expressed as relative increase. Mean and SEM is shown. n represents the number of experiments. In C, cells were wounded and then left unstimulated or stimulated for 6 h with the indicated compounds. Contrast-phase images are representative of 3 different experiments, each performed in duplicate.
Figure 5:
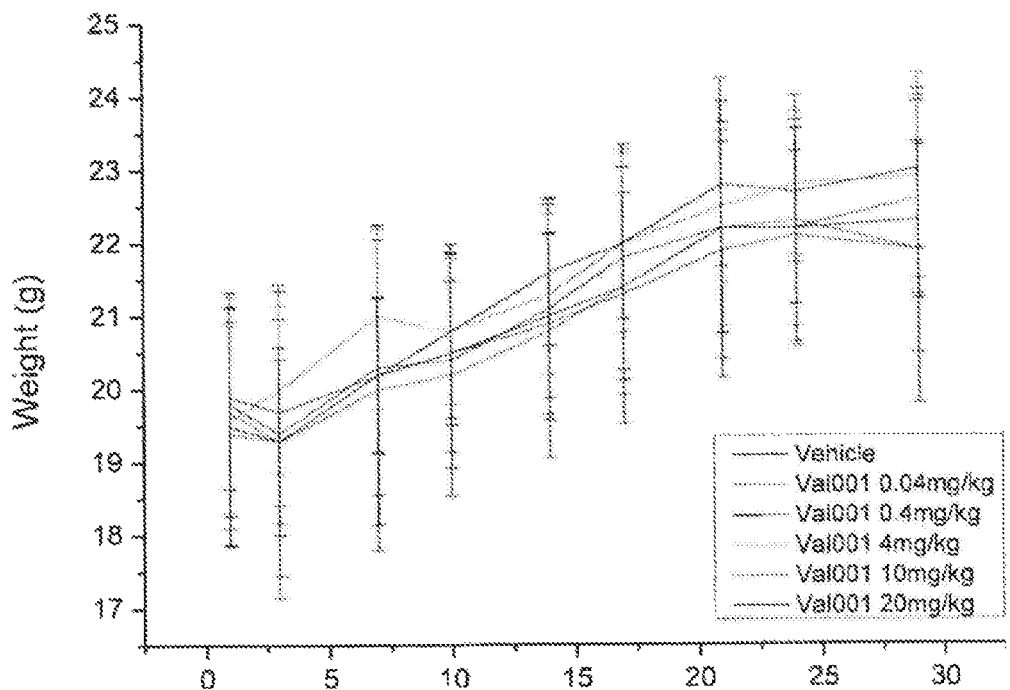
FIG. 5: The body weight of the treatment groups during the study (mean±SD). Figure was prepared from the original data shown in Table 1.
Figure 6:
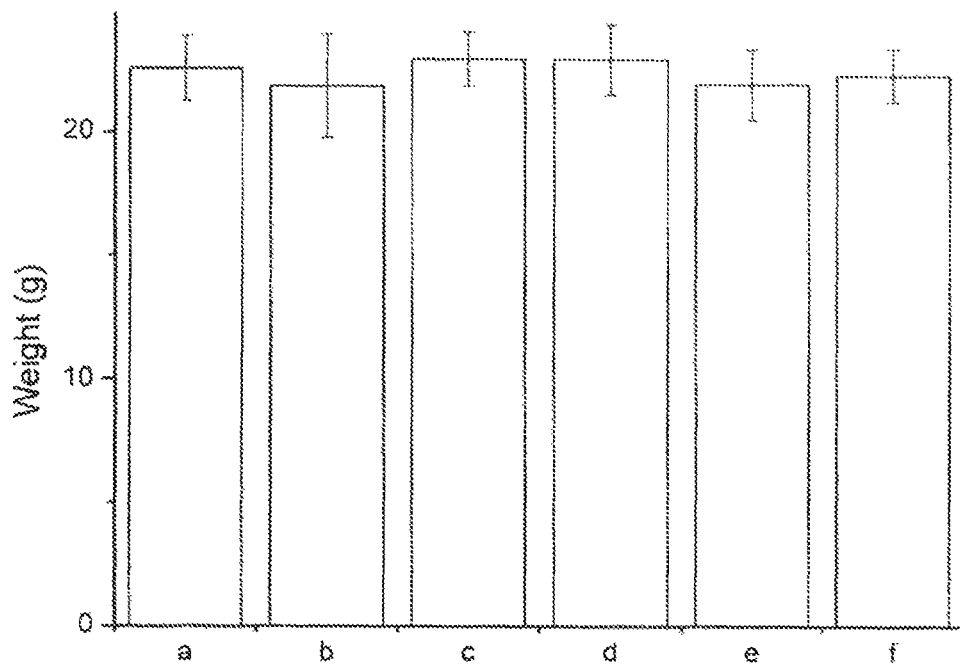
FIG. 6: Body weights at sacrifice (mean±SD). The groups are (a) vehicle, (b) VAL001 0.04 mg/kg, (c) VAL001 0.4 mg/kg, (d) VAL001 4 mg/kg, (e) VAL001 10 mg/kg and (f) VAL001 20 mg/kg. The results of VAL001 groups were compared separately with the results of the vehicle group using one-way ANOVA. No statistically significant differences between groups were detected. Figure was prepared from the original data shown in Table 2.
Figure 7:
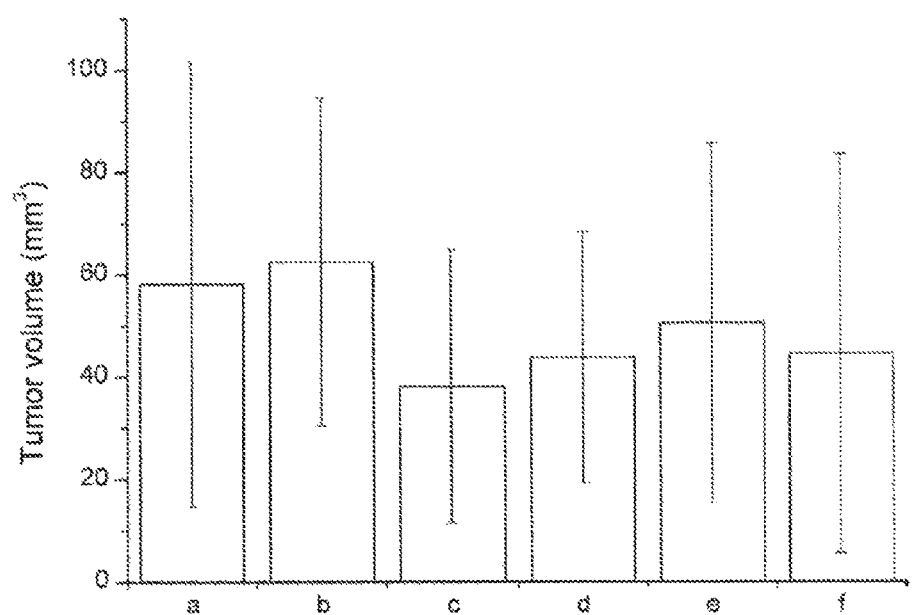
FIG. 7: The tumor volumes at sacrifice (mean±SD). The groups are (a) vehicle, (b) VAL001 0.04 mg/kg, (c) VAL001 0.4 mg/kg, (d) VAL001 4 mg/kg, (e) VAL001 10 mg/kg and (f) VAL001 20 mg/kg. The results of VAL001 groups were compared separately with the results of the vehicle group using one-way ANOVA. No statistically significant differences between groups were detected. Figure was prepared from the original data shown in Table 3.
Figure 8:
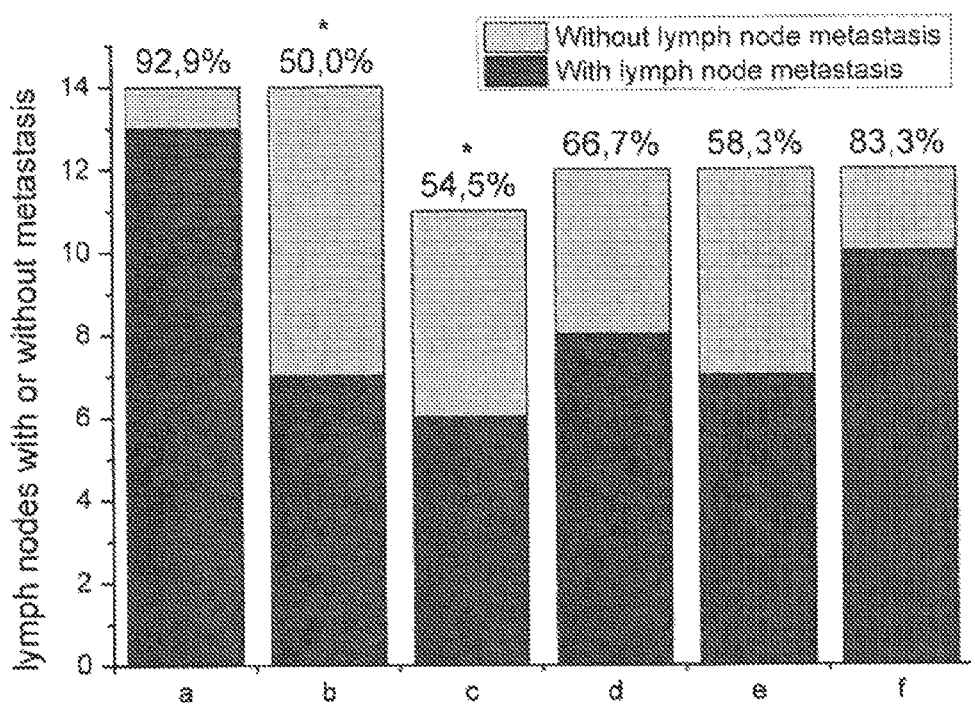
FIG. 8: The incidence of lymph node metastasis. The groups are (a) vehicle, (b) VAL001 0.04 mg/kg, (c) VAL001 0.4 mg/kg, (d) VAL001 4 mg/kg, (e) VAL001 10 mg/kg and (f) VAL001 20 mg/kg. The results of VAL001 groups were compared separately with the results of the vehicle group using Fisher's exact test. There were statistically significantly less metastasis in the groups VAL001 0.04 mg/kg and VAL001 0.4 mg/kg compared with vehicle group (VAL001 0.04 mg/kg $p=0.01643$ and VAL001 0.4 mg/kg $p=0.03913$). Figure was prepared from the original data shown in Table 4.

HT1080 cells harbour a transcriptional incompetent AR that neither trans-locates into nuclei (FIGS. 2 and 4), nor mediates DNA synthesis upon challenging with the synthetic androgen R1881 or DHT (FIG. 2). This is reminiscent of findings observed in NIH3T3 mouse embryo fibroblasts (FIGS. 2 and 4, 16). Both cell lines, however, respond to androgen stimulation with increased motility (FIGS. 2 and 4).

We verified the role of AR in human sarcoma growth by establishing HT1080 xenografts in male immune-depressed mice. The xenograft growth was followed for 4 weeks (FIG. 1). During this time frame, the tumor mass significantly increased in control mice, whereas the growth was reduced in mice treated with the pure androgen antagonist, Casodex. To date, this is the first evidence that targeting AR inhibits human fibrosarcoma growth.

Since androgen does not increase DNA synthesis of HT1080 cells (FIG. 2) and these cells express a large amount of EGFR (FIG. 3A) we hypothesized that inhibition of fibrosarcoma growth by Casodex might be caused by its interference in a crosstalk between EGF and AR signalling. Such a crosstalk has been previously observed in LNCaP cells challenged with EGF (7). To address this issue, we analyzed the effect of a proline-rich peptide (S1 peptide) on various biological effects induced by EGF in HT1080 cells. The S1 peptide derives from the 377-386 amino-acid AR sequence, which is responsible for AR association with Src-SH3 domain and competes for this association as observed in androgen-challenged prostate cancer LNCaP cells (10). In HT1080 cells EGF treatment induces EGFR association with AR and Src (FIG. 3A). The S1 peptide abolishes the AR/Src association as well as the AR/Src association with EGF-R, which likely depends on Src activity of the AR/Src complex (7). In support of this model, the S1 peptide interferes in Src activation (FIG. 3B). The strong EGF stimulation of Src activity is almost completely abolished by 1 nM S1 peptide. Such an inhibition is comparable to that observed by treatment of cells with 10 µM Casodex. The S1 peptide also inhibits the EGF-triggered DNA synthesis (FIG. 3C). The scrambled peptide (Ss peptide) having the same composition of the S1 peptide, but a completely different sequence, was used as a control. It only slightly affects the EGF/AR/Src association (FIG. 3A) and does not reduce Src activation (FIG. 3B) or DNA synthesis (FIG. 3C) in EGF-stimulated cells. These results show that EGF triggers DNA synthesis through EGFR/AR/Src association and Src activation in HT1080 cells. The S1 peptide competing for AR/SRc association prevents EGF action.

Matrix metallo-proteinases (MMPs) expression and activation allows migration and invasiveness, thus playing a crucial role in tumor progression (17). MMP-9 is a member of the MMPs family and HT1080 cells have been used as a model to study its regulation (18). EGF stimulates MMP-9 secretion from HT1080 cells and like Casodex, the S1 peptide inhibits this effect (FIG. 4A). The Ss peptide shows an inhibitory effect on MMP-9 secretion although this effect is much weaker than that exerted by the S1 peptide (FIG. 4A).

Finally, EGF increases the motility of HT1080 cells and this effect is inhibited at a similar extent by Casodex and S1 peptide, but not by Ss peptide (FIGS. 4, B and C).

Discussion

An increasing number of non-reproductive and human cancer cells express SRs. These findings draw the interest on the role of SRs in human proliferative diseases because of their potential therapeutic implications. Human colon carcinoma Caco-2 cells express estradiol receptor (ER) alpha and respond to estradiol with Src activation and proliferation. Anti-estrogens inhibit these effects (19). Estrogens play a role in lung carcinogenesis as initially suggested by more adverse effect of tobacco smoke in women as well as expression of ER (beta and alpha) in human non-small cell lung cancer cells and primary cultures of normal bronchial epithelium. Estrogens stimulate the growth of the non-small cell lung tumor line xenografts in mice and the pure anti-estrogen ICI 182,780 blocks this effect (20). Additional findings on the role of estrogens in human lung cancer development have been also reported (21).

The work presented herein investigates the role and regulation of AR during fibrosarcoma progression. In spite of the absence of mitogenic response of HT1080 cultured cells to androgen, Casodex inhibits the growth of HT1080 xenografted cells. This suggests that AR-dependent proliferation might be regulated by growth factors in HT1080 cells, as observed in human prostate cancer-derived LNCaP cells (7). In these cells, inhibition of androgen- or EGF-induced Src association with AR by Casodex or the AR-derived S1 peptide suppresses Src activation and mitogenesis in cultured cells (7, 10). Together with an ER alpha-derived peptide interfering in ER alpha/Src-SH2 domain association (22), the S1 peptide represents a prototype of a new category of receptor antagonists that target non-transcriptional action of SRs and leave unaffected their transcriptional action. Such a selective inhibition should spare the positive effects dependent on receptor transcriptional action and therefore should be better tolerated by patients.

Tumor progression requires acquisition of invasive phenotype involving MMP production and motility. Migration and MMP-09 secretion from HT1080 cells are also stimulated by EGF and inhibited by the S1 peptide as a consequence of the role of Src in regulating multiple processes in EGF-stimulated HT1080 cells. Therefore, targeting AR/Src association inhibits different properties that are crucial for cancer progression. The increasing number of human cancers expressing steroid receptors and responding to steroids and/or growth factors should enhance the number of tumors which might draw benefit from advances in the therapy of classic hormone-dependent cancers.

REFERENCES

1. Chauduri, P. K., M. J. Walker, C. W. Beattie and T. K. Das Gupta (1980) Presence of steroid receptors in human soft tissue sarcomas of diverse histological origin. *Cancer Res.* 40, 861-865.
2. Chauhan, S, S. Kunz, K. Davis, J. Roberts, G. Martin, M. C. Demetriou, T. C. Sroka, A. E. Cress and R. L. Miesfeld (2004) Androgen control of cell proliferation and cytoskeletal reorganization in human fibrosarcoma cells. *J. Biol. Chem.* 279, 937-944.
3. Castoria G, D'Amato L, Ciociola A, Giovannelli P, Giraldi T, et al (2011) Androgen-induced cell migration: role of androgen receptor/filamin A association. PLoSOne; 6, e17218.
4. Vanderschueren D, Gaytant J. Boonen S, Venken K (2008) Androgens and bone. *Curr Opin Endocrinol Diabetes Obes* 3, 250-254.
5. Migliaccio A, Castoria G, Auricchio F (2011) Analysis of androgen receptor rapid actions in cellular signalling pathways: receptor/Src association. *Methods Mol Biol.* 776, 361-370.
6. Migliaccio A, Castoria G, Giovannelli P, Auricchio F (2010) Cross talk between epidermal growth factor (EGF) receptor and extra nuclear steroid receptors in cell lines. *Mol Cell Endocrinol* 327, 19-24.
7. Migliaccio A, Di Domenico M, Castoria G, Nanayakkara M, Lombardi M, de Falco A, Bilancio A, Varricchio L, Ciociola A, Auricchio F (2005) Steroid receptor regulation of epidermal growth factor signalling through Src in breast and prostate cancer cells: steroid antagonist action. *Cancer Res* 65, 10585-10593.
8. Chang, C. S., J. Kokontis and S. T. Liao (1988) Structural analysis of complementary DNA and amino acid sequences of human and rat androgen receptors. *Proc Natl Acad Sci USA* 85, 7211-7215.
9. Verrijdt, G., E. Schoenmakers, A. Haelens, B. Peeters, G. Verhoeven, W. Rombauts and F. Claessens (2000) Change of specificity mutations in androgen-selective enhancers. Evidence for a role of differential DNA binding by the androgen receptor. *J. Biol. Chem.* 275, 12298-12305.
10. Migliaccio, A., L. Varricchio, A. De Falco, G. Castoria, C. Arra, H. Yamaghuchi, A. Ciociola, M. Lombardi, R. Di Stasio, A. Barbieri, A. Baldi, M. V. Barone, E. Appella and F. Auricchio (2007) Inhibition of the SH3 domain-mediated binding of Src to the androgen receptor and its effect on tumor growth. *Oncogene* 26, 6619-6629.
11. Castoria G, Giovannelli P, Lombardi M, De Rosa C, Giraldi T, de Falco A, Barone M V, Abbondanza C, Migliaccio A, Auricchio F (2012) Tyrosine phosphorylation of estradiol receptor by Src regulates its hormone-dependent nuclear export and cell cycle progression in breast cancer cells. *Oncogene* 31, 4868-4877.
12. Knight C G, Willenbrock F, Murphy G (1992) A novel coumarin-labelled peptide for sensitive continuous assays of the matrix metalloproteinases. *FEBS Lett* 296, 263-266.
13. Smith M M, Shi L, Navre M (1995) Rapid identification of highly active and selective substrates for stromelysin and matrilysin using bacteriophage peptide display libraries. *J. Biol Chem* 270, 6440-6449.
14. Lombardi, M., G. Castoria, A. Migliaccio, M. V. Barone, R. Di Stasio, A. Ciociola, D. Bottero, H. Yamaguchi, E. Appella and F. Auricchio (2008) Hormone-dependent nuclear export of estradiol receptor and DNA synthesis in breast cancer cells. *J CellBiol.* 182, 327-340.
15. Migliaccio, A., G. Castoria, M. Di Domenico, A. de Falco, A. Bilancio, M. Lombardi, M. V. Barone, D. Ametrano, M. S. Zannini, C. Abbondanza and F. Auricchio (2000) Steroid-induced androgen receptor-oestradiol receptor beta-Src complex triggers prostate cancer cell proliferation. *EMBO J.* 19, 5406-5417.
16. Castoria, G., M. Lombardi, M. V. Barone, A. Bilancio, M. Di Domenico, D. Bottero, F. Vitale, A. Migliaccio and F. Auricchio (2003) Androgen-stimulated DNA synthesis and cytoskeletal changes in fibroblasts by a nontranscriptional receptor action. *J. Cell Biol.* 161, 547-556.
17. McCawley L J, Matrisian L M (2001) Matrix metalloproteinases: they're not just for matrix anymore! *Curr Opin Cell Biol.* 13, 534-540.
18. Partridge J J, Madsen M A, Ardi V C, Papagiannakopoulos T, Kupriyanova T A, Quigley J P, Deryugina El (2007) Functional analysis of matrix metalloproteinases and tissue inhibitors of metalloproteinases differentially expressed by variants of human HT-1080 fibrosarcoma exhibiting high and low levels of intravasation and metastatis. *J Biol Chem* 282, 35964-35977.
19. Di Domenico M, Castoria G, Bilancio A, Migliaccio A, Auricchio F (1996) Estradiol activation of human colon carcinoma-derived Caco-2 cell growth. *Cancer Res.* 56, 4516-4521.
20. Stabile L P, Davis A L, Gubish C T, Hopkins T M, Luketich J D, Christie N, Finkelstein S, Siegfried J M (2002) Human non-small cell lung tumors and cells derived from normal lung express both estrogen receptor alpha and beta and show biological responses to estrogen. *Cancer Res.* 62, 2141-2150.
21. Bogush T A, Dudko E A, Berne A A, Bogush E A, Kim Al, Polotsky B E, Tjuljandin S A, Davydov M I (2010) Estrogen receptors, antiestrogens, and non-small cell lung cancer. *Biochemistry (Mosc)* 75, 1421-1427.
22. Varricchio L., A. Migliaccio, G. Castoria, H. Yamaguchi, A. de Falco, M. Di Domenico, P. Giovannelli, W. Farrar, E. Appella and F. Auricchio (2007) Inhibition of Estradiol Receptor/Src Association and Cell Growth by an Estradiol Receptor {alpha}Tyrosine-Phosphorylated Peptide. *Mol. Cancer Res.* 11, 1213-1221.

EXAMPLE 2: THE EFFECT OF FIVE DOSES OF TEST PEPTIDE ON TUMOR GROWTH AND METASTASES ON ORTHOTOPIC PC-3 PROSTATE CANCER MODEL

Summary

The objective of this project was to study effects of five doses of test peptide on prostate tumor growth and development of lymph node metastases.

Six week-old immunodeficient BALB/c nude mice were allocated to six 15-mice groups according to the body weight. PC-3 cells were inoculated orthotopically into prostates of the mice. Dosing (s.c.) was started at study day 1 and continued daily for 28 days.

Study Groups:
1. Control group receiving vehicle
2. VAL001 peptide, 0.04 mg/kg
3. VAL001 peptide, 0.4 mg/kg
4. VAL001 peptide, 4 mg/kg
5. VAL001 peptide, 10 mg/kg
6. VAL001 peptide, 20 mg/kg Mice were weighed twice a week, and after 4 weeks, mice were sacrificed. Gross necropsy was performed to all animals at the end of the study, and all macroscopic signs were recorded. Volume of the prostate tumors was measured and prostate as well as prostate draining lymph nodes were collected for histology. The number of metastasis in lymph nodes was determined under microscope.

VAL001 peptide inhibited statistically significantly lymph node metastasis incidence with two smallest doses 0.04 mg/kg and 0.4 mg/kg. There were no statistically significant differences in the body weights or tumor volumes between the treatment groups.

Overall these results suggest that VAL001 peptide has inhibitory effects on lymph node metastases in this orthotopic PC-3 prostate cancer model.

Conduct of Research
Testing Facility

The project was conducted at the Laboratory of Pharmatest Services Ltd, Itainen Pitkakatu 4 C, 20520 Turku, Finland. Animal experiments were conducted at the Biolaboratory of Turku Biovalley, Itainen Pitkakatu 4 A, 20520 Turku, Finland with the approval of the National Committee for Animal Experiments (license number STH332A).

Quality Assurance

This study was performed according to a quality assurance system and standard operating procedures. All work was performed with highest scientific accuracy and know-how. All study specific conditions that may affect primary data were monitored throughout the study. All work was recorded in designated laboratory books with each page sequentially numbered. The following basic GLP principles were followed throughout the study:

- All data and other study file entries are clearly identified at the time of entry with the Study number and any information necessary to identify the type of data. All entries are signed and the date and time of entry is stamped by the person making the entry.
- Any data corrections, additions or deletions are accompanied by the reason for the change, the signature of the person making the change, and the date and time that the change was made.
- A table is prepared in advance of each step in an experiment to indicate for each test sample, its position in the incubation plates, and its appropriate analyser sample reference number.
- A comprehensive log of file notes will be maintained to document any deviations from the agreed protocol and the steps taken to investigate any discrepancies in the data (e.g. failed runs, the addition of extra replicates etc.).
- Any deviations from the original protocol shall be described in detail in the final report, including description of how the experiment was supposed to be performed according to the original protocol, how it was performed, and what was the reason for the deviation.

Test Compounds and Vehicles
Test Peptide

One peptide, VAL001 (Ac-PPPHPHARIK-NH2 (SEQ ID. NO.: 22) where Ac is an acetyl group), was included in the study:
(1) VAL001, molecular weight=1190 g/mol The 0.01 mg/ml, 0.1 mg/ml, 1 mg/ml, 2.5 mg/ml and 5 mg/ml dosing suspensions were prepared from test peptide VAL001 by dilution to PBS. The dosing suspensions from test peptide were administered s.c. once a day from day 1 to day 28 at a volume of 4 ml/kg, resulting as doses of 0.04 mg/kg, 0.4 mg/kg, 4 mg/kg, 10 mg/kg and 20 mg/kg. New dosing suspensions were prepared every week.

Vehicle

Vehicle was PBS. The vehicle was administered s.c. once a day from day 1 to day 28 at a volume of 4 ml/kg.

Description of the Test System Used

Patients with prostate cancer typically develop metastases to regional prostate draining lymph nodes. Almost all prostate cancer patients with end-stage disease have metastases. Although the primary tumor could be successfully removed, the disease may have already spread to lymph nodes, where from it can further spread systemically.

An animal model was used that can be effectively used for testing the effects of cancer drug candidates on the primary tumor growth in prostate microenvironment. In this model, human prostate cancer cells are inoculated into prostate of 4-5 week old male BALB/c nude mice. This mouse strain is immunodeficient, allowing rapid growth and spread of the human cancer cells. Within four weeks after the inoculation, animal develop large tumor to prostate and metastases to regional iliac and sacral lymph nodes. The animals are sacrificed at 4 weeks after inoculation, and their prostate with tumor and regional lymph nodes are collected for further histomorphometric analysis.

The metastasis model can be conveniently used to test drug candidates that have been shown in preliminary studies to affect one or more of the following: 1) growth of cancer cells; 2) angiogenesis; 3) function or differentiation of osteoclasts. The model can also be used for finding new indications to existing drugs, allowing the pharmaceutical companies a way of finding new indications to patented drugs that have already proved efficient in some other indications.

Methods
Animal Handling

The in-life phase of the study was performed by Pharmatest under animal experiment license STH332A granted by Animal Experiment Board, Regional State Administrative Agency for Southern Finland, Hameenlinna, Finland. The in-life phase included animal housing and handling, body weight determination, dosing, termination, and harvesting tissue samples. The in-life phase was performed by partnering with Turku Science Park Ltd, Turku, Finland.

Male BALB/c nude mice (BALB/c OlaHsd-Foxn1$^{nu}$, obtained from Harlan, The Netherlands) were used for this study. The age of the animals was 6-7 weeks, and their body weights were approximately 16-23 g at the beginning of the study. The mice were specific pathogen free (SPF) and isolator-reared animals. Correct age and good clinical health were qualifications for the study. The acclimatization period for the mice was 4 days. Allocation to groups was performed by randomization procedure based on body weight. The animals were marked with ear marks. For orthotopic inoculations the mice were anesthetized with inhalation of isoflurane. Analgesia was provided before and 2 days after the orthotopic inoculation with buprenorphine: 0.1 mg/kg, s.c.

Animal Monitoring

The animals were weighed twice a week. For the last 5 days of the study, the animals were observed daily to monitor the progression of disease. Appearance of any clinical signs was recorded on follow-up forms. Analgesic was given if needed.

Sacrifice, Autopsy and Sample Collection

At the end of the study, the animals were weighed and sacrificed with cervical dislocation under anesthesia. Necropsy was carried out in all animals. Macroscopic findings were recorded on the follow-up forms. Tissue samples from prostate with tumor and lymph nodes were collected for histology and number of metastases in lymph nodes was determined.

Statistical Analysis

Statistical analysis was performed with R: A Language and Environment for Statistical Computing (version 2.14.2; R Development Core Team, Vienna, Austria). The mean and standard deviation of the body weights and the tumor volumes at sacrifice were determined. Normality of the distributions and homogeneity of variance were checked before further analyses. In case of violating these assumptions, either log transformation or other appropriate transformation (e.g. square root, reciprocal) was applied. If the assumptions were fulfilled as such or after transformation, one-way ANOVA was used to study if the values obtained between the groups were statistically different (with $p<0.05$). If differences were found, Tukey's HSD test was used for pairwise comparison between all groups. If the assumptions were not fulfilled even after the transformations described above, the non-parametric Kruskal-Wallis test followed by Mann-Whitney U-test were used.

The statistical analysis of incidence of lymph node metastases was done using Fisher's exact test as one-sided test in which the null hypothesis reflected the assumption that the treatment suppresses tumor growth.

Results

The results relating to body weight, tumour volume at sacrifice and lymph node metastases are shown in FIGS. 5-8. The following conclusions can be drawn:

- There were no statistically significant differences in the body weights or tumor volumes between the treatment groups.
- VAL001 peptide inhibited statistically significantly lymph node metastasis incidence with two smallest doses 0.04 mg/kg and 0.4 mg/kg.

Overall these results suggest that VAL001 peptide has inhibitory effects on lymph node metastases in this orthotopic PC-3 prostate cancer model Tables

TABLE 1

Body weights during the study.

|      | day −1 | day 2 | day 5 | day 7 | day 9 | day 12 | day 14 | day 16 | day 19 | day 21 | day 23 | day 26 | day 29 |
|------|--------|-------|-------|-------|-------|--------|--------|--------|--------|--------|--------|--------|--------|
| 1.1  | 18.7 | 21.6 | 23.1 | 23.0 | 23.1 | 23.8 | 23.3 | 23.5 | 22.1 | 23.1 | 23.3 | 23.6 | 22.1 |
| 1.2  | 19.3 | 21.5 | 22.5 | 22.2 | 22.6 | 23.9 | 24.5 | 24.3 | 23.0 | 23.5 | 24.3 | 24.8 | 23.8 |
| 1.3  | 19.3 | 20.7 | 22.2 | 22.7 | 22.8 | 24.9 | 25.2 | 25.4 | 25.1 | 23.9 | 24.4 | 24.7 | 25.2 |
| 1.4  | 19.7 | 22.5 | 24.0 | 24.0 | 23.4 | 24.4 | 24.2 | 24.6 | 24.1 | 23.9 | 23.8 | 23.4 | 19.9 |
| 1.5  | 20.4 | 22.3 | 21.9 | 21.9 | 21.9 | 23.3 | 24.3 | 24.1 | 24.0 | 23.8 | 24.4 | 24.6 | 21.5 |
| 1.6  | 20.5 | 23.0 | 23.9 | 24.9 | 24.8 | 26.1 | 26.4 | 26.2 | 24.9 | 24.9 | 24.5 | 23.8 | 24.6 |
| 1.7  | 21.8 | 24.6 | 25.2 | 24.9 | 24.4 | 24.9 | 24.9 | 25.1 | 25.0 | 25.6 | 25.6 | 24.5 | 24.5 |
| 1.8  | 21.8 | 23.0 | 23.3 | 23.7 | 24.0 | 24.9 | 25.4 | 25.0 | 24.3 | 24.2 | 24.9 | 25.9 | 25.4 |
| 1.9  | 23.6 | 25.5 | 25.9 | 26.4 | 26.2 | 26.2 | 26.1 | 25.4 | 24.7 | 24.7 | 26.1 | 25.3 | 24.3 |
| 2.1  | 17.4 | 20.5 | 21.5 | 21.2 | 21.7 | 22.2 | 22.7 | 22.8 | 22.2 | 21.6 | 22.3 | 23.2 | 22.7 |
| 2.2  | 18.4 | 20.7 | 22.0 | 22.1 | 23.3 | 24.4 | 24.9 | 24.8 | 23.8 | 23.8 | 24.7 | 25.1 | 24.5 |
| 2.3  | 19.2 | 22.1 | 23.3 | 23.1 | 23.3 | 23.9 | 24.4 | 24.5 | 22.8 | 22.8 | 24.0 | 24.5 | 24.3 |
| 2.4  | 19.3 | 21.8 | 23.8 | 22.9 | 23.4 | 24.5 | 24.5 | 24.7 | 23.4 | 23.0 | 23.5 | 23.9 | 23.5 |
| 2.5  | 19.7 | 21.2 | 22.8 | 23.3 | 24.1 | 24.9 | 24.8 | 24.6 | 23.6 | 23.6 | 24.3 | 24.7 | 25.1 |
| 2.6  | 19.8 | 22.3 | 22.9 | 23.6 | 23.3 | 23.9 | 24.3 | 23.9 | 22.6 | 22.8 | 23.5 | 23.6 | 22.8 |
| 2.7  | 20.6 | 23.2 | 24.0 | 23.6 | 22.9 | 23.8 | 23.8 | 24.6 | 23.4 | 24.3 | 25.3 | 25.2 | 24.2 |
| 2.8  | 21.7 | 23.3 | 23.7 | 24.3 | 23.8 | 24.3 | 23.9 | 24.3 | 23.3 | 23.3 | 24.1 | 23.9 | 23.1 |
| 2.9  | 22.0 | 23.7 | 24.9 | 25.0 | 25.3 | 27.8 | 27.7 | 27.6 | 26.8 | 27.3 | 27.8 | 28.3 | 27.7 |
| 2.10 | 22.9 | 23.8 | 24.0 | 24.2 | 24.3 | 26.8 | 26.7 | 27.1 | 26.3 | 26.5 | 26.9 | 26.6 | 25.5 |
| 3.1  | 18.9 | 20.7 | 21.4 | 22.1 | 22.2 | 23.7 | 24.2 | 24.3 | 23.5 | 23.4 | 24.0 | 25.1 | 24.6 |
| 3.2  | 19.2 | 20.9 | 21.6 | 22.4 | 22.6 | 24.0 | 24.2 | 24.5 | 23.3 | 23.3 | 23.9 | 25.2 | 24.7 |
| 3.3  | 19.4 | 21.7 | 22.9 | 22.2 | 22.0 | 22.6 | 22.8 | 23.0 | 22.2 | 22.4 | 23.1 | 23.4 | 22.5 |
| 3.4  | 19.7 | 21.2 | 22.1 | 22.2 | 22.3 | 24.0 | 24.3 | 25.2 | 24.2 | 24.4 | 25.1 | 25.6 | 26.3 |
| 3.5  | 19.8 | 21.9 | 22.8 | 23.5 | 23.8 | 25.3 | 25.5 | 25.1 | 24.7 | 24.7 | 25.4 | 25.6 | 24.6 |
| 3.6  | 20.3 | 22.2 | 23.2 | 23.4 | 23.3 | 25.1 | 25.3 | 24.7 | 23.5 | 23.8 | 24.6 | 25.3 | 24.0 |
| 3.7  | 20.6 | 23.1 | 23.9 | 25.3 | 25.7 | 26.9 | 27.2 | 26.6 | 25.5 | 26.2 | 27.0 | 26.8 | 26.3 |
| 3.8  | 21.7 | 23.4 | 23.8 | 24.6 | 24.5 | 25.1 | 25.1 | 24.6 | 24.9 | 25.0 | 25.8 | 25.9 | 24.3 |
| 3.9  | 22.2 | 24.7 | 25.3 | 25.9 | 26.3 | 27.9 | 28.4 | 27.8 | 26.9 | 27.5 | 27.8 | 27.8 | 26.4 |
| 3.10 | 22.8 | 24.5 | 24.5 | 25.0 | 24.7 | 25.8 | 26.3 | 25.8 | 25.1 | 25.1 | 26.7 | 26.6 | 25.3 |
| 4.1  | 17.8 | 20.6 | 22.4 | 21.8 | 22.7 | 23.8 | 23.9 | 24.4 | 23.7 | 23.5 | 23.8 | 23.9 | 24.4 |
| 4.2  | 18.1 | 19.7 | 21.0 | 20.2 | 19.4 | 20.1 | 20.0 | 20.5 | 20.7 | 20.1 | 20.5 | 20.6 | 20.9 |
| 4.3  | 18.9 | 21.1 | 23.4 | 23.5 | 23.4 | 24.9 | 25.1 | 24.6 | 24.9 | 24.4 | 25.6 | 25.4 | 25.5 |
| 4.4  | 19.0 | 20.4 | 21.0 | 20.8 | 20.7 | 22.0 | 22.7 | 22.6 | 22.8 | 21.9 | 22.0 | 21.3 | 22.4 |
| 4.5  | 19.4 | 21.7 | 22.4 | 22.9 | 22.4 | 23.6 | 23.6 | 23.7 | 22.7 | 22.5 | 23.3 | 23.1 | 21.6 |
| 4.6  | 20.1 | 22.9 | 23.7 | 24.6 | 24.3 | 25.6 | 25.9 | 25.9 | 24.5 | 25.2 | 26.2 | 26.4 | 25.5 |
| 4.7  | 20.7 | 23.0 | 23.7 | 24.8 | 25.5 | 27.0 | 26.7 | 26.6 | 24.3 | 23.1 | 23.3 | 23.2 | 24.5 |
| 4.8  | 21.2 | 23.5 | 25.6 | 24.3 | 24.6 | 25.4 | 25.1 | 25.3 | 25.5 | 24.0 | 25.3 | 25.5 | 26.0 |
| 4.9  | 22.3 | 25.0 | 25.8 | 25.7 | 25.8 | 26.9 | 27.4 | 28.2 | 28.2 | 27.1 | 27.8 | 28.4 | 29.1 |
| 4.10 | 22.8 | 25.0 | 26.1 | 25.5 | 25.6 | 26.5 | 27.1 | 27.2 | 26.3 | 25.5 | 26.8 | 26.8 | 27.8 |
| 5.1  | 18.0 | 19.4 | 21.6 | 21.8 | 22.1 | 23.7 | 24.3 | 24.8 | 24.1 | 23.3 | 24.1 | 24.0 | 24.4 |
| 5.2  | 18.9 | 21.3 | 22.6 | 22.6 | 22.8 | 24.4 | 25.3 | 25.0 | 24.0 | 24.1 | 24.5 | 25.1 | 24.8 |
| 5.3  | 19.4 | 22.5 | 25.7 | 26.7 | 26.9 | 28.9 | 29.3 | 29.7 | 29.9 | 28.4 | 28.3 | 28.0 | 27.9 |
| 5.4  | 19.5 | 20.9 | 22.9 | 22.6 | 22.4 | 23.2 | 23.5 | 24.4 | 24.7 | 23.9 | 24.7 | 24.3 | 25.5 |
| 5.5  | 20.0 | 21.6 | 24.0 | 24.6 | 24.9 | 27.2 | 27.2 | 27.3 | 27.2 | 26.3 | 26.0 | 25.3 | 24.8 |

TABLE 1-continued

Body weights during the study.

| | day −1 | day 2 | day 5 | day 7 | day 9 | day 12 | day 14 | day 16 | day 19 | day 21 | day 23 | day 26 | day 29 |
|---|---|---|---|---|---|---|---|---|---|---|---|---|---|
| 5.6 | 20.1 | 22.5 | 23.6 | 23.1 | 23.8 | 24.9 | 24.9 | 24.5 | 25.3 | 24.7 | 23.7 | 20.7 | 21.8 |
| 5.7 | 20.8 | 21.6 | 22.8 | 23.3 | 24.0 | 25.0 | 24.7 | 24.2 | 23.7 | 23.9 | 24.8 | 25.5 | 24.4 |
| 5.8 | 21.0 | 22.7 | 23.0 | 23.5 | 23.8 | 25.7 | 27.2 | 27.3 | 26.1 | 25.6 | 26.7 | 27.7 | 26.8 |
| 5.9 | 22.5 | 23.6 | 25.5 | 25.6 | 25.7 | 26.9 | 27.6 | 28.5 | 27.8 | 27.3 | 27.8 | 29.0 | 27.7 |
| 5.10 | 22.7 | 24.7 | 24.5 | 23.1 | 23.7 | 25.5 | 26.0 | 26.4 | 25.8 | 25.7 | 26.9 | 27.7 | 27.2 |

TABLE 2

The study day of maximum body weight obtained. Statistical analysis was performed using Kruskal-Wallis test. No statistical differences were observed (p = 0.7369).

| | Vehicle | 0.004 mg/kg | 0.04 mg/kg | 0.4 mg/kg | 4 mg/kg |
|---|---|---|---|---|---|
| 1 | 12 | 26 | | 16 | 16 |
| 2 | 26 | 26 | 26 | 5 | 14 |
| 3 | 16 | 16 | 26 | 23 | 19 |
| 4 | 16 | 16 | 29 | 19 | 29 |
| 5 | 26 | 29 | 26 | 16 | 16 |
| 6 | 14 | 14 | 14 | 26 | 19 |
| 7 | 21 | 23 | 14 | 12 | 26 |
| 8 | 26 | 7 | 26 | 29 | 26 |
| 9 | 7 | 26 | 14 | 29 | 26 |
| 10 | NA | 16 | 23 | 29 | 26 |
| mean | 18 | 20 | 22 | 20 | 22 |
| std | 7 | 7 | 6 | 8 | 5 |

TABLE 3

Body weight at sacrifice relative to maximum weight. Statistical analysis was performed using Kruskal-Wallis test. No statistical differences were observed (p = 0.12259).

| | Vehicle | 0.004 mg/kg | 0.04 mg/kg | 0.4 mg/kg | 4 mg/kg |
|---|---|---|---|---|---|
| 1 | 92.9 | 97.8 | 98.0 | 100.0 | 98.4 |
| 2 | 96.0 | 97.6 | 98.0 | 99.5 | 98.0 |
| 3 | 99.2 | 99.2 | 96.2 | 99.6 | 93.3 |
| 4 | 80.9 | 95.1 | 100.0 | 98.2 | 100.0 |
| 5 | 87.4 | 100.0 | 96.1 | 91.1 | 90.8 |
| 6 | 93.2 | 93.8 | 94.9 | 96.6 | 86.2 |
| 7 | 95.7 | 95.7 | 96.7 | 90.7 | 95.7 |
| 8 | 98.1 | 95.1 | 93.8 | 100.0 | 96.8 |
| 9 | 92.0 | 97.9 | 93.0 | 100.0 | 95.5 |
| 10 | NA | 94.1 | 94.8 | 100.0 | 98.2 |
| mean | 92.8 | 96.6 | 96.1 | 97.6 | 95.3 |
| std | 5.7 | 2.2 | 2.1 | 3.7 | 4.2 |

TABLE 4

Total tumor volumes during the study.

| | day 2 | day 5 | day 7 | day 9 | day 12 | day 14 | day 16 | day 19 | day 21 | day 23 | day 26 | day 29 |
|---|---|---|---|---|---|---|---|---|---|---|---|---|
| 1.1 | 36.3 | 43.4 | 33.5 | 61.2 | 75.8 | 118.3 | 133.1 | 210.4 | 267.1 | 284.2 | 3178.8 | 359.7 |
| 1.2 | 17.4 | 26.4 | 21.4 | 54.3 | 41.1 | 92.0 | 135.9 | 165.9 | 237.1 | 266.8 | 409.9 | 288.8 |
| 1.3 | 25.6 | 57.6 | 41.1 | 106.2 | 38.2 | 64.6 | 200.5 | 276.5 | 293.5 | 351.3 | 403.0 | 529.0 |
| 1.4 | 23.4 | 34.7 | 30.5 | 49.5 | 52.0 | 91.6 | 133.3 | 264.7 | 199.8 | 265.7 | 300.8 | 257.4 |
| 1.5 | 13.8 | 29.8 | 33.8 | 56.4 | 73.3 | 114.7 | 172.3 | 300.4 | 330.2 | 505.2 | 530.2 | 465.8 |
| 1.6 | 0.0 | 17.5 | 14.1 | 27.8 | 24.8 | 62.7 | 76.9 | 198.0 | 204.4 | 148.9 | 142.9 | 165.9 |
| 1.7 | 0.0 | 26.8 | 31.9 | 57.4 | 77.1 | 99.7 | 142.2 | 323.3 | 411.8 | 402.2 | 437.5 | 425.3 |
| 1.8 | 27.2 | 25.1 | 17.8 | 26.8 | 29.6 | 58.4 | 64.9 | 120.8 | 108.1 | 126.2 | 178.6 | 180.6 |
| 1.9 | 0.0 | 18.3 | 26.1 | 103.9 | 66.6 | 98.9 | 134.0 | 343.3 | 423.7 | 406.8 | 518.8 | 507.2 |
| 2.1 | 20.2 | 22.3 | 21.1 | 28.2 | 51.3 | 71.8 | 87.7 | 202.0 | 182.3 | 158.4 | 277.2 | 382.9 |
| 2.2 | 11.2 | 11.5 | 7.8 | 18.2 | 20.1 | 55.8 | 70.9 | 163.3 | 152.1 | 95.0 | 233.9 | 204.8 |
| 2.3 | 14.2 | 21.5 | 17.8 | 32.4 | 39.6 | 72.5 | 140.3 | 186.2 | 196.2 | 289.5 | 254.0 | 258.0 |
| 2.4 | 20.2 | 16.9 | 22.0 | 21.3 | 56.1 | 65.8 | 85.4 | 140.9 | 139.5 | 181.8 | 243.7 | 216.8 |
| 2.5 | 9.4 | 26.7 | 16.9 | 29.6 | 24.6 | 54.7 | 62.6 | 104.4 | 120.6 | 127.8 | 239.4 | 245.1 |
| 2.6 | 0.0 | 29.3 | 18.3 | 57.8 | 57.0 | 114.0 | 167.3 | 181.7 | 278.5 | 278.8 | 381.2 | 418.0 |
| 2.7 | 22.0 | 27.8 | 31.2 | 76.4 | 116.3 | 176.1 | 183.2 | 332.0 | 365.1 | 386.3 | 618.5 | 750.0 |
| 2.8 | 47.6 | 29.3 | 29.6 | 34.4 | 70.3 | 106.7 | 112.1 | 227.3 | 240.1 | 323.8 | 328.7 | 430.6 |
| 2.9 | 19.6 | 23.1 | 20.0 | 20.8 | 46.9 | 71.7 | 101.0 | 181.3 | 263.8 | 345.6 | 518.9 | 288.0 |
| 2.10 | 6.3 | 22.7 | 11.6 | 25.7 | 19.4 | 45.2 | 60.3 | 77.5 | 110.5 | 198.0 | 207.1 | 206.5 |
| 3.1 | 12.6 | 9.2 | 6.5 | 25.9 | 20.3 | 19.9 | 39.3 | 77.2 | 102.5 | 145.2 | 171.2 | 174.1 |
| 3.2 | 28.9 | 16.0 | 22.0 | 25.7 | 55.2 | 52.9 | 66.2 | 180.8 | 200.0 | 253.1 | 347.7 | 323.2 |
| 3.3 | 14.7 | 31.1 | 31.9 | 49.4 | 47.7 | 74.1 | 121.1 | 184.3 | 183.6 | 237.9 | 312.1 | 403.0 |
| 3.4 | 20.2 | 31.2 | 14.8 | 37.3 | 13.1 | 14.1 | 30.9 | 77.2 | 86.4 | 183.8 | 192.5 | 230.9 |
| 3.5 | 10.1 | 38.8 | 21.8 | 17.0 | 22.0 | 45.1 | 79.7 | 269.9 | 323.8 | 342.4 | 427.7 | 440.1 |
| 3.6 | 11.5 | 15.6 | 19.5 | 18.3 | 33.2 | 36.4 | 54.5 | 96.9 | 154.4 | 147.6 | 206.7 | 312.7 |
| 3.7 | 21.8 | 30.5 | 22.0 | 20.0 | 31.1 | 36.0 | 66.0 | 179.6 | 173.8 | 237.1 | 237.6 | 117.6 |
| 3.8 | 8.8 | 13.8 | 15.4 | 16.0 | 23.7 | 39.8 | 55.2 | 108.8 | 120.7 | 183.8 | 170.0 | |
| 3.9 | 18.9 | 28.4 | 16.8 | 22.7 | 32.4 | 29.0 | 51.8 | 107.4 | 76.2 | 69.6 | 88.8 | 79.8 |
| 3.10 | 11.0 | 39.0 | 42.4 | 49.5 | 89.7 | 118.6 | 191.1 | 269.1 | 305.3 | 413.3 | 525.8 | 658.6 |
| 4.1 | 19.2 | 42.6 | 31.8 | 51.8 | 37.0 | 59.7 | 62.4 | 174.9 | 178.6 | 254.0 | 252.0 | 311.9 |
| 4.2 | 10.6 | 22.2 | 24.5 | 30.6 | 51.3 | 87.6 | 85.9 | 167.9 | 176.6 | 239.4 | 296.5 | 331.3 |
| 4.3 | 18.4 | 11.7 | 3.6 | 20.3 | 14.1 | 31.1 | 44.9 | 98.3 | 126.7 | 101.4 | 123.9 | 188.5 |
| 4.4 | 8.8 | 20.1 | 23.9 | 39.4 | 40.3 | 97.1 | 106.7 | 229.1 | 194.4 | 282.1 | 249.6 | 295.1 |
| 4.5 | 0.0 | 18.3 | 19.7 | 19.5 | 24.1 | 40.6 | 33.5 | 92.7 | 163.8 | 142.2 | 197.6 | 178.6 |
| 4.6 | 16.8 | 60.3 | 40.7 | 52.5 | 61.4 | 95.7 | 156.4 | 237.4 | 311.7 | 413.3 | 386.3 | 554.5 |
| 4.7 | 10.9 | 22.0 | 14.0 | 18.6 | 23.1 | 25.0 | 34.9 | 106.0 | 71.5 | 99.8 | 97.5 | 123.9 |
| 4.8 | 0.0 | 9.2 | 25.0 | 30.6 | 46.9 | 88.1 | 101.8 | 217.8 | 128.6 | 204.7 | 282.0 | 273.8 |
| 4.9 | 24.3 | 17.0 | 11.4 | 7.7 | 6.6 | 7.9 | 8.0 | 46.5 | 28.1 | 37.3 | 60.7 | 69.1 |

TABLE 4-continued

Total tumor volumes during the study.

|      | day 2 | day 5 | day 7 | day 9 | day 12 | day 14 | day 16 | day 19 | day 21 | day 23 | day 26 | day 29 |
|------|-------|-------|-------|-------|--------|--------|--------|--------|--------|--------|--------|--------|
| 4.10 | 32.5  | 18.4  | 29.6  | 34.4  | 32.2   | 41.8   | 75.6   | 219.5  | 157.2  | 219.4  | 197.2  | 356.4  |
| 5.1  | 23.0  | 31.0  | 22.1  | 21.6  | 34.2   | 48.6   | 87.6   | 150.7  | 123.9  | 124.0  | 161.4  | 261.6  |
| 5.2  | 15.3  | 22.9  | 23.0  | 18.9  | 21.6   | 26.0   | 32.7   | 158.8  | 133.2  | 145.8  | 170.7  | 212.5  |
| 5.3  | 16.8  | 10.5  | 14.1  | 13.8  | 23.1   | 18.3   | 22.2   | 78.7   | 97.5   | 107.2  | 96.0   | 169.9  |
| 5.4  | 13.5  | 20.9  | 18.9  | 22.3  | 52.6   | 70.1   | 107.8  | 233.3  | 234.5  | 274.4  | 356.4  | 501.6  |
| 5.5  | 22.0  | 17.6  | 24.6  | 17.7  | 38.0   | 62.5   | 77.1   | 152.5  | 153.6  | 147.5  | 128.8  | 111.4  |
| 5.6  | 16.8  | 19.9  | 21.0  | 20.4  | 28.8   | 63.5   | 52.7   | 148.8  | 157.1  | 226.8  | 202.3  | 274.4  |
| 5.7  | 0.0   | 16.6  | 14.2  | 24.4  | 36.3   | 41.7   | 43.7   | 116.4  | 120.3  | 156.6  | 188.4  | 173.0  |
| 5.8  | 3.0   | 26.4  | 15.6  | 39.7  | 38.9   | 111.1  | 116.8  | 192.5  | 269.5  | 326.3  | 269.3  | 396.3  |
| 5.9  | 9.7   | 22.7  | 13.5  | 22.1  | 24.9   | 37.7   | 61.2   | 174.2  | 186.5  | 250.5  | 358.7  | 320.0  |
| 5.10 | 0.0   | 31.0  | 8.2   | 41.5  | 38.6   | 83.0   | 89.8   | 150.7  | 158.1  | 287.8  | 261.9  | 266.6  |

REFERENCES

Johanna Tuomela, Maija Valta, Jani Seppanen, H. Kalervo Vaananen, and Pirkko Harkonen. Overexpression of vascular endothelial growth factor C increases growth and alters the metastatic pattern of orthotopic PC-3 prostate tumors. BMC Cancer 2009.

Maija P. Valta, Johanna Tuomela, Heikki Vuorikoski, Niina Loponen, Riina-Minna Vaananen, Kim Petterson, H. Kalervo Vaananen, Pirkko L. Harkonen. FGF8b induces growth and rich vascularization in an orthotopic PC-3 model of prostate cancer. J. Cell Biochem 2009.

Johanna M. Tuomela, Maija P. Valta, H. Kalervo Vaananen and Pirkko L. Harkonen. Alendronate Decreases Orthotopic PC-3 prostate Tumor Growth and metastasis to Prostate draining Lymph Nodes in Nude Mice. BMC Cancer. 2008

EXAMPLE 3: THE PEPTIDE AC-PPPHPHARIK-NH2 (SEQ ID. NO.: 22) EXHIBITS THERAPEUTIC EFFICACY AGAINST ENDOMETRIOSIS WITHOUT AFFECTING FERTILITY

Summary

Two studies have been carried out which demonstrate the efficacy of the peptide Ac-PPPHPHARIK-NH2 (SEQ ID. NO.: 22) (also defined in Tables 5-8 as ValiRx1) in treating endometriosis without reducing fertility.

Results

In a first study, a total of 4 treatment and 5 control animals were generated in a novel in-vivo model of endometriosis (Research Horizons, University of Cambridge, 2009 Issue 8, GB 0715635.9) K-rasV12/Ah-Cre transgenic mice were crossed with Rosa26R mice to generate KrasV12+/−/Ah-Cre+/−/ROSA26R-LacZ+/− transgenic mice. The F1 offspring were inbred to generate F2 K-rasV12+/−/Ah-Cre+/+/ ROSA26R-LacZ+/+ transgenic mice. The presence of the transgenes was determined by PCR using gene specific primers for K-ras, Cre and Rosa26R-LacZ. Tissue was collected from donor animals previously treated with hormones etc. and was divided between wild-type animals that were then injected with drug or vehicle for 21 days.

From a total of four treated animals, three showed complete absence of lesion following treatment with one non-responder. In the control groups totalling 5 animals, one failed to develop a lesion.

A second study was designed to evaluate the effect of the peptide on reproduction in healthy mice and efficacy against autografted lesions derived from one uteri re-implanted in the same animal (Becker et al, AM J Pathol 178 (4): 1782-91).

Estrous Cycling 8-10 week old, female nulliparous C57BL6 mice were acclimatised for 1 week. A group of 10 animals were treated with 10 ng of peptide injected subcutaneously 3 days prior to experimentation with a group of 10 controls dosed with vehicle alone. Daily vaginal smears were taken for a period of 10 days. Normal smears were obtained in all cases Mating (Female Treatment Group)

8-10 week old, female nulliparous C57BL6 mice were acclimatised for 1 week. A group of 10 female animals were dosed with 10 ng of peptide injected subcutaneously 3 days prior to experimentation with a control group of 10 animals treated with vehicle alone.

5 male C57BL6 animals were introduced and the females checked daily for mucous plug (before 9 a.m.). When mucous plug was recorded the females were evaluated for:

a) Length of possible pregnancy (days)
b) Number of offspring
c) Anomalies in offspring All animals delivered normal litters (with the exception of one of the dosed group)

Mating (Male Treatment Group)

8-10 week old, nulliparous C57BL6 mice were acclimatised for 1 week. A group of 5 male animals were dosed with 10 ng of peptide injected subcutaneously 3 days prior to experimentation with a control group of 5 animals dosed with vehicle alone (10 ng daily SC).

10 non-treated female C57BL6 animals were introduced to each group and the females checked daily for mucous plug (before 9 a.m.). When mucous plug was recorded the females were evaluated for:

a) Length of possible pregnancy (days)
b) Number of offspring
c) Anomalies in offspring As above all animals delivered normal litters Mating (2 Generation from Treated Females)

Offspring from dosed females were mated and checked for fertility to determine possible inheritable effects. Animals were evaluated as above following plugging with no abnormalities noted.

Figure 10:
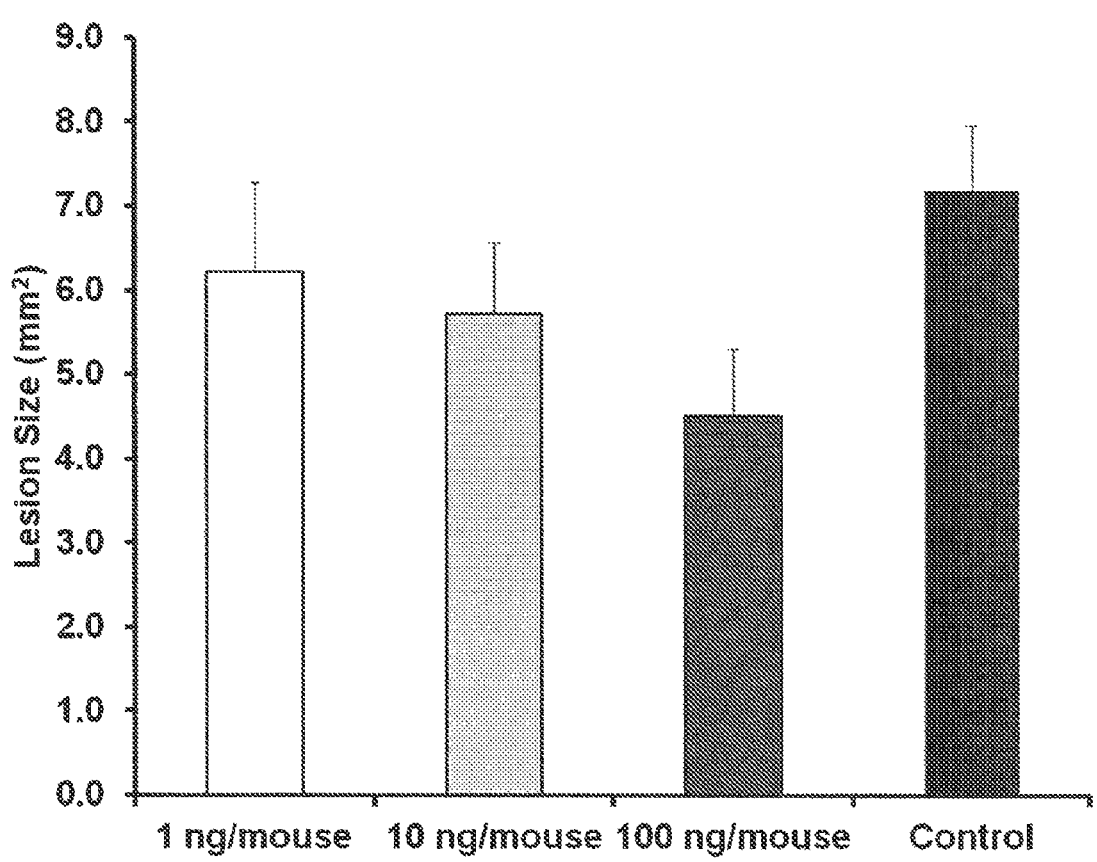
FIG. 10: Lesion growth following treatment (mm2) in dose ranging study.

Dose Ranging Prevention Study 8-10 week old, female nulliparous C57BL6 mice were each transplanted with 6× plugs of uterine tissue from donor animals after one week of acclimatisation. Three groups of 5 animals began immediate daily dosing with 1 ng, 10 ng or 100 ng of peptide injected subcutaneously with the ARP peptide and a control group of 5 animals treated with vehicle alone. Lesion growth following treatment in the dosed group was significantly reduced compared to the control group (see FIG. 10).

The model resulted in excellent lesion establishment (97.67%-100%, Table 8). A reduction in lesion burden (6.02 $mm^2$, 5.53 $mm^2$ and 4.52 $mm^2$ vs. 7.18 $mm^2$, Table 6) and growth (6.23 $mm^2$, 5.72 $mm^2$ and 4.52 vs 7.18 $mm^2$ Table 7).

With regard to dose, there is an option to synchronize estrous cycle by single injection of estrogen 2-3 days prior to surgery.

Figure 9:
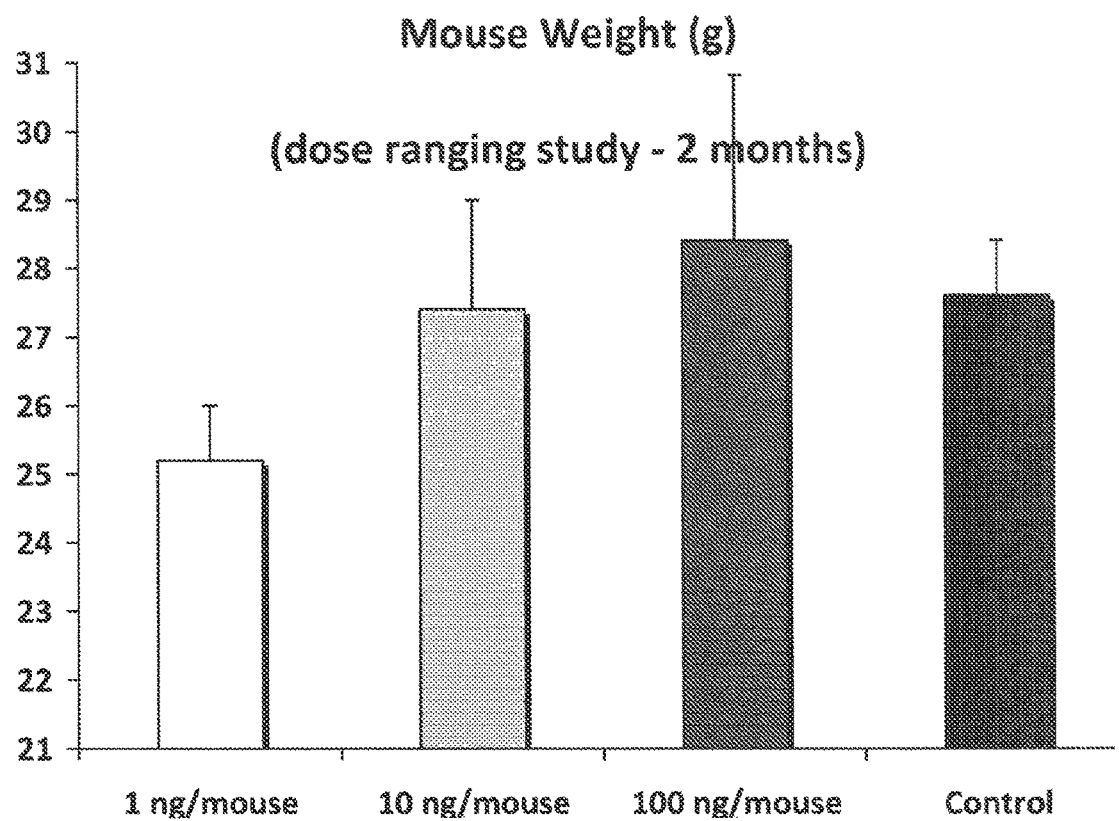
FIG. 9: Mouse weight (g) in dose ranging study.

The data obtained from the experiments described above are illustrated in FIGS. 9 and 10 and Tables 5-8.

TABLE 5

Mouse weight following treatment with Valirx1 or control without treatment

| Mouse # | Treatment | Approach | Application | Dose | Frequency | Weight | Average Weight | STD | SEM |
|---|---|---|---|---|---|---|---|---|---|
| 1 | ValiRx1 | Prevention | s.c. injection | 1 ng/mouse | Daily | 25 | | | |
| 2 | ValiRx1 | Prevention | s.c. injection | 1 ng/mouse | Daily | 27 | | | |
| 3 | ValiRx1 | Prevention | s.c. injection | 1 ng/mouse | Daily | 23 | | | |
| 4 | ValiRx1 | Prevention | s.c. injection | 1 ng/mouse | Daily | 27 | | | |
| 5 | ValiRx1 | Prevention | s.c. injection | 1 ng/mouse | Daily | 24 | 25.2 | 1.79 | 0.8 |
| 1 | ValiRx1 | Prevention | s.c. injection | 10 ng/mouse | Daily | 30 | | | |
| 2 | ValiRx1 | Prevention | s.c. injection | 10 ng/mouse | Daily | 30 | | | |
| 3 | ValiRx1 | Prevention | s.c. injection | 10 ng/mouse | Daily | 23 | | | |
| 4 | ValiRx1 | Prevention | s.c. injection | 10 ng/mouse | Daily | 30 | | | |
| 5 | ValiRx1 | Prevention | s.c. injection | 10 ng/mouse | Daily | 24 | 27.4 | 3.58 | 1.6 |
| 1 | ValiRx1 | Prevention | s.c. injection | 100 ng/mouse | Daily | 25 | | | |
| 2 | ValiRx1 | Prevention | s.c. injection | 100 ng/mouse | Daily | 27 | | | |
| 3 | ValiRx1 | Prevention | s.c. injection | 100 ng/mouse | Daily | 22 | | | |
| 4 | ValiRx1 | Prevention | s.c. injection | 100 ng/mouse | Daily | 34 | | | |
| 5 | ValiRx1 | Prevention | s.c. injection | 100 ng/mouse | Daily | 34 | 28.4 | 5.41 | 2.4207 |
| 1 | Control | Prevention | s.c. injection | n/a | Daily | 28 | | | |
| 2 | Control | Prevention | s.c. injection | n/a | Daily | 27 | | | |
| 3 | Control | Prevention | s.c. injection | n/a | Daily | 30 | | | |
| 4 | Control | Prevention | s.c. injection | n/a | Daily | 25 | | | |
| 5 | Control | Prevention | s.c. injection | n/a | Daily | 28 | 27.6 | 1.82 | 0.8124 |

TABLE 6

Lesion Burden following treatment with various doses of Valirx1 or control without treatment

| | | BURDEN | | | | | P1 | P2 | P3 |
|---|---|---|---|---|---|---|---|---|---|
| 1 | ValiRx1 | Prevention | s.c. injection | 1 ng/mouse | Daily | | 15.1 | 5.7 | 8.0 |
| 2 | ValiRx1 | Prevention | s.c. injection | 1 ng/mouse | Daily | | 10.2 | 10.6 | 16.6 |
| 3 | ValiRx1 | Prevention | s.c. injection | 1 ng/mouse | Daily | | 1.8 | 0.2 | 0.1 |
| 4 | ValiRx1 | Prevention | s.c. injection | 1 ng/mouse | Daily | | 1.1 | 3.1 | 2.5 |
| 5 | ValiRx1 | Prevention | s.c. injection | 1 ng/mouse | Daily | | 4.2 | 16.7 | 15.2 |
| 1 | ValiRx1 | Prevention | s.c. injection | 10 ng/mouse | Daily | | 1.0 | 3.5 | 10.9 |
| 2 | ValiRx1 | Prevention | s.c. injection | 10 ng/mouse | Daily | | 7.3 | 10.0 | 4.5 |
| 3 | ValiRx1 | Prevention | s.c. injection | 10 ng/mouse | Daily | | 12.6 | 7.0 | 9.6 |
| 4 | ValiRx1 | Prevention | s.c. injection | 10 ng/mouse | Daily | | 3.1 | 3.5 | 3.5 |
| 5 | ValiRx1 | Prevention | s.c. injection | 10 ng/mouse | Daily | | 1.1 | 2.5 | 3.5 |
| 1 | ValiRx1 | Prevention | s.c. injection | 100 ng/mouse | Daily | | 7.0 | 18.5 | 11.0 |
| 2 | ValiRx1 | Prevention | s.c. injection | 100 ng/mouse | Daily | | 4.5 | 2.8 | 2.3 |
| 3 | ValiRx1 | Prevention | s.c. injection | 100 ng/mouse | Daily | | 2.8 | 2.3 | 2.3 |
| 4 | ValiRx1 | Prevention | s.c. injection | 100 ng/mouse | Daily | | 2.0 | 3.1 | 3.5 |
| 5 | ValiRx1 | Prevention | s.c. injection | 100 ng/mouse | Daily | | 1.5 | 3.5 | 4.9 |
| 1 | Control | Prevention | s.c. injection | n/a | Daily | | 0.2 | 4.9 | 6.6 |
| 2 | Control | Prevention | s.c. injection | n/a | Daily | | 7.5 | 6.6 | 9.1 |
| 3 | Control | Prevention | s.c. injection | n/a | Daily | | 2.5 | 3.8 | 3.8 |
| 4 | Control | Prevention | s.c. injection | n/a | Daily | | 4.2 | 4.9 | 5.3 |
| 5 | Control | Prevention | s.c. injection | n/a | Daily | | 7.0 | 15.7 | 16.7 |

| | P4 | P5 | P6 | Ave | Mean | StDev | SEM | Ttest |
|---|---|---|---|---|---|---|---|---|
| 1 | 3.8 | 0.2 | 6.2 | 6.5 | | | | |
| 2 | 3.8 | 0.5 | 9.4 | 8.5 | | | | |
| 3 | 0.0 | 3.5 | 1.1 | 1.1 | | | | |
| 4 | 0.2 | 1.1 | 3.5 | 1.9 | | | | |
| 5 | 17.0 | 11.2 | 8.0 | 12.1 | 6.02 | 5.69 | 1.04 | |
| 1 | 1.0 | 1.0 | 0.2 | 2.9 | | | | |
| 2 | 6.7 | 7.1 | 4.5 | 6.7 | | | | |
| 3 | 5.4 | 21.1 | 12.1 | 11.3 | | | | |
| 4 | 3.0 | 3.5 | 3.1 | 3.3 | | | | |
| 5 | 0.0 | 4.0 | 9.7 | 3.5 | 5.53 | 4.63 | 0.85 | |
| 1 | 8.4 | 12.6 | 13.2 | 11.8 | | | | |
| 2 | 0.2 | 1.0 | 0.3 | 1.8 | | | | |

TABLE 6-continued

Lesion Burden following treatment with various doses of Valirx1 or control without treatment

| | | | | | | | | | | |
|---|---|---|---|---|---|---|---|---|---|---|
| 3 | 3.8 | 7.5 | 0.3 | 3.2 | | | | | | |
| 4 | 2.5 | 3.8 | 2.8 | 3.0 | | | | | | |
| 5 | 1.8 | 2.0 | 3.5 | 2.9 | 4.52 | 4.31 | 0.79 | | | |
| 1 | 9.3 | 9.6 | 10.2 | 6.8 | | | | | | |
| 2 | 7.1 | 9.8 | 7.5 | 7.9 | | | | | | |
| 3 | 7.0 | 6.2 | 1.8 | 4.2 | | | | | | |
| 4 | 9.6 | 8.5 | 4.9 | 6.2 | | | | | | |
| 5 | 0.5 | 18.4 | 6.2 | 10.8 | 7.18 | 4.26 | 0.78 | 0.37 | 0.15 | 0.01908652 |

TABLE 7

Lesion Growth following treatment with various doses of Valirx1 or control without treatment

| | | Growth | | | | | P1 | P2 | P3 |
|---|---|---|---|---|---|---|---|---|---|
| 1 | ValiRx1 | Prevention | s.c. injection | 1 | ng/mouse | Daily | 15.1 | 5.694 | 8.042 |
| 2 | ValiRx1 | Prevention | s.c. injection | 1 | ng/mouse | Daily | 10.18 | 10.56 | 16.62 |
| 3 | ValiRx1 | Prevention | s.c. injection | 1 | ng/mouse | Daily | 1.767 | 0.196 | 0.126 |
| 4 | ValiRx1 | Prevention | s.c. injection | 1 | ng/mouse | Daily | 1.131 | 3.142 | 2.545 |
| 5 | ValiRx1 | Prevention | s.c. injection | 1 | ng/mouse | Daily | 4.155 | 16.74 | 15.21 |
| 1 | ValiRx1 | Prevention | s.c. injection | 10 | ng/mouse | Daily | 0.95 | 3.464 | 10.95 |
| 2 | ValiRx1 | Prevention | s.c. injection | 10 | ng/mouse | Daily | 7.288 | 10.02 | 4.524 |
| 3 | ValiRx1 | Prevention | s.c. injection | 10 | ng/mouse | Daily | 12.57 | 7.037 | 9.621 |
| 4 | ValiRx1 | Prevention | s.c. injection | 10 | ng/mouse | Daily | 3.142 | 3.464 | 3.464 |
| 5 | ValiRx1 | Prevention | s.c. injection | 10 | ng/mouse | Daily | 1.131 | 2.545 | 3.464 |
| 1 | ValiRx1 | Prevention | s.c. injection | 100 | ng/mouse | Daily | 7.037 | 18.47 | 11 |
| 2 | ValiRx1 | Prevention | s.c. injection | 100 | ng/mouse | Daily | 4.453 | 2.827 | 2.27 |
| 3 | ValiRx1 | Prevention | s.c. injection | 100 | ng/mouse | Daily | 2.827 | 2.27 | 2.27 |
| 4 | ValiRx1 | Prevention | s.c. injection | 100 | ng/mouse | Daily | 2.011 | 3.142 | 3.464 |
| 5 | ValiRx1 | Prevention | s.c. injection | 100 | ng/mouse | Daily | 1.539 | 3.464 | 4.909 |
| 1 | Control | Prevention | s.c. injection | n/a | | Daily | 0.196 | 4.909 | 6.605 |
| 2 | Control | Prevention | s.c. injection | n/a | | Daily | 7.548 | 6.605 | 9.079 |
| 3 | Control | Prevention | s.c. injection | n/a | | Daily | 2.545 | 3.801 | 3.801 |
| 4 | Control | Prevention | s.c. injection | n/a | | Daily | 4.155 | 4.909 | 5.309 |
| 5 | Control | Prevention | s.c. injection | n/a | | Daily | 7.037 | 15.71 | 16.74 |

| | P4 | M1 | M2 | Ave | Mean | StDev | SEM | Ttest |
|---|---|---|---|---|---|---|---|---|
| 1 | 3.801 | 0.196 | 6.158 | 6.5 | | | | |
| 2 | 3.801 | 0.503 | 9.425 | 8.5 | | | | |
| 3 | | 3.456 | 1.131 | 1.3 | | | | |
| 4 | 0.196 | 1.131 | 3.464 | 1.9 | | | | |
| 5 | 16.96 | 11.2 | 8.042 | 12.1 | 6.23 | 5.67 | 1.05 | |
| 1 | 0.95 | 0.95 | 0.196 | 2.9 | | | | |
| 2 | 6.739 | 7.069 | 4.524 | 6.7 | | | | |
| 3 | 5.372 | 21.11 | 12.06 | 11.3 | | | | |
| 4 | 2.969 | 3.464 | 3.142 | 3.3 | | | | |
| 5 | | 3.958 | 9.66 | 4.2 | 5.72 | 4.59 | 0.85 | |
| 1 | 8.357 | 12.57 | 13.2 | 11.8 | | | | |
| 2 | 0.196 | 0.95 | 0.283 | 1.8 | | | | |
| 3 | 3.801 | 7.548 | 0.283 | 3.2 | | | | |
| 4 | 2.545 | 3.801 | 2.835 | 3.0 | | | | |
| 5 | 1.767 | 2.011 | 3.464 | 2.9 | 4.52 | 4.31 | 0.79 | |
| 1 | 9.346 | 9.621 | 10.18 | 6.8 | | | | |
| 2 | 7.061 | 9.802 | 7.548 | 7.9 | | | | |
| 3 | 7.037 | 6.158 | 1.767 | 4.2 | | | | |
| 4 | 9.55 | 8.545 | 4.909 | 6.2 | | | | |
| 5 | 0.503 | 18.38 | 6.158 | 10.8 | 7.18 | 4.26 | 0.78 | 0.47 | 0.019086519 |

TABLE 8

Lesion establishment

| | ESTABLISHMENT | | | | | P1 | P2 | P3 | P4 | M1 | M2 | Ave | Mean | StDev | SEM | Ttest |
|---|---|---|---|---|---|---|---|---|---|---|---|---|---|---|---|---|
| 1 | ValiRx1 | Prevention | s.c. injection | 1 ng/mouse | Daily | 1 | 1 | 1 | 1 | 1 | 1 | 100 | | | | |
| 2 | ValiRx1 | Prevention | s.c. injection | 1 ng/mouse | Daily | 1 | 1 | 1 | 1 | 1 | 1 | 100 | | | | |
| 3 | ValiRx1 | Prevention | s.c. injection | 1 ng/mouse | Daily | 1 | 1 | 1 | 0 | 1 | 1 | 83.33 | | | | |
| 4 | ValiRx1 | Prevention | s.c. injection | 1 ng/mouse | Daily | 1 | 1 | 1 | 1 | 1 | 1 | 100 | | | | |
| 5 | ValiRx1 | Prevention | s.c. injection | 1 ng/mouse | Daily | 1 | 1 | 1 | 1 | 1 | 1 | 100 | 96.67 | 7.45 | 1.36 | |
| 1 | ValiRx1 | Prevention | s.c. injection | 10 ng/mouse | Daily | 1 | 1 | 1 | 1 | 1 | 1 | 100 | | | | |
| 2 | ValiRx1 | Prevention | s.c. injection | 10 ng/mouse | Daily | 1 | 1 | 1 | 1 | 1 | 1 | 100 | | | | |
| 3 | ValiRx1 | Prevention | s.c. injection | 10 ng/mouse | Daily | 1 | 1 | 1 | 1 | 1 | 1 | 100 | | | | |
| 4 | ValiRx1 | Prevention | s.c. injection | 10 ng/mouse | Daily | 1 | 1 | 1 | 1 | 1 | 1 | 100 | | | | |
| 5 | ValiRx1 | Prevention | s.c. injection | 10 ng/mouse | Daily | 1 | 1 | 1 | 0 | 1 | 1 | 83.33 | 96.67 | 7.45 | 1.36 | |
| 1 | ValiRx1 | Prevention | s.c. injection | 100 ng/mouse | Daily | 1 | 1 | 1 | 1 | 1 | 1 | 100 | | | | |
| 2 | ValiRx1 | Prevention | s.c. injection | 100 ng/mouse | Daily | 1 | 1 | 1 | 1 | 1 | 1 | 100 | | | | |
| 3 | ValiRx1 | Prevention | s.c. injection | 100 ng/mouse | Daily | 1 | 1 | 1 | 1 | 1 | 1 | 100 | | | | |
| 4 | ValiRx1 | Prevention | s.c. injection | 100 ng/mouse | Daily | 1 | 1 | 1 | 1 | 1 | 1 | 100 | | | | |
| 5 | ValiRx1 | Prevention | s.c. injection | 100 ng/mouse | Daily | 1 | 1 | 1 | 1 | 1 | 1 | 100 | 100.00 | 0.00 | 0.00 | |
| 1 | Control | Prevention | s.c. injection | n/a | Daily | 1 | 1 | 1 | 1 | 1 | 1 | 100 | | | | |
| 2 | Control | Prevention | s.c. injection | n/a | Daily | 1 | 1 | 1 | 1 | 1 | 1 | 100 | | | | |
| 3 | Control | Prevention | s.c. injection | n/a | Daily | 1 | 1 | 1 | 1 | 1 | 1 | 100 | | | | |
| 4 | Control | Prevention | s.c. injection | n/a | Daily | 1 | 1 | 1 | 1 | 1 | 1 | 100 | | | | |
| 5 | Control | Prevention | s.c. injection | n/a | Daily | 1 | 1 | 1 | 1 | 1 | 1 | 100 | 100.00 | 0.00 | 0.00 | |

EXAMPLE 4: INHIBITING ANDROGEN RECEPTOR-ASSOCIATED SRC SIGNALLING BY VAL201 INHIBITS PROSTATE CANCER METASTASIS IN AN ORTHOTOPIC MOUSE MODEL

VAL201 (Ac-PPPHPHARIK-NH2 (SEQ ID. NO.: 22) where Ac is an acetyl group) is a specific inhibitor of androgen receptor (AR) and estrogen receptor (ER) associated src signalling. Inhibition of src by VAL201 takes place after androgen binding, allowing inhibition of growth without blocking desirable receptor-dependent transcriptional activity, and thereby eliminating the majority of side effects associated with androgen deprivation therapies. We have studied the effects of Val201 on cell proliferation of the ER positive human prostate cancer cell line PC-3 in vitro and growth and metastatis in vivo in an orthotopic xenograft model. The proliferation effects were studied for 100 pM, 1 nM, 10 nM, 100 nM and 1 µM concentrations of VAL201 by measuring WST-1 values at days 3, 5, 7 and 9. Groups with vehicle and 1 µM gemcitabine as reference compound were included in the study. The xenograft study was performed with 6-7 week-old immunodeficient BALB/c nude mice that were allocated to 6 groups (with n=15/group) according to the body weight, one group receiving vehicle and the others VAL201 at doses 0.04, 0.4, 4, 10 and 20 mg/kg. PC-3 cells in Matrigel were inoculated orthotopically into the prostate. Subcutaneous dosing was started at day 1 and continued daily for 28 days. The mice were weighed twice a week. Orthotopic tumors were measured by calliper and the prostate and the regional lymph nodes were harvested at sacrifice. Metastases in lymph nodes were determined from HE stained paraffin sections. VAL201 showed dose-dependent inhibition of PC-3 cell proliferation that was statistically significant with all doses above 100 pM. In the xenograft study VAL201 had no effect on body weight. Statistically significant effects on orthotopic tumor growth were not observed despite a 35% decrease observed in tumor volume with the 0.4 mg/kg dose. However, 0.04 and 0.4 mg/kg doses of VAL201 showed a significant 50% inhibition of the development of lymph node metastases. As a conclusion, VAL201 inhibited proliferation of PC-3 cells in vitro and development of lymph node metastases in a xenograft model, demonstrating its potential in inhibiting prostate cancer growth and metastasis without adverse effects associated with androgen deprivation.

The invention claimed is:

1. A method of preventing the symptoms of a metastatic cancer from worsening, reducing the progression of a metastatic cancer or treating a metastatic cancer in a mammalian subject who is fertile and in whom fertility is to be preserved, the method comprising administering to the subject a molecule that inhibits or prevents an interaction between a Src family kinase and an androgen receptor (AR) or estradiol receptor (ER) in an amount sufficient for preventing the symptoms of the metastatic cancer from worsening, reducing the progression of the metastatic cancer, or treating the metastatic cancer in the subject, wherein the metastatic cancer is one in which an interaction between a Src family kinase and an AR and/or ER is a contributory factor, wherein the molecule comprises a peptide having the structure: $B_j$-[(Pro)$_n$-$X_r$-His-Pro-His-Ala-Arg-Ile-Lys]$_m$-$R_p$ (SEQ ID NO. 1), or $B_j$-[lys-ile-arg-ala-his-pro-his-$x_r$-(pro)$_n$]$_m$-$R_p$ (SEQ ID NO. 2), or a derivative or fragment thereof, wherein B is a first chemical moiety, j is 0 or 1, n is an integer from 1-10, X is any amino acid, r is an integer from 0 to 2, m is an integer from 1 to 3, R is a second chemical moiety, p is 0 or 1, and [lys-ile-arg-ala-his-pro-his-$x_r$-(pro)$_n$] is the retro-inverso peptide of [(Pro)n-$X_r$-His-Pro-His-Ala-Arg-Ile-Lys] (SEQ ID NO. 1), and wherein the molecule does not reduce or prevent fertility in the subject.

2. The method of claim 1, wherein the subject is a human being.

3. The method of claim 2, wherein the molecule is one that binds to the SH3 domain of a Src family kinase.

4. The method of claim 3, wherein the Src family kinase is any of Src, Yes, Fyn, Fgr, Lck, Hck, Blk, Lyn and Frk.

5. The method of claim 1, wherein the peptide has the structure Ac-Pro-Pro-Pro-His-Pro-H is-Ala-Arg-Ile-Lys-NH$_2$ (SEQ ID NO. 21), where Ac is an acetyl group.

6. The method of claim 5, wherein the metastatic cancer is selected from the group consisting of metastatic fibrosarcoma; metastatic prostate cancer; metastatic breast cancer; metastatic uterine fibroids; metastatic fibroids polyps hyperplasia; metastatic ovarian cancer; metastatic bladder cancer; metastatic cervical cancer; metastatic uterine cancer; metastatic testicular cancer; metastatic lung cancer; metastatic intestinal cancer; metastatic liver cancer; metastatic kidney cancer; and metastatic oesophageal cancer.

7. The method of claim 5, wherein the metastatic cancer is prostate cancer.

8. A method of preventing the symptoms of metastatic prostate cancer from worsening, reducing the progression of metastatic prostate cancer or treating metastatic prostate cancer in a human being who is fertile and in whom fertility is to be preserved, comprising administering to the human being a peptide having the structure Ac-Pro-Pro-Pro-His-Pro-His-Ala-Arg-Ile-Lys-NH$_2$ (SEQ ID NO. 21) wherein Ac is an acetyl group in an amount effective for preventing the symptoms of the metastatic prostate cancer from worsening, reducing the progression of the metastatic prostate cancer, or treating the metastatic prostate cancer,
    wherein the metastatic prostate cancer is one in which an interaction between a Src family kinase and an AR and/or ER is a contributory factor, and
    wherein the peptide does not reduce or prevent fertility in the human being.

* * * * *

```
                        SEQUENCE LISTING

<160> NUMBER OF SEQ ID NOS: 70

<210> SEQ ID NO 1
<211> LENGTH: 9
<212> TYPE: PRT
<213> ORGANISM: Artificial Sequence
<220> FEATURE:
<223> OTHER INFORMATION: Preferred embodiment
<220> FEATURE:
<221> NAME/KEY: REPEAT
<222> LOCATION: 1
<223> OTHER INFORMATION: Wherein this feature may be between 1 and 10.
<220> FEATURE:
<221> NAME/KEY: VARIANT
<222> LOCATION: 2
<223> OTHER INFORMATION: Wherein this feature could be any naturally
      occurring amino acid.
<220> FEATURE:
<221> NAME/KEY: REPEAT
```

```
<222> LOCATION: 2
<223> OTHER INFORMATION: Wherein this feature may be between 0 and 2.
<220> FEATURE:
<221> NAME/KEY: REPEAT
<222> LOCATION: 1 - 9
<223> OTHER INFORMATION: Wherein this feature may be between 1 and 3.

<400> SEQUENCE: 1

Pro Xaa His Pro His Ala Arg Ile Lys
1               5

<210> SEQ ID NO 2
<211> LENGTH: 9
<212> TYPE: PRT
<213> ORGANISM: Artificial Sequence
<220> FEATURE:
<223> OTHER INFORMATION: Preferred embodiment - retero inverso
<220> FEATURE:
<221> NAME/KEY: VARIANT
<222> LOCATION: 8
<223> OTHER INFORMATION: Wherein this feature could be any naturally
      occurring amino acid.
<220> FEATURE:
<221> NAME/KEY: REPEAT
<222> LOCATION: 8
<223> OTHER INFORMATION: Wherein this feature may be between 0 and 2.
<220> FEATURE:
<221> NAME/KEY: REPEAT
<222> LOCATION: 9
<223> OTHER INFORMATION: Wherein this feature may be between 1 and 10.
<220> FEATURE:
<221> NAME/KEY: REPEAT
<222> LOCATION: 1 - 9
<223> OTHER INFORMATION: Wherein this feature may be between 1 and 3.
<220> FEATURE:
<221> NAME/KEY: MISC_FEATURE
<222> LOCATION: 1 - 9
<223> OTHER INFORMATION: Wherein these amino acids are D-amino acids.

<400> SEQUENCE: 2

Lys Ile Arg Ala His Pro His Xaa Pro
1               5

<210> SEQ ID NO 3
<211> LENGTH: 7
<212> TYPE: PRT
<213> ORGANISM: Artificial Sequence
<220> FEATURE:
<223> OTHER INFORMATION: Example of suitable fragment

<400> SEQUENCE: 3

His Pro His Ala Arg Ile Lys
1               5

<210> SEQ ID NO 4
<211> LENGTH: 5
<212> TYPE: PRT
<213> ORGANISM: Artificial Sequence
<220> FEATURE:
<223> OTHER INFORMATION: Example of suitable fragment

<400> SEQUENCE: 4

His Pro His Ala Arg
1               5

<210> SEQ ID NO 5
<211> LENGTH: 6
<212> TYPE: PRT
<213> ORGANISM: Artificial Sequence
<220> FEATURE:
<223> OTHER INFORMATION: Example of suitable fragment
```

```
<400> SEQUENCE: 5

Pro His Pro His Ala Arg
1               5

<210> SEQ ID NO 6
<211> LENGTH: 4
<212> TYPE: PRT
<213> ORGANISM: Artificial Sequence
<220> FEATURE:
<223> OTHER INFORMATION: Example of suitable fragment

<400> SEQUENCE: 6

Pro His Pro His
1

<210> SEQ ID NO 7
<211> LENGTH: 5
<212> TYPE: PRT
<213> ORGANISM: Artificial Sequence
<220> FEATURE:
<223> OTHER INFORMATION: Example of suitable fragment

<400> SEQUENCE: 7

Pro Pro His Pro His
1               5

<210> SEQ ID NO 8
<211> LENGTH: 6
<212> TYPE: PRT
<213> ORGANISM: Artificial Sequence
<220> FEATURE:
<223> OTHER INFORMATION: Example of suitable fragment

<400> SEQUENCE: 8

Pro Pro Pro His Pro His
1               5

<210> SEQ ID NO 9
<211> LENGTH: 4
<212> TYPE: PRT
<213> ORGANISM: Artificial Sequence
<220> FEATURE:
<223> OTHER INFORMATION: Example of suitable fragment

<400> SEQUENCE: 9

Pro Pro His Pro
1

<210> SEQ ID NO 10
<211> LENGTH: 5
<212> TYPE: PRT
<213> ORGANISM: Artificial Sequence
<220> FEATURE:
<223> OTHER INFORMATION: Example of suitable fragment

<400> SEQUENCE: 10

Pro Pro Pro His Pro
1               5

<210> SEQ ID NO 11
<211> LENGTH: 4
<212> TYPE: PRT
<213> ORGANISM: Artificial Sequence
<220> FEATURE:
<223> OTHER INFORMATION: Example of suitable fragment
```

```
<400> SEQUENCE: 11

Pro Pro Pro His
1

<210> SEQ ID NO 12
<211> LENGTH: 7
<212> TYPE: PRT
<213> ORGANISM: Artificial Sequence
<220> FEATURE:
<223> OTHER INFORMATION: Acetylated example of suitable fragment

<400> SEQUENCE: 12

His Pro His Ala Arg Ile Lys
1               5

<210> SEQ ID NO 13
<211> LENGTH: 5
<212> TYPE: PRT
<213> ORGANISM: Artificial Sequence
<220> FEATURE:
<223> OTHER INFORMATION: Acetylated example of suitable fragment

<400> SEQUENCE: 13

His Pro His Ala Arg
1               5

<210> SEQ ID NO 14
<211> LENGTH: 6
<212> TYPE: PRT
<213> ORGANISM: Artificial Sequence
<220> FEATURE:
<223> OTHER INFORMATION: Acetylated example of suitable fragment

<400> SEQUENCE: 14

Pro His Pro His Ala Arg
1               5

<210> SEQ ID NO 15
<211> LENGTH: 4
<212> TYPE: PRT
<213> ORGANISM: Artificial Sequence
<220> FEATURE:
<223> OTHER INFORMATION: Acetylated example of suitable fragment

<400> SEQUENCE: 15

Pro His Pro His
1

<210> SEQ ID NO 16
<211> LENGTH: 5
<212> TYPE: PRT
<213> ORGANISM: Artificial Sequence
<220> FEATURE:
<223> OTHER INFORMATION: Acetylated example of suitable fragment

<400> SEQUENCE: 16

Pro Pro His Pro His
1               5

<210> SEQ ID NO 17
<211> LENGTH: 6
<212> TYPE: PRT
<213> ORGANISM: Artificial Sequence
<220> FEATURE:
<223> OTHER INFORMATION: Acetylated example of suitable fragment

<400> SEQUENCE: 17
```

```
Pro Pro Pro His Pro His
1               5

<210> SEQ ID NO 18
<211> LENGTH: 4
<212> TYPE: PRT
<213> ORGANISM: Artificial Sequence
<220> FEATURE:
<223> OTHER INFORMATION: Acetylated example of suitable fragment

<400> SEQUENCE: 18

Pro Pro His Pro
1

<210> SEQ ID NO 19
<211> LENGTH: 5
<212> TYPE: PRT
<213> ORGANISM: Artificial Sequence
<220> FEATURE:
<223> OTHER INFORMATION: Acetylated example of suitable fragment

<400> SEQUENCE: 19

Pro Pro Pro His Pro
1               5

<210> SEQ ID NO 20
<211> LENGTH: 4
<212> TYPE: PRT
<213> ORGANISM: Artificial Sequence
<220> FEATURE:
<223> OTHER INFORMATION: Acetylated example of suitable fragment

<400> SEQUENCE: 20

Pro Pro Pro His
1

<210> SEQ ID NO 21
<211> LENGTH: 10
<212> TYPE: PRT
<213> ORGANISM: Homo sapiens

<400> SEQUENCE: 21

Pro Pro Pro His Pro His Ala Arg Ile Lys
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Retero-inverso peptide of Homo sapiens AR.
<220> FEATURE:
<221> NAME/KEY: MISC_FEATURE
<222> LOCATION: 1 - 10
<223> OTHER INFORMATION: Wherein these amino acids are D-amino acids.

<400> SEQUENCE: 22

Lys Ile Arg Ala His Pro His Pro Pro Pro
1               5                   10

<210> SEQ ID NO 23
<211> LENGTH: 10
<212> TYPE: PRT
<213> ORGANISM: Mus musculus

<400> SEQUENCE: 23
```

Pro Pro Thr His Pro His Ala Arg Ile Lys
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Retero-inverso peptide of Mus musculus AR.
<220> FEATURE:
<221> NAME/KEY: MISC_FEATURE
<222> LOCATION: 1 - 10
<223> OTHER INFORMATION: Wherein these amino acids are D-amino acids.

<400> SEQUENCE: 24

Lys Ile Arg Ala His Pro His Thr Pro Pro
1               5                   10

<210> SEQ ID NO 25
<211> LENGTH: 10
<212> TYPE: PRT
<213> ORGANISM: Rattus rattus

<400> SEQUENCE: 25

Pro Pro Thr His Pro His Ala Arg Ile Lys
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Retero-inverso peptide of Rattus rattus AR.
<220> FEATURE:
<221> NAME/KEY: MISC_FEATURE
<222> LOCATION: 1 - 10
<223> OTHER INFORMATION: Wherein these amino acids are D-amino acids.

<400> SEQUENCE: 26

Lys Ile Arg Ala His Pro His Thr Pro Pro
1               5                   10

<210> SEQ ID NO 27
<211> LENGTH: 10
<212> TYPE: PRT
<213> ORGANISM: Sus scrofa

<400> SEQUENCE: 27

Pro Pro Pro His Pro His Ala Arg Ile Lys
1               5                   10

<210> SEQ ID NO 28
<211> LENGTH: 10
<212> TYPE: PRT
<213> ORGANISM: Papio hamadryas

<400> SEQUENCE: 28

Pro Pro Pro His Pro His Ala Arg Ile Lys
1               5                   10

<210> SEQ ID NO 29
<211> LENGTH: 10
<212> TYPE: PRT
<213> ORGANISM: Pan troglodytes

<400> SEQUENCE: 29

Pro Pro Pro His Pro His Ala Arg Ile Lys 1               5                   10

<210> SEQ ID NO 30
<211> LENGTH: 10
<212> TYPE: PRT
<213> ORGANISM: Macaca mulatta

<400> SEQUENCE: 30

Pro Pro Pro His Pro His Ala Arg Ile Lys
1               5                   10

<210> SEQ ID NO 31
<211> LENGTH: 10
<212> TYPE: PRT
<213> ORGANISM: Cynomolgus monkey

<400> SEQUENCE: 31

Pro Pro Pro His Pro His Ala Arg Ile Lys
1               5                   10

<210> SEQ ID NO 32
<211> LENGTH: 10
<212> TYPE: PRT
<213> ORGANISM: Red squirrel

<400> SEQUENCE: 32

Pro Pro Pro His Pro His Ala Arg Ile Lys
1               5                   10

<210> SEQ ID NO 33
<211> LENGTH: 10
<212> TYPE: PRT
<213> ORGANISM: Felis catus

<400> SEQUENCE: 33

Pro Pro Pro His Pro His Ala Arg Ile Lys
1               5                   10

<210> SEQ ID NO 34
<211> LENGTH: 10
<212> TYPE: PRT
<213> ORGANISM: Galidia elegans

<400> SEQUENCE: 34

Pro Pro Pro His Pro His Ala Arg Ile Lys
1               5                   10

<210> SEQ ID NO 35
<211> LENGTH: 10
<212> TYPE: PRT
<213> ORGANISM: Eupleres goudotii

<400> SEQUENCE: 35

Pro Pro Pro His Pro His Ala Arg Ile Lys
1               5                   10

<210> SEQ ID NO 36
<211> LENGTH: 10
<212> TYPE: PRT
<213> ORGANISM: Fossa fossana

<400> SEQUENCE: 36

Pro Pro Pro His Pro His Ala Arg Ile Lys
1               5                   10

```
<210> SEQ ID NO 37
<211> LENGTH: 10
<212> TYPE: PRT
<213> ORGANISM: Viverricula indica

<400> SEQUENCE: 37

Pro Pro Pro His Pro His Ala Arg Ile Lys
1               5                   10

<210> SEQ ID NO 38
<211> LENGTH: 10
<212> TYPE: PRT
<213> ORGANISM: Diceros bicornis

<400> SEQUENCE: 38

Pro Pro Pro His Pro His Ala Arg Ile Lys
1               5                   10

<210> SEQ ID NO 39
<211> LENGTH: 10
<212> TYPE: PRT
<213> ORGANISM: Equus caballus

<400> SEQUENCE: 39

Pro Pro Pro His Pro His Ala Arg Ile Lys
1               5                   10

<210> SEQ ID NO 40
<211> LENGTH: 10
<212> TYPE: PRT
<213> ORGANISM: Lama guanicoe pacos

<400> SEQUENCE: 40

Pro Pro Pro His Pro His Ala Arg Ile Lys
1               5                   10

<210> SEQ ID NO 41
<211> LENGTH: 10
<212> TYPE: PRT
<213> ORGANISM: Physeter catodon

<400> SEQUENCE: 41

Pro Pro Pro His Pro His Ala Arg Ile Lys
1               5                   10

<210> SEQ ID NO 42
<211> LENGTH: 10
<212> TYPE: PRT
<213> ORGANISM: Trichechus manatus

<400> SEQUENCE: 42

Pro Pro Pro His Pro His Ala Arg Ile Lys
1               5                   10

<210> SEQ ID NO 43
<211> LENGTH: 10
<212> TYPE: PRT
<213> ORGANISM: Elephas maximus

<400> SEQUENCE: 43

Pro Pro Pro His Pro His Ala Arg Ile Lys
1               5                   10

<210> SEQ ID NO 44
```

```
<211> LENGTH: 10
<212> TYPE: PRT
<213> ORGANISM: Oryctolagus cuniculus

<400> SEQUENCE: 44

Pro Pro Pro His Pro His Ala Arg Ile Lys
1               5                   10

<210> SEQ ID NO 45
<211> LENGTH: 10
<212> TYPE: PRT
<213> ORGANISM: Lepus crawshayi

<400> SEQUENCE: 45

Pro Pro Pro His Pro His Ala Arg Ile Lys
1               5                   10

<210> SEQ ID NO 46
<211> LENGTH: 10
<212> TYPE: PRT
<213> ORGANISM: Tarsius bancanus

<400> SEQUENCE: 46

Pro Pro Pro His Pro His Ala Arg Ile Lys
1               5                   10

<210> SEQ ID NO 47
<211> LENGTH: 10
<212> TYPE: PRT
<213> ORGANISM: Cynopterus sphinx

<400> SEQUENCE: 47

Pro Pro Pro His Pro His Ala Arg Ile Lys
1               5                   10

<210> SEQ ID NO 48
<211> LENGTH: 10
<212> TYPE: PRT
<213> ORGANISM: Tupaia tana

<400> SEQUENCE: 48

Pro Pro Pro His Pro His Ala Arg Ile Lys
1               5                   10

<210> SEQ ID NO 49
<211> LENGTH: 10
<212> TYPE: PRT
<213> ORGANISM: Saimiri boliviensis

<400> SEQUENCE: 49

Pro Pro Pro His Pro His Ala Arg Ile Lys
1               5                   10

<210> SEQ ID NO 50
<211> LENGTH: 6
<212> TYPE: PRT
<213> ORGANISM: Canis familiaris

<400> SEQUENCE: 50

Pro Pro Pro His Pro His
1               5

<210> SEQ ID NO 51
<211> LENGTH: 9
<212> TYPE: PRT
```

<213> ORGANISM: Eulemur fulvus collaris

<400> SEQUENCE: 51

Pro Pro His Pro His Ala Arg Ile Lys
1               5

<210> SEQ ID NO 52
<211> LENGTH: 9
<212> TYPE: PRT
<213> ORGANISM: Lemur catta

<400> SEQUENCE: 52

Pro Pro His Pro His Ala Arg Ile Lys
1               5

<210> SEQ ID NO 53
<211> LENGTH: 9
<212> TYPE: PRT
<213> ORGANISM: Eulemur fulvus fulvus

<400> SEQUENCE: 53

Pro Pro His Pro His Ala Arg Ile Lys
1               5

<210> SEQ ID NO 54
<211> LENGTH: 9
<212> TYPE: PRT
<213> ORGANISM: Hapalemur simus

<400> SEQUENCE: 54

Pro Pro His Pro His Ala Arg Ile Lys
1               5

<210> SEQ ID NO 55
<211> LENGTH: 9
<212> TYPE: PRT
<213> ORGANISM: Lepilemur edwardsi

<400> SEQUENCE: 55

Pro Pro His Pro His Ala Arg Ile Lys
1               5

<210> SEQ ID NO 56
<211> LENGTH: 9
<212> TYPE: PRT
<213> ORGANISM: Cheirogaleus medius

<400> SEQUENCE: 56

Pro Pro His Pro His Ala Arg Ile Lys
1               5

<210> SEQ ID NO 57
<211> LENGTH: 9
<212> TYPE: PRT
<213> ORGANISM: Daubentonia madagascariensis

<400> SEQUENCE: 57

Pro Pro His Pro His Ala Arg Ile Lys
1               5

<210> SEQ ID NO 58
<211> LENGTH: 9
<212> TYPE: PRT
<213> ORGANISM: Propithecus deckenii coronatus

```
<400> SEQUENCE: 58

Pro Pro His Pro His Ala Arg Ile Lys
1               5

<210> SEQ ID NO 59
<211> LENGTH: 9
<212> TYPE: PRT
<213> ORGANISM: Nycticebus coucang

<400> SEQUENCE: 59

Pro Pro His Pro His Ala Arg Ile Lys
1               5

<210> SEQ ID NO 60
<211> LENGTH: 10
<212> TYPE: PRT
<213> ORGANISM: Cavia porcellus

<400> SEQUENCE: 60

Pro Pro Pro His Pro Asn Ala Arg Ile Lys
1               5                   10

<210> SEQ ID NO 61
<211> LENGTH: 11
<212> TYPE: PRT
<213> ORGANISM: Rattus norvegicus

<400> SEQUENCE: 61

Pro Pro Pro Thr His Pro His Ala Arg Ile Lys
1               5                   10

<210> SEQ ID NO 62
<211> LENGTH: 11
<212> TYPE: PRT
<213> ORGANISM: Mus musculus

<400> SEQUENCE: 62

Pro Pro Pro Thr His Pro His Ala Arg Ile Lys
1               5                   10

<210> SEQ ID NO 63
<211> LENGTH: 9
<212> TYPE: PRT
<213> ORGANISM: Crocuta crocuta

<400> SEQUENCE: 63

Pro Pro His Pro His Ala Arg Ile Lys
1               5

<210> SEQ ID NO 64
<211> LENGTH: 11
<212> TYPE: PRT
<213> ORGANISM: Eliurus sp

<400> SEQUENCE: 64

Pro Pro Pro Thr His Pro His Ala Arg Ile Lys
1               5                   10

<210> SEQ ID NO 65
<211> LENGTH: 11
<212> TYPE: PRT
<213> ORGANISM: Steatomys sp

<400> SEQUENCE: 65
```

```
Pro Pro Pro Thr His Pro His Ala Arg Ile Lys
1               5                   10

<210> SEQ ID NO 66
<211> LENGTH: 11
<212> TYPE: PRT
<213> ORGANISM: Otomys angoniensis

<400> SEQUENCE: 66

Pro Pro Pro Thr His Pro His Ala Arg Ile Lys
1               5                   10

<210> SEQ ID NO 67
<211> LENGTH: 11
<212> TYPE: PRT
<213> ORGANISM: Silky anteater

<400> SEQUENCE: 67

Pro Pro His Pro His Pro His Ala Arg Ile Lys
1               5                   10

<210> SEQ ID NO 68
<211> LENGTH: 11
<212> TYPE: PRT
<213> ORGANISM: Procavia capensis

<400> SEQUENCE: 68

Pro Pro Pro Leu His Pro His Ala Arg Ile Lys
1               5                   10

<210> SEQ ID NO 69
<211> LENGTH: 11
<212> TYPE: PRT
<213> ORGANISM: Didelphis marsupialis virginiana

<400> SEQUENCE: 69

Pro Pro Pro Thr His Pro His Ala Arg Ile Lys
1               5                   10

<210> SEQ ID NO 70
<211> LENGTH: 11
<212> TYPE: PRT
<213> ORGANISM: Galeopterus variegatus

<400> SEQUENCE: 70

Pro Pro Pro His His Pro His Ala Arg Ile Lys
1               5                   10
```